_US006093714A_

United States Patent [19]
Ohtsuka et al.

[11] Patent Number: 6,093,714
[45] Date of Patent: *Jul. 25, 2000

[54] TRICYCLIC BENZAZEPINE COMPOUNDS

[75] Inventors: Yasuo Ohtsuka; Toshio Nishizuka; Sohjiro Shiokawa; Seiji Tsutsumi; Kenichi Fusihara; Mami Kawaguchi; Megumi Imai; Keiko Shito; Koji Tsuchiya; Takako Iwasaki; Hiroko Ogino; Takashi Shishikura, all of Kanagawa-ken, Japan

[73] Assignee: Meiji Seika Kaisha, Ltd., Tokyo-to, Japan

[ * ] Notice: This patent is subject to a terminal disclaimer.

[21] Appl. No.: 08/973,991

[22] PCT Filed: Jun. 14, 1996

[86] PCT No.: PCT/JP96/01628

§ 371 Date: Jun. 17, 1998

§ 102(e) Date: Jun. 17, 1998

[87] PCT Pub. No.: WO97/00258

PCT Pub. Date: Jan. 3, 1997

[30] Foreign Application Priority Data

Jun. 15, 1995 [JP] Japan ..................... 7-147957

[51] Int. Cl.⁷ ................. A61K 31/41; C07D 487/04
[52] U.S. Cl. ................. 514/215; 514/359; 540/521; 548/255
[58] Field of Search ............. 540/521; 548/255; 514/215, 359

[56] References Cited

U.S. PATENT DOCUMENTS 5,686,442 11/1997 Ohtsuka et al. .................. 514/211
5,840,895 11/1998 Ohtsuka et al. .................. 544/366

FOREIGN PATENT DOCUMENTS

| 0 15 303 | 3/1991 | European Pat. Off. . |
| 4-178390 | 6/1992 | Japan . |
| WO95/18130 | 7/1995 | WIPO . |

*Primary Examiner*—Mukund J. Shah
*Assistant Examiner*—Brenda Coleman
*Attorney, Agent, or Firm*—Wenderoth, Lind & Ponack, L.L.P.

[57] ABSTRACT

Tricyclic benzazepine compounds represented by the following formula (I) and pharmacologically acceptable salts thereof are disclosed. These compounds have antiallergic activity and are useful for treatment and prevention of bronchial asthma, eczema, hives, allergic gastrointestinal troubles, allergic rhinitis, allergic conjunctivitis, etc.

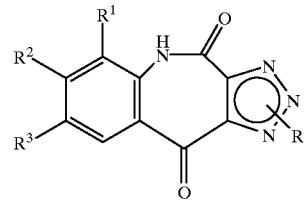

(I)

wherein R represents a hydrogen atom, substituted $C_{1-6}$ alkyl or a protective group and $R^1$, $R^2$, $R^3$, and $R^4$ represent a hydrogen atom, a hydroxyl group, substituted $C_{1-4}$ alkyl, substituted $C_{2-12}$ alkenyl, substituted $C_{1-12}$ alkoxy, or substituted amino.

20 Claims, No Drawings

TRICYCLIC BENZAZEPINE COMPOUNDS

This application is a 371 of PCT/JP96/01628, filed Jun. 14, 1996.

BACKGROUND OF THE INVENTION

1. Field of the Invention

The present invention relates to tricyclic benzazepine compounds having antiallergic activity and pharmaceutical compositions, useful for treatment and prevention of allergic diseases, comprising at least one of the tricyclic benzazepine compounds as an active ingredient. The present invention relates also to intermediate for providing the above compounds and pharmaceutical compositions and a process for producing the same.

2. Background Art

In recent years, allergic reactions induced by various stimuli, such as immunoreactions, have been clarified to be divided into two reactions, i.e., an immediate phase response which occurs immediately after the stimulation and a late phase response which occurs several hours after the stimulation (see, for example, "Late Asthmatic Responses", P. M. O'byrne, J. Dolovich and F. E. Hargreave, Am. Rev. Respir. Dis., 1987; 136: 740–751). Especially, importance has been attached to the control of the latter reaction.

In clinical studies, there are few drugs satisfactorily useful for the late phase allergic response, and the development of drugs having therapeutic effect for both the immediate phase response and the late phase response has been expected in the art.

Sodium cromoglicate are known as a representative drug for inhibiting the immediate and late phase allergic responses. This drug is clinically administered by inhalation because of its poor oral absorption. The administration by inhalation, however, is disadvantageous in that it is difficult to properly administer the drug to babies, infants, and children and, in addition, it is difficult to continuously administer the drug to patients having high sensitivity to inhalation stimuli.

For the above reason, the development of drugs, which can inhibit both the immediate and late phase responses, can be orally administered, and have excellent efficacy, have been desired in the art.

Further, in recent years, many studies on antiallergic agents and therapeutic agents for asthma have been advanced in the art. Among them, tricyclic compounds including heptacyclic compounds have been reported. Examples thereof include dibenzoxepine derivatives (Japanese Patent Laid-Open Nos. 10784/1988 and 78292/1993 and Chemical & Pharmaceutical Bulletin, vol. 39, No. 10, 2724–2728 and 2729–2733 (1991)), dibenzoxazepine derivatives (Japanese Patent Laid-Open Nos. 184963/1991, 211071/1992, and 65257/1993 and European Patent No. 5180720), and dibenzocycloheptene derivatives (International Patent WO/93-13068).

Compounds containing a hetero ring have also been reported as the antiallergic agent, and examples thereof include dibenzoxepinopyridine derivatives (European Patent No. 515158), benzocycloheptathiophene derivatives (Japanese Patent Laid-Open Nos. 294277/1991 and 226916/1992), benzocycloheptapyridine derivatives (Japanese Patent Laid-Open No. 59040/1993), triazolobenzoxepine derivatives (Journal of Chemical Research(s), 400–401 (1984)), and thieno- (pyrazolo-, thiazolo-)benzothiazepine derivatives (European Patent No. 547705).

Some of them have central or circulatory side effects and have problems of dissociation of the antiallergic action from central action, such as sedation, antidepression, or antianxiety, or circulatory action, such as vasodepression or anti-thrombogenic action. Among compounds having structures similar thereto, only few compounds, such as cyproheptadine hydrochloride, have been put as antiallergic agents on the market.

For other analogous compounds, for example, pyridobenzoxazepine derivatives have been reported as an HIV-1 reverse transcriptase inhibitor (Japanese Patent Laid-Open No. 178390/1992), triazolobenzoxazepine derivatives as an antidepressant (Journal of Heterocyclic Chemistry, vol. 22, 1693–1701 (1985)), and triazolobenzdiazepine derivatives as an antipsychotic agent (Journal of Medicinal Chemistry, vol. 32, No. 10, 2375–2381 (1989)).

As described above, the development of drugs, which can inhibit both the immediate and late phase allergic responses, can be orally administered, and have excellent efficacy, have been desired in the art.

The present inventors have previously reported, as such compounds, tricyclic benzazepine compounds containing a triazole ring (International Publication WO 95/18130).

SUMMARY OF THE INVENTION

The present inventors have now synthesized a novel group of tricyclic benzazepine compounds and found that the compounds have excellent antiallergic activity. Further, the present inventors have found intermediate compounds useful for synthesizing the novel compounds.

Accordingly, an object of the present invention is to provide a novel tricyclic benzazepine compound which has a novel type of antiallergic activity and can be orally administered.

Another object of the present invention is to provide a pharmaceutical composition for treatment and/or prevention of allergic diseases.

A further object of the present invention is to provide intermediate compounds important for synthesizing the above compound having antiallergic activity.

The tricyclic benzazepine compound according to the present invention is a compound represented by the following general formula (I) and a pharmaceutically acceptable salt thereof:

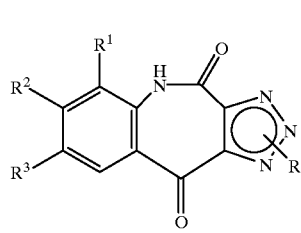

(I)

wherein

R represents any one of the following (a) to (c):
(a) a hydrogen atom;
(b) a benzyl group
which may be substituted by a halogen atom, a hydroxyl group, a nitro group, $C_{1-4}$ alkyl, or $C_{1-4}$ alkoxy; and
(c) a protective group for a triazole group, and
$R^1$, $R^2$, and $R^3$, which may be the same or different, represent any one of the following (a) to (g):
- (a) a hydrogen atom;
- (b) $C_{1-4}$ alkyl
  which may be substituted by a halogen atom, a hydroxyl group, or $C_{1-4}$ alkoxy;
- (c) an optionally protected hydroxyl group;
- (d) $C_{2-12}$ alkenyl
  which may be substituted by
  - (1) group $-CONR\ R^4R^5$
    wherein $R^4$ and $R^5$, which may be the same or different, represent
    - (i) a hydrogen atom,
    - (ii) phenyl
      which may be substituted by a halogen atom, a hydroxyl group, $C_{1-4}$ alkyl optionally substituted by a saturated five- to seven-membered heterocyclic ring containing one or two nitrogen atoms optionally substituted by $C_{1-4}$ alkyl, $C_{1-4}$ alkoxy, or carboxyl, or
      which may be substituted by a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring, or
    - (iii) a saturated or unsaturated five- to seven-membered heterocyclic ring containing one or more atoms selected from oxygen, nitrogen, and sulfur atoms,
      the heterocyclic ring being optionally substituted by $C_{1-4}$ alkyl or phenyl $C_{1-4}$ alkyl or optionally condensed with other ring to form a bicyclic ring, or
  - (2) a saturated or unsaturated five- to seven-membered heterocyclic ring containing one or more atoms selected from oxygen, nitrogen, and sulfur atoms,
    the heterocyclic ring being optionally substituted by $C_{1-4}$ alkyl or phenyl $C_{1-4}$ alkyl or optionally condensed with other ring to form a bicyclic ring;
- (e) $C_{1-12}$ alkoxy
  which may be substituted by
  - (1) amino
    which may be substituted by $C_{1-4}$ alkyl, acyl, or a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring, the nitrogen atom of the amino optionally constituting a part of a ring to form a saturated five- to seven-membered heterocyclic ring, or
  - (2) group $-CONR^6R^7$
    wherein $R^6$ and $R^7$, which may be the same or different, represent
    - (i) a hydrogen atom, or
    - (ii) $C_{1-4}$ alkyl
      which may be substituted by a saturated five- to seven-membered heterocyclic ring containing one or more atoms selected from oxygen, nitrogen, and sulfur atoms;
- (f) group $-NR^8R^9$
  wherein $R^8$ and $R^9$, which may be the same or different, represent
  - (1) a hydrogen atom,
  - (2) $C_{1-4}$ alkyl,
  - (3) group $-COR^{10}$
    wherein $R^{10}$ represents
    - (i) a hydrogen atom,
    - (ii) $C_{1-4}$ alkyl
      which may be substituted by a halogen atom, a hydroxyl group, $C_{1-4}$ alkoxy, or cycloalkyl, or
    - (iii) phenyl
      which may be substituted by a halogen atom, a hydroxyl group, $C_{1-4}$ alkyl, or $C_{1-6}$ alkoxy, the alkoxy being optionally substituted by phenyl,
  - (4) group $-CO_2R^{11}$
    wherein $R^{11}$ represents
    - (i) $C_{1-4}$ alkyl
      which may be substituted by a halogen atom, a hydroxyl group, $C_{1-4}$ alkoxy, or cycloalkyl,
    - (ii) phenyl $C_{1-4}$ alkyl
      which may be substituted by a halogen atom, a hydroxyl group, $C_{1-4}$ alkyl, or $C_{1-4}$ alkoxy,
    - (iii) phenyl
      which may be substituted by a halogen atom, a hydroxyl group, $C_{1-4}$ alkyl, or $C_{1-4}$ alkoxy, or
  - (5) group $-SO_2R^{12}$
    wherein $R^{12}$ represents
    - (i) $C_{1-10}$ alkyl
      which may be substituted by a halogen atom, a hydroxyl group, an oxo group, $C_{1-4}$ alkoxy, or cycloalkyl,
    - (ii) phenyl
      which may be substituted by a halogen atom, a hydroxyl group, $C_{1-4}$ alkyl or $C_{1-4}$ alkoxy or may be condensed with other ring to form a bicyclic ring;
- (g) group $-(CH_2)_p-CONR^{13}R^{14}$
  wherein $R^{13}$ and $R^{14}$, which may be the same or different, represent
  - (1) a hydrogen atom,
  - (2) $C_{1-4}$ alkyl
    which may be substituted by a saturated five- to seven-membered heterocyclic ring containing one or two atoms selected from oxygen, nitrogen, and sulfur atoms,
  - (3) a saturated or unsaturated five- to seven-membered heterocyclic ring formed by combining $R^{13}$ and $R^{14}$ with a nitrogen atom bonded thereto, the heterocyclic ring optionally containing one or more atoms selected from oxygen, nitrogen, and sulfur atoms or being optionally condensed with other ring to form a bicyclic ring, or
  - (4) a saturated or unsaturated five- to seven-membered heterocyclic ring containing one or two atoms selected from oxygen, nitrogen, and sulfur atoms, and
  p is an integer of 1 to 6,
any two of $R^1$, $R^2$, and $R^3$ optionally combining together to form group $-O-(CH_2)_q-$ wherein q is an integer of 1 to 4.

The pharmaceutical composition for treatment and prevention of allergic diseases according to the present invention comprises as an active ingredient the compound represented by the general formula (I) or a pharmacologically acceptable salt thereof.

The compounds represented by the general formula (I) can inhibit not only an immediate phase allergic response but also a late phase allergic response. Further, these compounds, when orally administered, can develop the antiallergic action which is persistent and hence superior to that exerted by the conventional antiallergic agents.

The intermediate compounds for synthesizing the compound represented by the formula (I) according to the present invention are compounds represented by the following general formulae (II), (III), and (IV) or salts thereof:

Specifically, the compound represented by the general formula (II) according to the present invention is a compound represented by the following formula or a salt thereof:

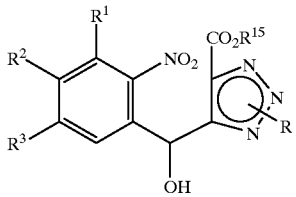

(II)

wherein R, $R^1$, $R^2$, and $R^3$ are as defined above in connection with the formula (I) and $R^{15}$ represents a hydrogen atom, optionally substituted $C_{1-6}$ alkyl, or a protective group of carboxyl.

The compound represented by the general formula (III) according to the present invention is a compound represented by the following formula or a salt thereof:

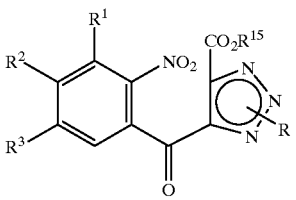

(III)

wherein R, $R^1$, $R^2$, and $R^3$ are as defined above in connection with the formula (I) and $R^{15}$ is as defined above in connection with the formula (II).

The compound represented by the general formula (IV) according to the present invention is a compound represented by the following formula or a salt thereof:

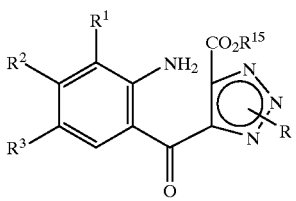

(IV)

wherein R, $R^1$, $R^2$, and $R^3$ are as defined above in connection with the formula (I) and $R^{15}$ is as defined in above in connection with the formula (II).

DETAILED DESCRIPTION THE INVENTION

Compounds represented by general formula (I)

As used herein, "alkyl" as a group or a portion of a group, particularly "alkyl" as "$C_{1-6}$ alkyl," or "$C_{1-4}$ alkyl," or as a portion of "$C_{2-12}$ alkenyl," "$C_{1-12}$ alkoxy," or "$C_{1-4}$ alkoxy" may be straight-chain or branched. The term "halogen atom" used herein means a fluorine, chlorine, bromine, or iodine atom.

In the general formula (I), R represents one of the above (a) to (c). One or more hydrogen atoms on the benzene ring of the benzyl group (b) may be substituted by a halogen atom, a hydroxyl group, a nitro group, $C_{1-4}$ alkyl, or $C_{1-4}$ alkoxy. Preferred examples thereof include a hydroxyl group substituted at the 4-position and $C_{1-4}$ alkoxy. Specific examples of preferred R include benzyl, 4-methylbenzyl, 4-chlorobenzyl, 4-hydroxybenzyl, 4-nitrobenzyl, and 4-methoxybenzyl.

Furthermore, R may represent a protective group for the triazole group. Protective groups usable herein include, for example, benzyl, diphenylmethyl, triphenylmethyl, 4-methoxybenzyl, 3,4-dimethoxybenzyl, 3,4,5-trimethoxybenzyl, trimethylsilyl, tert-butylmethylsilyl, methoxymethyl, benzyloxymethyl, and methoxyethoxy.

In the general formula (I), $R^1$, $R^2$, and $R^3$ each independently represent any one of the above (a) to (g).

Examples of the protective group for the hydroxyl group (c) include acetyl, chloroacetyl, trichloroacetyl, benzoyl, 4-methylbenzoyl, 4-nitrobenzoyl, 3-oxobutyryl, benzyl, diphenylmethyl, triphenylmethyl, 4-methoxybenzyl, 3,4-dimethoxybenzyl, methoxymethyl, methoxyethoxymethyl, benzyloxymethyl, trimethylsilyl, tert-butyldimethylsilyl, trimethylsilylethoxymethoxy.

The $C_{2-12}$ alkenyl (d) is preferably $C_{2-6}$ alkenyl, more preferably $C_{2-4}$ alkenyl, most preferably vinyl. One or more hydrogen atoms in the alkenyl group may be substituted by (1) group —$CONR^5R^6$ or (2) a saturated or unsaturated five- to seven-membered heterocyclic ring containing one or more atoms selected from oxygen, nitrogen, and sulfur atoms.

In the group —$CONR^4R^5$ (1), $R^4$ and $R^5$ may be the same or different and represent (i) a hydrogen atom, (ii) -phenyl, or (iii) a saturated or unsaturated five- to seven-membered heterocyclic ring containing one or more atoms selected from oxygen, nitrogen, and sulfur atoms.

In this case, one or more hydrogen atoms on the phenyl (ii) may be substituted by a halogen atom, a hydroxyl group, $C_{1-4}$ alkyl, or carboxyl. Preferred examples of the phenyl include 2-carboxyphenyl, 4-carboxyphenyl, 2-hydroxyphenyl, 4-hydroxyphenyl, and 4-methoxyphenyl.

Preferred examples of the saturated or unsaturated five- to seven-membered heterocyclic ring (2) containing one or more atoms selected from oxygen, nitrogen, and sulfur atoms include 2-pyrrolyl, 3-pyrrolyl, 2-furyl, 2-pyridyl, 3-pyridyl, 4-pyridyl, 2-thiazolyl, 2-quinolinyl, and 2-pyranyl. The heterocyclic ring may be substituted by $C_{1-4}$ alkyl or phenyl $C_{1-4}$ alkyl. Specific examples thereof include $C_{1-4}$ alkyl- or phenyl $C_{1-4}$ alkyl-substituted 2-pyrrolyl, 3-pyrrolyl, 2-furyl, 2-pyridyl, 3-pyridyl, 4-pyridyl, 2-thiazolyl, 2-quinolyl, and 2-pyranyl. The heterocyclic ring may be condensed with other ring to form a bicyclic ring, and example thereof include 2-pyrrolyl, 3-pyrrolyl, 2-furyl, 2-pyridyl, 3-pyridyl, 4-pyridyl, 2-thiazolyl, 2-quinolyl, and 2-pyranyl, which have been condensed with phenyl.

The $C_{1-12}$ alkoxy (e) is preferably $C_{2-6}$ alkoxy, more preferably $C_{2-4}$ alkoxy. This alkoxy may be substituted by (1) amino or (2) group —$CONR^6R^7$.

One or more hydrogen atoms on the amino (1) may be substituted by $C_{1-4}$ alkyl, acyl, or a saturated or unsaturated five- to seven-membered heterocyclic ring containing one or more atoms selected from oxygen, nitrogen, and sulfur atoms. The nitrogen atom of the amino may constitute a part of a ring to form a saturated five- to seven-membered heterocyclic ring. Preferred examples of the heterocyclic ring include morpholino, pyrrolidyl, piperidyl, and piperazyl. The heterocyclic ring may have a substituent, and specific examples of the substituent include $C_{1-4}$ alkyl and phenyl $C_{1-4}$ alkyl. More specific examples of the substituted heterocyclic ring include morpholino, pyrrolidyl, piperidyl, and piperazyl which have been substituted by $C_{1-4}$ alkyl or phenyl $C_{1-4}$ alkyl.

In the group —$CONR^6R^7$ (2), $R^6$ and $R^7$ may be the same or different and represent a hydrogen atom or $C_{1-4}$ alkyl. This alkyl may be substituted by a saturated five- to seven-membered heterocyclic ring containing one or more atoms selected from oxygen, nitrogen, and sulfur atoms. Preferred examples of the heterocyclic ring include 2-pyridyl, 3-pyridyl, 4-pyridyl, and 2-furyl.

In the group —$NR^8R^9$ (f), $R^8$ and $R^9$ may be the same or different and represent (1) a hydrogen atom, (2) $C_{1-4}$ alkyl, (3) group —$COR^{10}$, (4) group —$CO_2R^1$, or (5) group —$SO_2R^{12}$.

In the group —$COR^{10}$ (3), $R^{10}$ represents (i) a hydrogen atom, (ii) $C_{1-4}$ alkyl, (iii) phenyl. In this case, phenyl (iii) may be substituted by a halogen atom, a hydroxyl group, $C_{1-4}$ alkyl, or $C_{1-6}$ alkoxy. Further, the $C_{1-6}$ alkoxy may be substituted by phenyl.

In the group —$CO_2R^{11}$ (4), $R^{11}$ represents (i) $C_{1-4}$ alkyl, (ii) phenyl $C_{1-4}$ alkyl, or (iii) phenyl. In this case, the $C_{1-4}$ alkyl (i) may be substituted by a halogen atom, a hydroxyl group, $C_{1-4}$ alkoxy, or cycloalkyl, and examples thereof include methyl, ethyl, allyl, benzyl, tert-butyl, and 2,2,2-trichloroethyl. The phenyl (iii) may be substituted by a halogen atom, a hydroxyl group, $C_{1-4}$ alkyl, or $C_{1-4}$ alkoxy.

In the group —$SO_2R^{12}$ (5), $R^{12}$ represents $C_{1-10}$ alkyl or phenyl and, preferred examples thereof include methyl, ethyl, tert-butyl, cyclohexyl, 10-(2-oxo)bornyl, phenyl, 4-methylphenyl, 4-methoxyphenyl, 1-naphthyl, and 2-naphthyl.

In the group —$(CH_2)_p$—$CONR^{13}R^{14}$ (g), $R^{13}$ and $R^{14}$ may be the same or different and represent (1) a hydrogen atom, (2) $C_{1-4}$ alkyl, (3) a saturated or unsaturated five- to seven-membered heterocyclic ring formed by combining $R^{13}$ and $R^{14}$ with a nitrogen atom bonded thereto, or (4) a saturated or unsaturated five- to seven-membered heterocyclic ring containing one or two atoms selected from oxygen, nitrogen, and sulfur atoms.

In this case, the $C_{1-4}$ alkyl (2) may be substituted by a saturated five- to seven-membered heterocyclic ring containing one or two atoms selected from oxygen, nitrogen, and sulfur atoms. Examples of such alkyls include 2-pyridylmethyl, 3-pyridylmethyl, 4-pyridylmethyl, and 2-furfuryl.

The saturated or unsaturated five- to seven-membered heterocyclic ring (3) formed by combining $R^{13}$ and $R^{14}$ with a nitrogen atom bonded thereto may contain one or more atoms selected from oxygen, nitrogen, and sulfur atoms or may be condensed with other ring to form a bicyclic ring. Preferred examples of the heterocyclic ring (group) include piperidino, piperazino, N-methylpiperazino, morpholino, succimido, indolyl, 4-methylindolyl, 5-methylindolyl, isoindolyl, phthalimido, 4-methylphthaloyl, 1,1-dioxo-2-benzothiazolyl, 1,2,3,4-tetrahydroquinolino, 1,2,3,4-tetrahydroisoquinolino, and 2-methoxycarbonyl-4,5,6,7 tetrahydrothieno[3,2-c]pyridyl rings (groups).

Examples of the saturated or unsaturated five- to seven-membered heterocyclic ring (4) containing one or two atoms selected from oxygen, nitrogen, and sulfur atoms include 2-pyridyl, 3-pyridyl, 4-pyridyl, and 2-thiazolyl.

p is an integer of 1 to 6, preferably 1 to 4, most preferably 2.

In the compounds according to the present invention, there may exist tautomers derived from the triazole ring and cis-trans isomers derived from the alkenyl as the substituents, and any of the isomers and any mixtures of the isomers fall within the scope of the present invention.

Preferred groups of compounds among the compounds represented by the general formula (I) according to the present invention are such that R represents a hydrogen atom and $R^1$, $R^2$, and $R^3$ represent a hydrogen atom, substituted or unsubstituted $C_{1-6}$ alkyl, substituted or unsubstituted $C_{2-12}$ alkenyl, substituted or unsubstituted $C_{1-12}$ alkoxy, or amino.

More specific examples of preferred groups of compounds include:

a group of compounds wherein R represents a hydrogen atom and $R^1$, $R^2$, and $R^3$ represent a hydrogen atom or substituted $C_{1-4}$ alkyl:

a group of compounds wherein R represents a hydrogen atom and $R^1$, $R^2$, and $R^3$ represent a hydrogen atom or substituted $C_{1-12}$ alkoxy;

a group of compounds wherein R and $R^1$ represent a hydrogen atom and $R^2$ and $R^3$ represent a hydrogen atom, substituted $C_{1-4}$ alkyl, substituted $C_{2-12}$ alkenyl, or substituted $C_{1-12}$ alkoxy;

a group of compounds wherein R and $R^1$ represent a hydrogen atom and $R^2$ and $R^3$ represent a hydrogen atom or substituted $C_{1-4}$ alkyl;

a group of compounds wherein R and $R^1$ represent a hydrogen atom and $R^2$ and $R^3$ represent a hydrogen atom or substituted $C_{2-12}$ alkenyl;

a group of compounds wherein R and $R^1$ represent a hydrogen atom and $R^2$ and $R^3$ represent a hydrogen atom or substituted $C_{1-12}$ alkoxy;

a group of compounds wherein R and $R^1$ represent a hydrogen atom and $R^2$ and $R^3$ represent a hydrogen atom, substituted $C_{1-4}$ alkyl, or substituted $C_{1-12}$ alkoxy;

a group of compounds wherein R, $R^1$, and $R^3$ represent a hydrogen atom and R represents substituted $C_{1-4}$ alkyl;

a group of compounds wherein R, $R^1$, and $R^3$ represent a hydrogen atom and $R^2$ represents substituted $C_{2-12}$ alkenyl;

a group of compounds wherein R, $R^1$, and $R^3$ represent a hydrogen atom and $R^2$ represents substituted $C_{1-12}$ alkoxy;

a group of compounds wherein R, $R^1$, and $R^3$ represent a hydrogen atom and $R^2$ represents substituted or unsubstituted amino; and a group of compounds wherein R, $R^2$, and $R^4$ represent a hydrogen atom and $R^1$ and $R^3$ represent substituted $C_{1-4}$ alkyl.

Specific examples of particularly preferred compounds include:

7-(2-(N-(2-carboxyphenyl)carbamoyl)-(E)-ethenyl)-4(5H), 10-dioxo-1H-1,2,3-triazolo[4,5-c][1]benzazepine;

4(5H ),10-dioxo-7-(2-(N-(2-pyridyl)methyl)carbamoyl) ethyl-1H-1,2,3-triazolo[4,5-c][1]benzazepine;

4(5H),10-dioxo-7-(2-(N-methyl-N-(2-pyridyl)methyl) carbamoyl)ethyl-1H-1,2,3-triazolo[4,5-c][1]benzazepine;

7-(2-(N-ethyl-N-(2-pyridyl)methyl)carbamoyl)ethyl-4(5H), 10-dioxo-1H-1,2,3-triazolo[4,5-c][1]benzazepine;

7-(2-(N,N-bis(2-pyridylmethyl))carbamoyl)ethyl-4(5H),10-dioxo-1H-1,2,3-triazolo[4,5-c][1]benzazepine;

7-(2-(1,2,3,4-tetrahydro-2-isoquinolyl)carbonylethyl)-4 (5H),10-dioxo-1H-1,2,3-triazolo[4,5-c][1]benzazepine;

7-(2-(2-methoxycarbonyl-4,5,6,7-tetrahydrothieno[3,2-c]
pyridin-5-yl)carbonylethyl)-4(5H),10-dioxo-1H-1,2,3-
triazolo[4,5-c][1]benzazepine;

7-(2-(4-methylpiperazin-1-yl)carbonylethyl)-4(5H),10-
dioxo-1H-1,2,3-triazolo[4,5-c][1]benzazepine;

7-(2-(N-(4-pyridylamino))carbamoyl)ethyl-4(5H),10-
dioxo-1H-1,2,3-triazolo[4,5-c][1]benzazepine;

4(5H),10-dioxo-7-(2-(4-pyridyl)-(E)-ethenyl)-1H-1,2,3-
triazolo[4,5-c][1]benzazepine;

4(5H),10-dioxo-7-(2-(2-pyridyl)-(E)-ethenyl)-1H-1,2,3-
triazolo[4,5-c][1]benzazepine;

7-(3-morpholinopropoxy)-4(5H),10-dioxo-1H-1,2,3-
triazolo[4,5-c][1]benzazepine;

7-(3-(4-methyl-1-piperazino)propoxy)-4(5H),10-dioxo-1H-
1,2,3-triazolo[4,5-c][1]benzazepine;

7-(3-(4-benzylpiperidyl)propoxy)-4(5H),10-dioxo-1H-1,2,
3-triazolo[4,5-c][1]benzazepine;

7-(N-ethyl-N-(2-pyridylmethyl)carbamoylmethyloxy)-4
(5H),10-dioxo-1H-1,2,3-triazolo[4,5-c][1]benzazepine;

4(5H),10-dioxo-7-(N-(2-pyridylmethyl)
carbamoylmethyloxy)-1H-1,2,3-triazolo[4,5-c][1]
benzazepine;

4(5H),10-dioxo-7-(4-toluoyloxy)-1H-1,2,3-triazolo[4,5-c]
[1]benzazepine;

4(5H),10-dioxo-7-(N,N-bis(2-pyridylmethyl)
carbamoylmethyloxy)-1H-1,2,3-triazolo[4,5-c][1]
benzazepine;

7-(N-methyl-N-(2-pyridylmethyl)carbamoylmethyloxy)-4
(5H),10-dioxo-1H-1,2,3-triazolo[4,5-c][1]benzazepine;

7-amino-4(5H),10-dioxo-1H-1,2,3-triazolo[4,5-c][1]
benzazepine;

7-acetylamino-4(5H),10-dioxo-1H-1,2,3-triazolo[4,5-c][1]
benzazepine;

4(5H),10-dioxo-7-(4-(4-phenylbutoxy)benzoylamino)-1H-
1,2,3-triazolo[4,5-c][1]benzazepine;

8-isopropoxy-7-methoxy-4(5H),10-dioxo-1H-1,2,3-triazolo
[4,5-c][1]benzazepine;

7-isopropoxy-8-methoxy-4(5H),10-dioxo-1H-1,2,3-triazolo
[4,5-c][1]benzazepine;

7,8-diisopropoxy-4(5H),10-dioxo-1H-1,2,3-triazolo[4,5-ac]
[1]benzazepine;

7,8-methylenedioxy-4(5H),10-dioxo-1H-1,2,3-triazolo[4,5-
c][1]benzazepine;

8-(4-methoxyphenacyloxy)-7-methyl-4(5H),10-dioxo-1H-
1,2,3-triazolo[4,5-c][1]benzazepine;

8-hydroxy-7-methyl-4(5H),10-dioxo-1H-1,2,3-triazolo[4,5-
c][1]benzazepine;

6,8-dimethyl-4(5H),10-dioxo-1H-1,2,3-triazolo[4,5-c][1]
benzazepine;

6,7,8-trimethoxy-4(5H),10-dioxo-1H-1,2,3-triazolo[4,5-ac]
[1]benzazepine;

4(5H),10-dioxo-7-(2-(3-pyridyl)ethenyl)-1H-1,2,3-triazolo
[4,5-c][1]benzazepine;

7-(2-(6-methyl-2-pyridyl)-(E)-ethenyl)-4(5H),10-dioxo-
1H-1,2,3-triazolo[4,5-c][1]benzazepine;

4(5H),10-dioxo-7-(2-(2-quinolyl)-(E)-ethenyl)-1H-1,2,3-
triazolo[4,5-c][1]benzazepine; and 7-trifluoromethyl-4(5H),10-dioxo-1H-1,2,3-triazolo[4,5-c]
[1]benzazepine.

The compounds according to the present invention may
be converted to pharmacologically acceptable salts thereof.
Such salts usable herein include medically acceptable non-
toxic salts. Preferred are salts of alkali metals and alkaline
earth metals, such as sodium, potassium, and calcium salts;
salts of hydrohalogenic acids such as hydrofluoric acid,
hydrochloric acid, hydrobromic acid and hydroiodic acid;
inorganic acid salts such as nitrate, perchlorate, sulfate, and
phosphate; organic acid salts, for example, salts of lower
alkylsulfonic acids, such as methanesulfonic acid, trifluo-
romethanesulfonic acid, and ethanesulfonic acid, and salts of
other organic acids, such as benzenesulfonic acid,
p-toluenesulfonic acid, tartaric acid, oxalic acid, and maleic
acid; and salts of amino acids such as glutamic acid and
aspartic acid.

Compounds represented by general formulae (II), (III),
and (VI)

The compounds represented by the formulae (II), (III),
and (VI) according to the present invention are useful as
intermediates for synthesizing the compounds represented
by the formula (I).

In these formulae, R, $R^1$, $R^2$, and $R^3$ may be fundamen-
tally the same as R, $R^1_1$ $R^2$, and $R^3$ in the corresponding
compound represented by the formula (I). Therefore, pre-
ferred examples of R, $R^1$, $R^2$, and $R^3$ described above in
connection with the compound represented by the formula
(I) are preferred also in R, $R^1$, $R^2$, and $R^3$ in the formulae
(II), (III), and (IV).

In the formulae (II), (III), and (IV), $R^{15}$ represents a
hydrogen atom, $C_{1-6}$ alkyl, or carboxyl. In this case, the $C_{1-6}$
alkyl may optionally be substituted, and examples thereof
include methyl, ethyl, propyl, isopropyl, tert-butyl,
cyclohexyl, benzyl, 4-methoxybenzyl, methoxymethyl,
methoxyethoxymethyl, methylthiomethyl, 2,2,2-
trichloroethyloxymethyl, and allyl.

Synthesis of compounds represented by general formula
(I)

The compounds according to the present invention may
be synthesized according to the following scheme which is
the same as the reaction process (A) described in Interna-
tional Publication WO 95/18130.

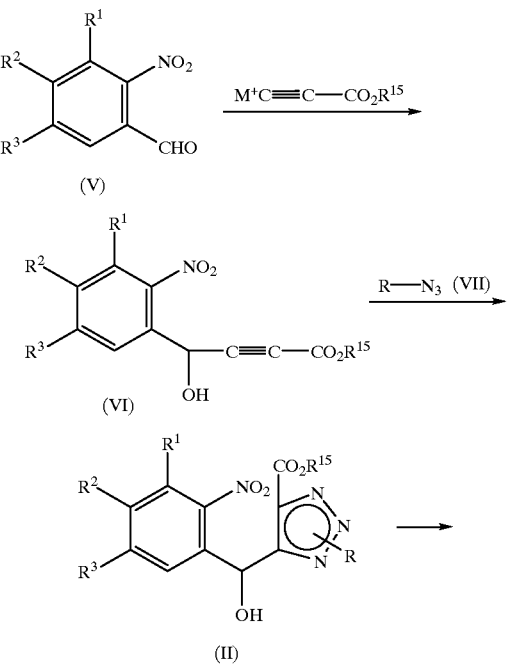

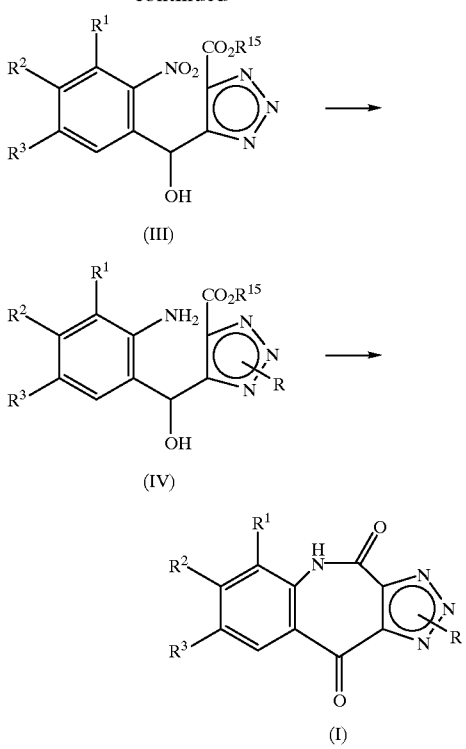

wherein R, $R^1$, $R^2$, $R^3$, and $R^{15}$ are as defined above.

Synthesis of compounds represented by general formula (II):

The compound represented by the general formula (II) may be synthesized using a substituted 2-nitrobenzaldehyde compound (V) as a starting compound. At the outset, the compound (V) is reacted with an alkali metal salt of a propiolic ester, which can be easily prepared from a propiolic ester by a conventional method, in a solvent inert to the reaction (for example, tetrahydrofuran) to prepare a compound (VI). The reaction is performed at a temperature of preferably −78 to 0° C. usually for 0.1 to 1 hr. The compound (VI) is then reacted with an azide compound (VII): R—$N_3$ in a solvent inert to the reaction (for example, toluene, dimethylformamide, acetate, dioxane, or a mixture thereof) to prepare a compound represented by the general formula (II). The reaction is performed at a temperature of preferably 30 to 110° C. usually for 5 to 24 hr.

The azide compound (VII) may be prepared, for example, by a method described in J. R. E. Hoover and A. R. Day (J. Amer. Chem. Soc., 78, 5832 (1956)), D. R. Buckle and C. J. M. Rockell (J. Chem. Soc. Perkin I, 1982, 627 ), B. Loubinoux, J. -L. Colin and S. Tabbache (J. Heterocyclic Chem., 21, 1669 (1984)), I. F. Cottrell, D. Hands, P. G. Houghton, G. R. Humphrey and S. H. B. Wright (J. Heterocyclic Chem., 28, 301 (1991)). Alkali metals usable in the alkali metal salt of propiolic ester to be reacted with the compound (V) include lithium, sodium, and potassium with lithium being preferred.

Although the compound represented by the general formula (II) prepared herein is a mixture of isomers (positional isomers of R) with respect to the triazole portion, it as such may be used in the next reaction without separation.

The 2-nitrobenzaldehyde compound (V) as the starting compound may be prepared, for example, by a method described in A. D. Batcho and W. Leimgruber (U.S. Pat. No. 3,976,639 (1976), U.S. Pat. No. 3,732,245 (1973)), R. D. Clark and D. B. Repke (Heterocycles, 22, 195 (1984)), and M. G. Vetelino and J. W. Coe Tetrahedron Lett., 35, 219 (1994)).

Synthesis of compound represented by general formula (IV):

The compound represented by the general formula (IV) may be produced by oxidizing the compound represented by the formula (II) to prepare a compound (III) and reducing the compound (III). Oxidation methods usable herein include oxidation with a metallic oxidizing agent, catalytic air oxidation, and organic oxidation. Preferred is oxidation with manganese dioxide in a methylene chloride solution (at room temperature) or oxidation using dimethylsulfoxide in a methylene chloride solution (for example, in a dimethylsulfoxide/oxalyl chloride/triethylamine system at −78° C. to 25° C.).

In the stage of the compound (III), the mixture of isomers (positional isomers of R) with respect to the triazole portion may be subjected to separation or alternatively, as such, may be used, without separation, to allow the reaction to proceed to the compound represented by the formula (I).

The compound (III) may be reduced to prepare an amino compound represented by the general formula (IV). Preferably, the reduction is performed by commonly used catalytic reduction, for example, in the presence of a nickel catalyst or a palladium catalyst. Regarding the solvent, acetic acid, ethyl acetate, alcoholic solvent such as ethanol, dioxane, tetrahydrofuran, water and the like may be used alone or as a mixture of two or more. Further, addition of an acid, such as hydrochloric acid, sulfuric acid, or hydroperchloric acid, can promote the reaction. For the reduction, it is also possible to use a method using a metal, such as iron or zinc.

Synthesis of compound represented by general formula (I)

Cyclization:

The compound represented by the general formula (I) may be produced by cyclizing a compound represented by the general formula (IV) and, if necessary, conducting deprotection.

Specifically, a compound represented by the general formula (IV) may be reacted in a solvent inert to the reaction (for example, toluene, dimethylformamide, dimethylsulfoxide, dioxane, tetrahydrofuran, methanol, ethanol, or a mixture thereof) in the presence of a base, such as sodium hydride, sodium methoxide, potassium hydride, or potassium tert-butoxide at a temperature of 0 to 100° C. (for example, 20 to 5° C. in the case of a reaction performed in methanol in the presence of sodium methoxide) for 1 to 48 hr, usually 2 to 24 hr, thereby preparing the compound represented by the general formula (I).

Deprotection

In the compound represented by the general formula (I), when the triazole group is in a protected state, the deprotection may be performed by the following conventional method. For example, when the protective group R is benzyl, diphenylmethyl, triphenylmethyl, 4-methoxybenzyl, 3,4,5-trimethoxybenzyl, benzyloxymethyl, or trimethylsilyl, according to a method described, for example, in D. R. Buckle and C. J. M. Rockell (J. Chem. Soc. Perkin I, 1982, 627) and F. E. Nielsen and E. B. Pedersen (J. Heterocyclic Chem., 22, 1693 (1985)), a mineral acid, such as dilute hydrochloric acid or dilute sulfuric acid, or an organic acid, such as acetic acid or trifluoroacetic acid, is allowed to act, as such or after dilution with a solvent inert to the reaction (for example, methylene chloride or toluene), on the compound (I) to remove the protective group, thereby preparing the compound represented by the formula (I) wherein R=H.

In the above reaction formulae, when the substituent $R^1$, $R^2$, or $R^3$ is protected amino, hydroxyl, or carbonyl or when the substituent has protected amino, hydroxyl, or carbonyl, the deprotection may be, if necessary, performed in a proper reaction process, preferably before or after the removal of the protective group for the triazole group, thereby preparing the compound represented by the general formula (I). In this case, as with the conventional method, a suitable reagent for the deprotection is selected according to the protective group of amino, hydroxyl, or carbonyl, or according to the reaction process, and the deprotection is performed using the selected reagent by a conventional method.

Further, the deprotected amino, hydroxyl, or carbonyl may be subjected to alkylation, acylation, sulfonation, etherification, a carbon elongation (carbon chain extension) reaction, such as Wittig reaction, oxidation, reduction, and hydrolysis, either alone or in combination, under conventional reaction conditions, to prepare a contemplated compound represented by the general formula (I).

The compound represented by the general formula (I) synthesized by the above production process may be purified by a conventional purification method, for example, recrystallization, reprecipitation, solvent extraction, column chromatography on silica gel, or column chromatography on adsorptive resin.

Use of compounds/pharmaceutical composition

The compounds represented by the general formula (I) have antiallergic activity and hence are useful for treatment and prevention of diseases in which allergy participate. Specifically, the compounds according to the present invention can be used as therapeutic agents, for allergic diseases, which are useful for treatment and prevention of diseases, in animals including a human being, such as bronchial asthma, eczema, hives, allergic gastrointestinal troubles, allergic rhinitis, and allergic conjunctivitis.

A pharmaceutical composition comprising as an active ingredient a compound represented by the general formula (I) or a pharmacologically acceptable salt thereof can be administered either orally or parenterally (e.g., inhalation administration, nasal dropping, eye dropping, subcutaneous administration, intravenous injection, intramuscular injection, rectal administration, and percutaneous administration), preferably orally, as drugs, in dosage forms suitable for oral or parenteral administration, to humans or animals other than humans.

For example, the pharmaceutical composition may be made into a preparation suitable for an administration route to be adopted. Specifically, it may be made into any of the following preparations: a tablet, a capsule, a granule, a powder, a pill, subtilized granule, a troche, a syrup, or an emulsion for oral administration; an inhalant, a nasal drop, or an eye drop for a liquid for external use; an injection for intravenous or intramuscular injection; a preparation for rectal administration; an oleaginous suppository; an aqueous suppository: and a paint such as an ointment.

The above various preparations may be prepared by a conventional method using an excipient, a filler, a binder, a wetting agent, a disintegrating agent, a surface-active agent, a lubricant, a dispersing agent, a buffer, a preservative, a solubilizer, an antiseptic, a flavor, a soothing agent, a stabilizer and the like. Examples of the above additives which are nontoxic and employable in the preparations include lactose, fructose, glucose, starch, gelatin, magnesium carbonate, synthetic magnesium silicate, talc, magnesium stearate, methyl cellulose, carboxymethyl cellulose or a salt thereof, gum arabic, olive oil, propylene glycol, polyethylene glycol, syrup, vaseline, glycerin, ethanol, citric acid, sodium chloride, sodium sulfite and sodium phosphate.

Although the content of the compound according to the present invention in the pharmaceutical composition depends on the preparations, it is generally in the range of from 1 to 70% by weight, preferably from about 5 to 50% by weight, based on the whole composition. Specific examples of the method for preparing pharmaceutical preparations are described in preparation examples below. The dosage for treatment and prevention of allergic diseases may be appropriately determined individually in view of the direction for use, the age and sex of patients, the seriousness of symptoms and the like. In general, however, it ranges from about 0.1 to 2,000 mg/adult/day, preferably about 5 to 400 mg/adult/day, which is administered either at one time or dividedly several times.

EXAMPLES

The compounds of the present invention will be described in more detail with reference to the following examples and pharmacological test example.

NMR data in the following examples are those measured by 400 MHz NMR and were expressed in terms of δ value (ppm) based on TMS.

Example 1

7-(2-(N-(2-Carboxyphenyl)carbamoyl)-(E)-ethenyl)-4(5H), 10-dioxo-1H-1,2,3-triazolo[4,5-c][1]benzazepine (a) Tributylamine (0.13 ml, 0.546 mmol), 2-chloro-1-methylpyridinium p-toluenesulfonate (168 mg, 0.560 mmol), 3,4-dihydro-2H-pyrido[1,2-a]pyrimidin-2-one (99 mg, 0.668 mmol), and methyl 2-aminobenzoate (0.1 ml, 0.773 mmol) were added at room temperature to a solution of 7-(2-carboxy-(E)-ethenyl)-1-(4-methoxybenzyl)-4(5H), 10-dioxo-1H-1,2,3-triazolo[4,5-c][1]benzazepine (206 mg, 0.509 mmol) in N,N-dimethylformamide (20 ml) described in Example 42 (b) of International Publication WO 95/18130. The mixture was stirred at room temperature for 11.5 hr. Further, tributylamine (0.18 ml, 0.756 mmol), 2-chloro-1-methylpyridinium p-toluenesulfonate (241 mg, 0.804 mmol), 3,4-dihydro-2H-pyrido[1,2-a]pyrimidin-2-one (129 mg, 0.871 mmol), and methyl 2-aminobenzoate (0.13 ml, 1.00 mmol) were added thereto, followed by stirring for 11.5 hr. The solvent was removed under reduced pressure, the resultant precipitate was collected by filtration, washed with methanol and water, and then dried to give 1-(4-methoxybenzyl)-7-(2-(N-(2-methoxycarbonylphenyl) carbamoyl)-(E)-ethenyl)-4(5H),10-dioxo-1H-1,2,3-triazolo [4,5-c][1]benzazepine as yellow crystalline powder (54 mg, 19.7%).

$^1$H-NMR (DMSO-d$_6$):δ 3.72 (3H, s), 3.89 (3H, s), 6.00 (2H,s), 6.91 (2H, d), 7.03 (1H, d), 7.2–7.4 (1H, m), 7.30 (2H, d), 7.57 (1H, d), 7.64–7.70 (2H, m), 7.78 (1H, s), 7.94–7.97 (1H, m), 8.20–8.30 (1H, m), 8.36–8.39 (1H, m), 10.97 (1H, brs), 11.38 (1H, brs).

SIMS: m/z 538 (M$^+$+1).

(b) A 1 N aqueous sodium hydroxide solution (0.22 ml, 0.22 mmol) was added at room temperature to a solution of 1-(4-methoxybenzyl)-7-(2-(N-(2-methoxycarbonylphenyl) carbamoyl)-(E)-ethenyl)-4(5H),10-dioxo-1H-1,2,3-triazolo [4,5-c][1]benzazepine (54 mg, 0.10 mmol), prepared in the above step (a), in N,N-dimethylformamide (10 ml). The mixture was stirred at room temperature for one hr. Further, a 1 N aqueous sodium hydroxide solution (0.1 ml, 0.1 mmol) was added at room temperature thereto, followed by stirring at room temperature for 29 hr. The reaction mixture was made acidic by addition of a 1 N aqueous hydrochloric acid solution, the solvent was removed under reduced pressure, and the residue was washed with methanol and then dried to give 7-(2-(N-(2-carboxyphenyl)carbamoyl)-(E)-ethenyl)-1-(4-methoxybenzyl)-4(5H),10-dioxo-1H-1,2,3-triazolo[4,5-c][1]benzazepine.

Trifluoroacetic acid (4 ml) and anisole (1 ml) were then added to this compound, and the mixture was stirred at 70° C. for 10 min. The solvent was removed under reduced pressure. The resultant precipitate was washed with diethyl ether and dissolved in an aqueous sodium hydroxide solution, followed by purification on Diaion HP-20 (water:acetone=10:1) to give a sodium salt of the title compound: 7-(2-(N-(2-carboxyphenyl)carbamoyl)-(E)-ethenyl)-4(5H),10-dioxo-1H-1,2,3-triazolo[4,5-c][1]benzazepine as colorless powder (14.8 mg, 33.1%).

$^1$H-NMR (DMSO-d$_6$):δ 6.75 (1H, d), 6.95–7.00 (1H, m), 7.27–7.32 (1H, m), 7.46–7.53 (1H, m), 7.50 (1H, d), 7.79 (1H, s), 7.99–8.02 (1H, m), 8.29–8.32 (1H, m), 8.56–8.59 (1H, m), 10.65 (1H, brs).

Example 2

4(5H),10-Dioxo-7-(2-(N-(2-pyridyl)methyl)carbamoyl)ethyl-1H-1,2,3-triazolo[4,5-c][1]benzazepine (a) A 1 N aqueous sodium hydroxide solution (2 ml, 2 mmol) was added to a solution of 1-(4-methoxybenzyl)-7-(2-methoxycarbonyl)ethyl-4(5H),10-dioxo-1H-1,2,3-triazolo[4,5-c][1]benzazepine (223.4 mg, 0.534 mmol) in N,N-dimethylformamide (20 ml) described in Example 7 of International Publication WO 95/18130. The mixture was stirred at room temperature for 30 min. The reaction mixture was made acidic by addition of 1 N hydrochloric acid, the solvent was removed under reduced pressure, and the resultant precipitate was washed with ethyl acetate and then dried to give 7-(2-carboxy)ethyl-1-(4-methoxybenzyl)-4(5H),10-dioxo-1H-1,2,3-triazolo[4,5-c][1]benzazepine (168.3 mg, 75.3%).

$^1$H-NMR (DMSO-d$_6$): δ 2.58 (2H, t), 2.87 (2H, t), 3.70 (3H, s), 5.99 (2H, s), 6.89 (2H, d), 7.19 (1H, d), 7.27 (2H, d), 7.40 (1H, s), 8.09 (1H, d), 11.28 (1H, brs), 12.23 (1H, brs).

SIMS: m/z 406 (M$^+$).

(b) 2-(Aminomethyl)pyridine (38 μl, 0.369 mmol), 1-hydroxybenzotriazole (66 mg, 0.488 mmol), N-methylmorpholine (33 μl, 0.300 mmol), and 1-ethyl-3-(3-dimethylaminopropyl)carbodiimide hydrochloride (58 mg, 0.303 mmol) were added to a solution of 7-(2-carboxy)ethyl-1-(4-methoxybenzyl)-4(5H),10-dioxo-1H-1,2,3-triazolo[4,5-c][1]benzazepine (98 mg, 0.241 mmol), prepared in the above step (a), in N,N-dimethylformamide (10 ml). The mixture was stirred at room temperature for 14 hr, the solvent was removed under reduced pressure, and the resultant precipitate was washed with ethyl acetate and then dried to give 1-(4-methoxybenzyl)-4(5H),10-dioxo-7-(2-(N-(2-pyridyl)methyl)carbamoyl)ethyl-1H-1,2,3-triazolo[4,5-c][1]benzazepine (92 mg, 76.9%). $^1$H-NMR (DMSO-d$_6$): δ 2.5–2.55 (2H, m), 2.72–2.93 (2H, m), 3.70 (3H, s), 4.32 (2H, d), 6.01 (2H, s), 6.90 (2H, d), 7.06–7.09 (1H, m), 7.17–7.19 (2H, m), 7.28 (2H, d), 7.36 (1H, s), 7.55–7.60 (1H, s), 8.06–8.10 (1H, m), 8.42–8.48 (2H, m), 11.27 (1H, brs).

SIMS: m/z 497 (M$^+$+1).

(c) Trifluoroacetic acid (3 ml) was added to 1-(4-methoxybenzyl)-4(5H),10-dioxo-7-(2-(N-(2-pyridyl)methyl)carbamoyl)ethyl-1H-1,2,3-triazolo[4,5-c][1]benzazepine (92 mg, 0.185 mmol) prepared in the step (b), and the mixture was stirred at 70° C. for 10 min. The solvent was removed under reduced pressure, and the resultant precipitate was dried to give trifluoroacetate of the title compound:4(5H),10-dioxo-7-(2-(N-(2-pyridyl)methyl)carbamoyl)ethyl-1H-1,2,3-triazolo[4,5-c][1]benzazepine as yellow crystalline powder (62.1 mg, 68.4%).

$^1$H-NMR (DMSO-d$_6$): δ 2.56 (2H, t), 2.92 (2H, t), 4.41–4.43 (2H, m), 7.19–7.23 (1H, m), 7.31–7.34 (1H, m), 7.40–7.48 (1H, s), 7.42–7.45 (1H, m), 7.88–7.93 (1H, m), 8.20–8.23 (1H, m), 8.57–8.60 (2H, m), 11.33 (1H, brs).

SIMS: m/z 377 (M$^+$+1).

Compounds described in Examples 3 to 8 were synthesized in the same manner as in Example 2, except that the corresponding compound was used instead of 2-(aminomethyl)pyridine in Example 2 and, in addition, 7-(2-carboxy)ethyl-1-(4-methoxybenzyl)-4(5H),10-dioxo-1H-1,2,3-triazolo[4,5-c][1]benzazepine was used.

Example 3

4(5H),10-Dioxo-7-(2-(N-methyl-N-(2-pyridyl)methyl)carbamoyl)ethyl-1H-1,2,3-triazolo[4,5-c][1]benzazepine (a) 1-(4-Methoxybenzyl)-4(5H),10-dioxo-7-(2-(N-methyl-N-(2-pyridyl)methyl)carbamoyl)ethyl-1H-1,2,3-triazolo[4,5-c][1]benzazepine (43 mg, 69.9%)

$^1$H-NMR (DMSO-d$_6$): δ 2.7–3.0 (4H, m), 2.83 (6/5H, s), 3.02 (9/5H, s), 3.70 (6/5H, s), 3.71 (9/5H, s), 4.58 (6/5H, s), 4.64 (4/5H, s), 5.99 (4/5H, s), 6.00 (6/5H, s), 6.88–6.91 (2H, m), 7.12–7.41 (6H, m), 7.67–7.72 (3/5H, m), 7.72–7.77 (2/5H, m), 8.03–8.92 (1H, m), 8.45–8.50 (3/5H, m), 8.52–8.54 (2/5H, m), 11.23 (2/5H, brs), 11.27 (3/5H, brs).

EIMS: m/z 510 (M$^+$).

(b) Trifluoroacetate of the title compound: 4(5H),10-dioxo-7-(2-(N-methyl-N-(2-pyridyl)methyl)carbamoyl)ethyl-1H-1,2,3-triazolo[4,5-c][1]benzazepine (36.2 mg, 48.8%)

$^1$H-NMR (DMSO-d$_6$): δ 2.7–3.0 (4H, m), 2.84 (6/5H, s), 3.06 (9/5H, s), 4.64 (6/5H, s), 4.67 (4/5H, s), 7.2–7.5 (4H, m), 7.75–7.95 (1H, m), 8.1–8.3 (1H, m), 8.5–8.6 (1H, m), 11.28 (2/5H, brs), 11.32 (3/5H, brs).

SIMS: m/z 391 (M$^+$+1).

Example 4

7-(2-(N-Ethyl-N-(2-pyridyl)methyl)carbamoyl)ethyl-4(5H),10-dioxo-1H-1,2,3-triazolo[4,5-c][1]benzazepine (a) 7-(2-(N-Ethyl-N-(2-pyridyl)methyl)carbamoyl)ethyl-1-(4-methoxybenzyl)-4(5H),10-dioxo-1H-1,2,3-triazolo[4,5-c][1]benzazepine (67 mg, 54.1%)

$^1$H-NMR (DMSO-d$_6$): δ 0.96 (6/5H, t), 1.07 (9/5H, t), 2.68–2.96 (4H, m), 3.35–3.42 (2H, m), 3.70 (2/5H, s), 3.71 (3/5H, s), 4.55 (3/5H, s), 4.62 (2/5H, s), 5.99 (2/5H, s), 6.00 (3/5H, s), 6.90 (2H, d), 7.10–7.15 (2H, d), 7.20–7.30 (4H, m), 7.41 (3/5H, s), 7.34 (2/5H, s), 7.63–7.76 (1H, m), 8.03–8.10 (1H, m), 8.46–8.48 (3/5H, m), 8.51–8.54 (3/5H, m), 11.23 (2/5H, brs), 11.27 (3/5H, brs).

SIMS: m/z 525 (M$^+$+1).

(b) Trifluoroacetate of the title compound: 7-(2-(N-ethyl-N-(2-pyridyl)methyl)carbamoyl)ethyl-4(5H),10-dioxo-1H-1,2,3-triazolo[4,5-c][1]benzazepine (29.2 mg, 44.0%)

$^1$H-NMR (DMSO-d$_6$): δ 0.97, (6/5H, t), 1.11, (9/5H, t), 2.66–2.97, (4H, m), 3.32, (4/5H, q), 3.44, (6/5H, q), 4.64, (6/5H, s), 4.65, (4/5H, s), 6.95–7.49, (4H, m), 7.79–7.84, (2/5H, m), 7.92–7.97, (3/5H, m), 8.16–8.23, (1H, m), 8.56–8.61, (1H, m), 11.29, (2/5H, brs), 11.32, (3/5H, brs).

SIMS: m/z 405, (M$^+$+1).

Example 5

4(5H),10-Dioxo-7-(2-(N,N-bis(2-pyridylmethyl))carbamoyl)ethyl-1H-1,2,3-triazolo[4,5-c][1]benzazepine (a) 1-(4-Methoxybenzyl)-4(5H),10-dioxo-7-(2-(N,N-bis(2-pyridylmethyl))carbamoyl)ethyl-1H-1,2,3-triazolo[4,5-c][1]benzazepine (41.6 mg, 54.9%)

$^1$H-NMR (DMSO-d$_6$): δ 2.81–2.96 (4H, m), 3.70 (3H, s), 4.59 (2H, s), 4.72 (2H, s), 6.00 (2H, s), 6.90 (2H, d), 7.14–7.37 (8H, m), 7.28 (2H, d), 7.64–7.74 (2H, m), 8.04–8.07 (1H, m), 8.44–8.54 (2H, m), 11.24 (1H, s).

SIMS: m/z 588 (M$^+$+1).

(b) Ditrifluoroacetate of the title compound: 4(5H),10-dioxo-7-(2-(N,N-bis(2-pyridylmethyl))carbamoyl)ethyl-1H-1,2,3-triazolo[4,5-c][1]benzazepine (44.9 mg, 91.2%)

$^1$H-NMR (DMSO-d$_6$): δ 2.83–2.90 (4H, m), 4.71 (2H, s), 4.85 (2H, s), 6.81–6.84 (1H, s), 7.08–7.11 (1H, m), 7.15 (1H, d), 7.3–7.5 (3H, m), 7.82–7.87 (1H, m), 7.96–8.01 (1H, m), 8.17 (1H, d), 8.60–8.65 (2H, m), 11.29 (1H, brs).

SIMS: m/z 468 (M$^+$+1).

Example 6

7-(2-(1,2,3,4-Tetrahydro-2-isoquinolyl)carbonylethyl)-4(5H),10-dioxo-1H-1,2,3-triazolo[4,5-c][1]benzazepine (a) 7-(2-(1,2,3,4-Tetrahydro-2-isoquinolyl)carbonylethyl)-1-(4-methoxybenzyl)-4(5H),10-dioxo-1H-1,2,3-triazolo[4,5-c][1]benzazepine (98.8 mg, 75.8%)

$^1$H-NMR (DMSO-d$_6$): δ 2.68–2.96 (6H, m), 3.62–3.68 (2H, m), 3.71 (3H, s), 4.53 (8/9H, s), 4.59 (10/9H, s), 6.00 (2H, s), 6.87–7.40 (10H, m), 8.00–8.03 (4/9H, m), 8.06–8.09 (5/9H, m), 11.19 (4/9H, brs), 11.24 (5/9H, brs)

SIMS: m/z 522 (M$^+$+1).

(b) The title compound: 7-(2-(1,2,3,4-tetrahydro-2-isoquinolyl)carbonylethyl)-4(5H),10-dioxo-1H-1,2,3-triazolo[4,5-c][1]benzazepine (80.5 mg, quant.)

$^1$H-NMR (DMSO-d$_6$): δ 2.70–2.97 (6H, m), 3.4–3.8 (2H, m), 4.57 (8/9H, s), 4.60 (10/9H, s), 6.81–7.28 (5H, m), 7.44 (5/9H, s), 7.39 (4/9H, s), 8.13–8.22 (1H, m), 11.26 (4/9H, brs), 11.30 (5/9H, brs).

SIMS: m/z 402 (M$^+$+1).

Example 7

7-(2-(2-Methoxycarbonyl-4,5,6,7-tetrahydrothieno[3,2-c]pyridin-5-yl)carbonylethyl)-4(5H),10-dioxo-1H-1,2,3-triazolo[4,5-c][1]benzazepine (a) 1-Methoxybenzyl-7-(2-(2-methoxycarbonyl-4,5,6,7-tetrahydrothieno[3,2-c]pyridin-5-yl)carbonylethyl)-4(5H),10-dioxo-1H-1,2,3-triazolo[4,5-c][1]benzazepine (128.5 mg, 87.8%)

$^1$H-NMR (DMSO-d$_6$): δ 2.6–3.0 (6H, m), 3.1–3.3 (2H, s), 3.71 (3H, s), 3.72 (15/9H, s), 3.79 (12/9H, s), 4.45 (8/9H, s), 4.55 (10/9H, s), 5.99 (2H, s), 6.88–6.91 (2H, m), 7.15–7.63 (5H, m), 8.00–8.05 (4/9H, m), 8.06–8.09 (5/9H, m), 11.19 (4/9H, brs), 11.24 (5/9H, brs).

SIMS: m/z 586 (M$^+$+1).

(b) 7-(2-(2-Methoxycarbonyl-4,5,6,7-tetrahydrothieno[3,2-c]pyridin-5-yl)carbonylethyl)-4(5H),10-dioxo-1H-1,2,3-triazolo[4,5-c][1]benzazepine (94.1 mg, 92.3%)

$^1$H-NMR (DMSO-d$_6$): δ 2.71–2.97 (6H, m), 3.56–3.82 (2H, m), 3.79 (15/9H, s), 3.68 (12/9H, s), 4.39 (8/9H, s), 4.56 (10/9H, s), 7.19 (4/9H, m), 7.27 (5/9H, m), 7.31 (1H, s), 7.42 (4/9H, s), 7.63 (5/9H, s), 8.12 (4/9H, m), 7.21 (5/9H, m), 11.28 (1H, brs).

SIMS: m/z 466 (M$^+$+1).

Example 8

7-(2-(4-Methylpiperazin-1-yl)carbonylethyl)-4(5H),10-dioxo-1H-1,2,3-triazolo[4,5-c][1]benzazepine (a) 1-(4-Methoxybenzyl)-7-(2-(4-Methylpiperazin-1-yl)carbonylethyl)-4(5H),10-dioxo-1H-1,2,3-triazolo[4,5-c][1]benzazepine (91.3 mg, 77.2%).

$^1$H-NMR (DMSO-d$_6$): δ 2.2–2.3 (4H, m), 2.85 (2H, t), 2.66 (2H, t), 3.3–3.5 (4H, m), 3.34 (3H, s), 6.00 (2H, s), 6.90 (2H, d), 7.20 (1H, d), 7.27 (2H, d), 7.37 (1H, s), 8.07 (1H, d), 11.28 (1H, brs).

SIMS: m/z 489 (M$^+$+1).

(b) Trifluoroacetate of the title compound: 7-(2-(4-methylpiperazin-1-yl)carbonylethyl)-4(5H),10-dioxo-1H-1,2,3-triazolo[4,5-c][1]benzazepine (85.4 mg, 94.7%)

$^1$H-NMR (DMSO-d$_6$): δ 2.74 (2H, t), 2.88 (2H, t), 3.1–3.9 (8H, m), 7.24 (1H, d), 7.42 (1H, s), 8.22 (1H, d), 11.31 (1H, brs).

SIMS: m/z 369 (M$^+$+1).

Example 9

7-(2-(N-(4-Pyridylamino))carbamoyl)ethyl-4(5H),10-dioxo-1H-1,2,3-triazolo[4,5-c][1]benzazepine (a) Tributylamine (44 μl, 0.185 mmol), 2-chloro-1-methylpyridinium p-toluenesulfonate (61 mg, 0.203 mmol), 3,4-dihydro-2H-pyrido[1,2-a]pyrimidin-2-one (30 mg, 0.202 mmol), and 4-aminopyridine (24 mg, 0.255 mmol) were added in that order to a solution of 7-(2-hydroxycarbonyl)ethyl-1-(4-methoxybenzyl)-4(5H),10-dioxo-1H-1,2,3-triazolo[4,5-c][1]benzazepine (48 mg, 0.118 mmol), prepared in the step (b) of Example 2, in N,N-dimethylformamide (5 ml), and the mixture was stirred at room temperature for 34 hr. The solvent was removed under reduced pressure, and the resultant precipitate was washed with methanol to give 1-(4-methoxybenzyl)-7-(2-(N-(4-pyridylamino))carbamoyl)ethyl-4(5H),10-dioxo-1H-1,2,3-triazolo[4,5-c][1]benzazepine (51 mg, 89.6%).

$^1$H-NMR (DMSO-d$_6$): δ 2.73 (2H, t), 2.97 (2H, t), 3.71 (3H, s), 5.99 (2H, s), 6.89 (2H, d), 7.21 (1H, d), 7.27 (2H, d), 7.39 (1H, s), 7.53 (2H, d), 8.10 (1H, d), 8.40 (2H, d), 10.36 (1H, brs), 11.31 (1H, brs).

SIMS: m/z 483 (M$^+$+1).

(b) Anisole (1 ml) and trifluoroacetic acid (4 ml) were added to 1-(4-methoxybenzyl)-7-(2-(N-(4-pyridylamino))carbamoyl)ethyl-4(5H),10-dioxo-1H-1,2,3-triazolo[4,5-c][1]benzazepine (98 mg, 0.203 mmol), prepared in the step (a), and the mixture was stirred at 70° C. for 10 min. The solvent was removed under reduced pressure, and the resultant precipitate was washed with diisopropyl ether to give trifluoroacetate of the title compound: 7-(2-(N-(4-Pyridylamino))carbamoyl)ethyl-4(5H), 10-dioxo-1H-1,2,3-triazolo[4,5-c][1]benzazepine as yellow crystalline powder (97 mg, quant.)

$^1$H-NMR (DMSO-d$_6$): δ 2.87 (2H, t), 3.01 (2H, t), 7.25 (1H, d), 7.43 (1H, s), 7.96 (2H, d), 8.24 (1H, d), 8.65 (2H, d), 11.26 (1H, brs), 11.37 (1H, brs).

SIMS: m/z 363 (M$^+$+1).

Example 10

4(5H),10-Dioxo-7-(2-(4-pyridyl)-(E)-ethenyl)-1H-1,2,3-triazolo[4,5-c][1]benzazepine trifluoroacetate (a) 4-Picolyltriphenylphosphonium chloride hydrochloride (162 mg, 0.38 mmol) was suspended in toluene (5 ml) under an argon atmosphere, and potassium tert-butoxide (86 mg, 0.77 mmol) was added to the suspension. 7-Formyl-1-(4-methoxybenzyl)-4(5H),10-dioxo-1H-1,2,3-triazolo[4,5-c][1]benzazepine (114.7 mg, 0.32 mmol) was then added, followed by stirring at 70° C. for 4 hr 20 min. Water was added to the reaction mixture, and the resultant brown crystalline powder was then collected by filtration, washed with diethyl ether, and dried to give 1-(4-methoxybenzyl)-4(5H),10-dioxo-7-(2-(4-pyridyl)-(E)-ethenyl)-1H-1,2,3-triazolo[4,5-c][1]benzazepine (81.1 mg, 59%).

$^1$H-NMR (DMSO-d$_6$): δ 3.71 (3H, s), 6.00 (2H, s), 6.91 (2H, d), 7.30 (2H, d), 7.40 (1H, d), 7.55 (1H, d), 7.60–7.75 (4H, m), 8.20 (1H, d), 8.60 (2H, d), 11.40 (1H, s).

EIMS: m/z 437 (M$^+$).

(b) 1-(4-Methoxybenzyl)-4(5H),10-dioxo-7-(2-(4-pyridyl)-(E)-ethenyl)-1H-1,2,3-triazolo[4,5-c][1]benzazepine (81.1 mg, 0.19 mmol) prepared in the above step (a) was dissolved in anisole (0.2 ml) and trifluoroacetic acid (2 ml), and the solution was heated at 60° C. for 20 min. The solvent was removed under reduced pressure, and the resultant crystal was collected by filtration, washed with diethyl ether, and dried to give the title compound: 4(5H), 10-dioxo-7-(2-(4-pyridyl)-(E)-ethenyl)-1H-1,2,3-triazolo[4,5-c][1]benzazepine trifluoroacetate as yellow crystalline powder (72.7 mg, 91,%.).

$^1$H-NMR (DMSO-d$_6$): δ 7.54 (1H, d), 7.72 (1H, d), 7.77 (1H, s), 7.79 (1H, d), 8.03 (2H, d), 8.35 (1H, d), 8.78 (2H, d), 11.53 (1H, s).

SIMS: m/z 318 (M++1).

Example 11

4(5H),10-Dioxo-7-(2-(2-pyridyl)-(E)-ethenyl)-1H-1,2,3-triazolo[4,5-c][1]benzazepine trifluoroacetate (a) 2-Picolyltriphenylphosphonium chloride hydrochloride (209 mg, 0.49 mmol) was suspended in toluene (5 ml) and N,N-dimethylformamide (2 ml) under an argon atmosphere, and potassium tert-butoxide (110 mg, 0.98 mmol) was added to the suspension. 7-Formyl-1-(4-methoxybenzyl)-4(5H),10-dioxo-1H-1,2,3-triazolo[4,5-c][1]benzazepine (150 mg, 0.41 mmol) was then added, followed by stirring at 70° C. for 7.5 hr. Water was added to the reaction mixture, and the resultant yellow crystalline powder was then collected by filtration, washed with diethyl ether, and dried to give 1-(4-methoxybenzyl)-4(5H),10-dioxo-7-(2-(2-pyridyl)-(E)-ethenyl)-1H-1,2,3-triazolo[4,5-c][1]benzazepine (102.9 mg, 57%).

$^1$H-NMR (DMSO-d$_6$): δ 3.71 (3H, s), 6.01 (2H, s), 6.91 (2H, d), 7.30 (2H, d), 7.34 (1H, dd), 7.47 (1H, d), 7.60–7.74 (4H, m), 7.84 (1H, t), 8.19 (1H, d), 8.62 (1H, d), 11.38 (1H, s).

SIMS: m/z 438 (M$^+$+1).

(b) 1-(4-methoxybenzyl)-4(5H),10-dioxo-7-(2-(2-pyridyl)-(E)-ethenyl)-1H-1,2,3-triazolo[4,5-c][1]benzazepine (97.9 mg, 0.22 mmol) prepared in the above step (a) was dissolved in anisole (0.2 ml) and trifluoroacetic acid (2 ml), and the solution was heated at 60° C. for 15 min. The solvent was removed under reduced pressure, and the resultant crystal was collected by filtration, washed with diethyl ether, and dried to give the title compound: 4(5H), 10-dioxo-7-(2-(2-pyridyl)-(E)-ethenyl)-1H-1,2,3-triazolo[4, 5-c][1]benzazepine trifluoroacetate as yellow crystalline powder (80.3 mg, 83%).

$^1$H-NMR (DMSO-d$_6$): δ 7.42–7.50 (1H, m), 7.49 (1H, d), 7.66–7.84 (3H, m), 7.72 (1H, d), 7.98 (1H, t), 8.33 (1H, d), 8.68 (1H, d), 11.47 (1H, s).

SIMS: m/z 318 (M$^+$+1).

Example 12

7-(3-Morpholinopropoxy)-4(5H),10-dioxo-1H-1,2,3-triazolo[4,5-c][1]benzazepine trifluoroacetate (a) 7-(3-Chloropropoxy)-1-(4-methoxybenzyl)-4(5H),10-dioxo-1H-1,2,3-triazolo[4,5-c][1]benzazepine (100 mg, 0.234 mmol) described in the step (a) of Example 71 in International Publication WO 95/18130 was dissolved in N,N-dimethylformamide (2 ml). Morpholine (0.10 ml, 1.15 mmol) and sodium iodide (105 mg, 0.701 mmol) were added to the solution, and the mixture was stirred at 60° C. for three days. Water was added to the reaction mixture, and the resultant crystal was collected by filtration and dried to give 1-(4-methoxybenzyl)-7-(3-morpholinopropoxy)-4(5H),10-dioxo-1H-1,2,3-triazolo[4,5-c][1]benzazepine (102 mg, 91%).

$^1$H-NMR (DMSO-D$_6$): δ 1.91 (2H, quintet), 2.30–2.45 (4H, m), 2.41 (2H, t), 3.56 (4H, t), 3.71 (3H, s), 4.10 (2H, t), 6.00 (2H, s), 6.89 (2H, d), 6.90 (1H, dd), 7.05 (1H, d), 7.27 (2H, d), 8.13 (1H, d), 11.20 (1H, s).

SIMS: m/z 478 (M$^+$+1).

(b) 1-(4-Methoxybenzyl)-7-(3-morpholinopropoxy)-4(5H),10-dioxo-1H-1,2,3-triazolo[4,5-c][1]benzazepine (89 mg, 0.186 mmol) prepared in the step (a) was treated with anisole (0.2 ml) and trifluoroacetic acid (2.0 ml) in the same manner as in step (b) of Example 1. Diethyl ether was added to the residue, and the resultant crystal as a precipitate was collected by filtration and then dried to give the title compound: 7-(3-morpholinopropoxy)-4(5H),10-dioxo-1H-1,2, 3-triazolo[4,5-c] [1]benzazepine trifluoroacetate (77 mg, 88%).

$^1$H-NMR (D$_2$O): δ 2.10–2.28 (2H, m), 3.15–3.30 (2H, m), 3.39 (2H, t), 3.65 (2H, d), 3.70–3.90 (4H, m), 4.14 (2H, d), 6.05 (1H, s), 6.14 (1H, d), 7.55 (1H, d).

SIMS: m/z 358 (M$^+$—CF$_3$COOH+1).

Example 13

7-(3-(4-Methyl-1-piperazino)propoxy)-4(5H),10-dioxo-1H-1,2,3-triazolo[4,5-c][1]benzazepine ditrifluoroacetate (a) 7-(3-Chloropropoxy)-1-(4-methoxybenzyl)-4(5H),10-dioxo-1H-1,2,3-triazolo[4,5-c][1]benzazepine (150 mg, 0.351 mmol) described in the step (a) of Example 71 in International Publication WO 95/18130 was dissolved in N,N-dimethylformamide (4 ml). N-Methylpiperazine (0.20 ml, 1.80 mmol), sodium iodide (157 mg, 1.05 mmol), and potassium carbonate (243 mg, 1.76 mmol) were added to the solution, and the mixture was stirred at 60° C. for 16 hr, followed by post treatment in the same manner as in the step (a) of Example 12 to give 1-(4-methoxybenzyl)-7-(3-(4-methyl-1-piperazino)propoxy)-4(5H), 10-dioxo-1H-1,2,3-triazolo[4,5-c][1]benzazepine as yellow powder (152 mg, 88%).

$^1$H-NMR (DMSO-d$_6$):δ 1.89 (2H, quintet), 2.10–2.60 (8H, m), 2.13 (3H, s), 2.40 (2H, t), 3.71 (3H, s), 4.08 (2H, d), 6.00 (2H, s), 6.89 (2H, d), 7.04 (1H, d), 7.27 (2H, d), 8.13 (1H, d), 11.21 (1H, brs).

SIMS: m/z 491 (M$^+$+1).

(b) 1-(4-Methoxybenzyl)-7-(3-(4-methyl-1-piperazino) propoxy)-4(5H),10-dioxo-1H-1,2,3-triazolo[4,5c][1] benzazepine (137 mg, 0.279 mmol) prepared in the step (a) was subjected to deprotection and post treatment using anisole (0.3 ml) and trifluoroacetic acid (3.0 ml) in the same manner as in step (b) of Example 1. Diethyl ether was added to the residue, and the resultant crystal as a precipitate was collected by filtration and then dried to give the title compound: 7-(3-(4-methyl-1-piperazino)propoxy)-4(5H),10-dioxo-1H-1,2,3-triazolo[4,5-c][1]benzazepine ditrifluoroacetate (126 mg, 75%).

$^1$H-NMR (D$_2$O):δ 2.20–2.32 (2H, m), 3.02 (3H, s), 3.56 (2H, t), 3.63–3.90 (8H, m), 3.92 (2H, t), 6.19 (1H, s), 6.25 (1H, d), 7.69 (1H, d).

SIMS: m/z 371 (M$^+$—2CF$_3$COOH+1).

Example 14

7-(3-(4-Benzylpiperidino)propoxy)-4(5H),10-dioxo-1H-1, 2,3-triazolo[4,5-c][1]benzazepine trifluoroacetate (a) 7-(3-Chloropropoxy)-1-(4-methoxybenzyl)-4(5H),10-dioxo-1H-1,2,3-triazolo[4,5-c][1]benzazepine (100 mg, 0.234 mmol) described in the step (a) of Example 71 in International Publication WO 95/18130 was dissolved in N,N-dimethylformamide (2 ml). 4-Benzylpiperidine (0.21 ml, 1.19 mmol) and sodium iodide (105 mg, 0.701 mmol) were added to the solution, followed by a reaction and work up in the same manner as in Example 12 to give 7-(3-(4-benzylpiperidino)propoxy)-1-(4-methoxybenzyl)-4(5H),10-dioxo-1H-1,2,3-triazolo[4,5-c][1]benzazepine (118 mg, 89%).

$^1$H-NMR (DMSO-d$_6$):δ 1.10–1.25 (2H, m), 1.40–1.60 (3H, m), 1.75–1.94 (4H, m), 2.37 (2H, t), 2.43–2.56 (2H, m), 2.82 (2H, d), 3.71 (3H, s), 4.08 (2H, t), 6.01 (2H, s), 6.89 (2H, d), 6.90 (1H, dd), 7.05 (1H, d), 7.11–7.20 (3H, m), 7.20–7.32 (4H, m), 8.14 (1H, d), 11.21 (1H, s).

EIMS: m/z 565 (M+).

(b) 7-(3-(4-benzylpiperidino)propoxy)-1-(4-methoxybenzyl)-4(5H),10-dioxo-1H-1,2,3-triazolo[4,5-c][1]benzazepine (110 mg, 0.194 mmol) prepared in the step (a) was subjected to deprotection and post treatment using anisole (0.2 ml) and trifluoroacetic acid (2.0 ml) in the same manner as in step (b) of Example 1. Diethyl ether was added to the residue, and the resultant crystal as a precipitate was collected by filtration and then dried to give the title compound: 7-(3-(4-benzylpiperidino)propoxy)-4(5H),10-dioxo-1H-1,2,3-triazolo[4,5-c][1]benzazepine trifluoroacetate (91 mg, 84%).

$^1$H-NMR (DMSO-d$_6$):δ 1.35–1.55 (2H, m), 1.72–1.90 (3H, m), 2.10–2.23 (2H, m), 2.50–2.60 (2H, m), 2.80–3.05 (2H, m), 3.15–3.60 (4H, m), 4.12 (2H, t), 6.85 (1H, dd), 7.01 (1H, d), 7.21–7.30 (3H, m), 7.30–7.40 (2H, m), 8.22 (1H, d), 11.10 (1H, s).

SIMS: m/z 446 (M+—CF$_3$COOH+1).

Example 15
7-(N-Ethyl-N-(2-pyridylmethyl)carbamoylmethyloxy)-4(5H),10-dioxo-1H-1,2,3-triazolo[4,5-c][1]benzazepine trifluoroacetate (a) 7-Carboxymethoxy-1-(4-methoxybenzyl)-4(5H),10-dioxo-1H-1,2,3-triazolo[4,5-c][1]benzazepine (100 mg, 0.245 mmol) described in the step (a) of Example 23 in International Publication WO 95/18130 was dissolved in N,N-dimethylformamide (2.0 ml). A solution of benzotriazol-1-yloxytris(dimethylamino)phosphonium hexafluorophosphate (119 mg, 0.269 mmol), N-methylmorpholine (0.03 ml, 0.273 mmol), and N-ethyl-2-picolylamine (37 mg, 0.272 mmol) in N,N-dimethylformamide (1 ml) was added to the above solution, and the mixture was stirred at room temperature for 30 min. Water was added to the reaction mixture, and the resultant crystal as a precipitate was collected by filtration and dried to give 7-(N-ethyl-N-(2-pyridylmethyl)carbamoylmethyloxy)-1-(4-methoxybenzyl)-4(5H),10-dioxo-1H-1,2,3-triazolo[4,5-c] [1]benzazepine (110 mg, 85%).

$^1$H-NMR (DMSO-d$_6$): δ 0.96 (3/2H, t), 1.19 (3/2H, t), 3.25–3.48 (2H, m), 3.71 (3H, s), 4.59 (1H, s), 4.66 (1H, s), 5.12 (2H, s), 6.01 (2H, s), 6.89 (2H, d), 6.90–7.08 (2H, m), 7.27 (2H, d), 7.30–7.47 (2H, m), 7.73 (1/2H, t), 7.83 (1/2H, t), 8.15 (1/2H, d), 8.16 (1/2H, d), 8.50 (1/2H, d), 8.63 (1/2H, d), 11.25 (1/2H, s), 11.26 (1/2H, s).

SIMS: m/z 527 (M++1).

(b) 7-(N-Ethyl-N-(2-pyridylmethyl)carbamoylmethyloxy)-1-(4-methoxybenzyl)-4(5H),10-dioxo-1H-1,2,3-triazolo[4,5-c][1]benzazepine (105 mg, 0.199 mmol) prepared in the step (a) was subjected to deprotection and post treatment using anisole (0.2 ml) and trifluoroacetic acid (2.0 ml) in the same manner as in step (b) of Example 1 to give the title compound:7-(N-ethyl-N-(2-pyridylmethyl)carbamoylmethyloxy)-4(5H),10-dioxo-1H-1,2,3-triazolo[4,5-c][1]benzazepine trifluoroacetate (99 mg, 96%).

$^1$H-NMR (DMSO-d$_6$): δ 0.98 (6/5H, t), 1.23 (9/5H, t), 3.30 (4/5H, q), 3.48 (6/5H, q), 4.69 (2H, s), 5.12 (4/5H, s), 5.15 (6/5H, s), 6.90–7.13 (2H, m), 7.30–7.60 (2H, m), 7.90 (2/5H, dt), 8.05 (3/5H, t), 8.22–8.32 (1H, m), 8.60–8.70 (1H, m), 11.30 (2/5H, s), 11.31 (3/5H, s).

SIMS: m/z 407 (M+—CF$_3$COOH+1).

Example 16
4(5H),10-Dioxo-7-(N-(2-pyridylmethyl)carbamoylmethyloxy)-1H-1,2,3-triazolo[4,5-c][1]benzazepine trifluoroacetate (a) 7-Carboxymethoxy-1-(4-methoxybenzyl)-4(5H),10-dioxo-1H-1,2,3-triazolo[4,5-c][1]benzazepine (100 mg, 0.245 mmol) described in the step (a) of Example 23 in International Publication WO 95/18130 was dissolved in N,N-dimethylformamide (2.0 ml). Benzotriazol-1-yloxytris(dimethylamino)phosphonium hexafluorophosphate (119 mg, 0.269 mmol), N-methylmorpholine (0.03 ml, 0.273 mmol), and 2-picolylamine (0.028 ml, 0.272 mmol) were added to the solution, and the mixture was stirred at room temperature for 45 min. Water was added to the reaction mixture, and the resultant crystal as a precipitate was collected by filtration and dried to give 1-(4-methoxybenzyl)-4(5H), 10-dioxo-7-(N-(2-pyridylmethyl)carbamoylmethyloxy)-1H-1,2,3-triazolo[4,5-c][1]benzazepine (115 mg, 94%).

$^1$H-NMR (DMSO-d$_6$): δ 3.71 (3H, s), 4.44 (2H, d), 4.72 (2H, s), 6.01 (2H, s), 6.90 (2H, d), 6.97 (1H, dd), 7.10 (1H, d), 7.20–7.40 (4H, m), 7.72 (1H, t), 8.17 (1H, d), 8.49 (1H, d), 8.77 (1H, t), 11.30 (1H, s).

SIMS: m/z 499 (M +1).

(b) 1-(4-Methoxybenzyl)-4(5H),10-dioxo-7-(N-(2-pyridylmethyl)carbamoylmethyloxy)-1H-1,2,3-triazolo[4,5-c][1]benzazepine (164 mg, 0.329 mmol) prepared in the step (a) was subjected to deprotection and post treatment using anisole (0.3 ml) and trifluoroacetic acid (3.0 ml) in the same manner as in step (b) of Example 1 to give the title compound: 4(5H),10-dioxo-7-(N-(2-pyridylmethyl)carbamoylmethyloxy)-1H-1,2,3-triazolo[4,5-c][1]benzazepine trifluoroacetate (161 mg, 99%).

$^1$H-NMR (DMSO-d$_6$): δ 4.46 (2H, d), 4.73 (2H, s), 7.00 (1H, d), 7.14 (1H, s), 7.29 (1H, t), 7.33 (1H, d), 7.77 (1H, t), 8.29 (1H, d), 8.51 (1H, d), 8.80 (1H, t), 11.34 (1H, s).

SIMS: m/z 379 (M+—CF$_3$COOH+1).

Example 17
4(5H),10-Dioxo-7-(4-toluoyloxy)-1H-1,2,3-triazolo[4,5-c][1]benzazepine (a) 7-Hydroxy-1-(4-methoxybenzyl)-4(5H),10-dioxo-1H-1,2,3-triazolo[4,5-c][1]benzazepine (50 mg, 0.143 mmol) described in the step (a) of Example 23 in International Publication WO 95/18130 was dissolved in N,N-dimethylformamide (2 ml). Potassium carbonate (30 mg, 0.217 mmol) and 4-toluoyl chloride (0.03 ml, 0.227 mmol) were added to the solution, and the mixture was stirred at room temperature overnight. Further, potassium carbonate (15 mg, 0.109 mmol) and 4-toluoyl chloride (0.015 ml, 0.114 mmol) were added to the reaction mixture which was stirred for 3 hr, and excess water was added to the reaction mixture. The resultant precipitate was collected by filtration and dried to give 1-(4-methoxybenzyl)-4(5H),10-dioxo-7-(4-toluoyloxy)-1H-1,2,3-triazolo[4,5-c][1]benzazepine (59 mg, 88%).

$^1$H-NMR (DMSO-d$_6$): δ 2.43 (3H, s), 3.71 (3H, s), 6.00 (2H, s), 6.91 (2H, d), 7.27 (1H, dd), 7.30 (2H, d), 7.41 (1H, d), 7.44 (2H, d), 8.04 (2H, d), 8.27 (1H, d), 11.43 (1H, s).

SIMS: m/z 469 (M++1).

(b) Anisole (0.1 ml) and trifluoroacetic acid (1.0 ml) were added to 1-(4-methoxybenzyl)-4(5H),10-dioxo-7-(4-toluoyloxy)-1H-1,2,3-triazolo[4,5-c] [1]benzazepine (56 mg, 0.120 mmol) prepared in the step (a), and the reaction mixture was subjected to work up in the same manner as in the step (b) of Example 1 to give the title compound: 4(5H),10-dioxo-7-(4-toluoyloxy)-1H-1,2,3-triazolo[4,5-c][1]benzazepine (40 mg, 96%).

$^1$H-NMR (DMSO-d$_6$): δ 2.44 (3H, s), 3.50 (1H, brs), 7.30 (1H, dd), 7.42–7.50 (3H, m), 8.05 (2H, d), 8.39 (1H, d), 11.50 (1H, s).

EIMS: m/z 348 (M +).

Example 18
7-(N,N-Bis(2-pyridylmethyl)carbamoylmethyloxy)-4(5H), 10-dioxo-1H-1,2,3-triazolo[4,5-c][1]benzazepine ditrifluoroacetate (a) 7-Carboxymethoxy-1-(4-methoxybenzyl)-4(5H),10-dioxo-1H-1,2,3-triazolo[4,5-c][1]benzazepine (100 mg, 0.245 mmol) described in the step (a) of Example 23 in International Publication WO 95/18130 was dissolved in N,N-dimethylformamide (2.0 ml). A solution of benzotriazol-1-yloxytris(dimethylamino)phosphonium hexafluorophosphate (119 mg, 0.269 mmol), N-methylmorpholine (0.03 ml, 0.273 mmol), and N,N-bis-(2-picolyl)amine (54 mg, 0.271 mmol) in N,N-dimethylformamide (1 ml) was added to the above solution, and the mixture was stirred at room temperature for 40 min. Water was added to the reaction mixture, and the resultant crystal as a precipitate was collected by filtration and dried to give 7-(N,N-bis(2-pyridylmethyl)carbamoylmethyloxy)-1-(4-methoxybenzyl)-4(5H),10-dioxo-1H-1,2,3-triazolo[4,5-c][1]benzazepine (113 mg, 78%).

$^1$H-NMR (DMSO-$d_6$): δ 3.70 (3H, s), 4.55 (2H, s), 4.75 (2H, s), 5.29 (2H, s), 6.01 (2H, s), 6.89 (2H, d), 7.00–7.08 (2H, m), 7.22–7.30 (2H, m), 7.27 (2H, d), 7.32–7.37 (1H, m), 7.39 (1H, d), 7.71 (1H, dt), 7.80 (1H, dt), 8.17 (1H, d), 8.47 (1H, d), 8.64 (1H, d), 11.26 (1H, s).

SIMS: m/z 590 ($M^+$+1).

(b) 7-(N,N-bis(2-pyridylmethyl)carbamoylmethyloxy)-1-(4-methoxybenzyl)-4(5H),10-dioxo-1H-1,2,3-triazolo[4,5c][1]benzazepine (135 mg, 0.229 mmol) prepared in the step (a) was subjected to deprotection using anisole (0.2 ml) and trifluoroacetic acid (2.0 ml) in the same manner as in step (b) of Example 1 to give the title compound: 7-(N,N-bis(2-pyridylmethyl)carbamoylmethyloxy)-4(5H), 10-dioxo-1H-1,2,3-triazolo[4,5-c][1]benzazepine ditrifluoroacetate (141 mg, 88%).

$^1$H-NMR (DMSO-$d_6$): δ 4.69 (2H, s), 4.87 (2H, s), 5.25 (2H, s), 7.00 (1H, dd), 7.07 (1H, d), 7.40–7.60 (4H, m), 7.89 (1H, t), 8.03 (1H, t), 8.28 (1H, d), 8.70 (1H, d), 8.65 (1H, d), 11.29 (1H, s).

SIMS: m/z 470 ($M^+$—2$CF_3COOH$+1).

Example 19
7-(N-Methyl-N-(2-pyridylmethyl)carbamoylmethyloxy)-4(5H),10-dioxo-1H-1,2,3-triazolo[4,5-c][1]benzazepine trifluoroacetate (a) 7-Carboxymethoxy-1-(4-methoxybenzyl)-4(5H),10-dioxo-1H-1,2,3-triazolo[4,5-c][1]benzazepine (100 mg, 0.245 mmol) described in the step (a) of Example 23 in International Publication WO 95/18130 was dissolved in N,N-dimethylformamide (2.0 ml). A solution of benzotriazol-1-yloxytris(dimethylamino)phosphonium hexafluorophosphate (119 mg, 0.269 mmol), N-methylmorpholine (0.03 ml, 0.273 mmol), and N-methyl-2-picolylamine (33 mg, 0.270 mmol) in N,N-dimethylformamide (1 ml) was added to the above solution, and the mixture was stirred at room temperature for 30 min. Water was added to the reaction mixture, and the resultant crystal as a precipitate was collected by filtration and dried to give 1-(4-methoxybenzyl)-7-(N-methyl-N-(2-pyridylmethyl)carbamoylmethyloxy)-4(5H),10-dioxo-1H-1,2,3-triazolo[4,5-c][1]benzazepine (111 mg, 88%).

$^1$H-NMR (DMSO-$d_6$): δ 2.82 (6/5H, s), 3.08 (9/5H, s), 4.61 (6/5H, s), 4.66 (4/5H, s), 5.11 (6/5H, s), 5.13 (4/5H, s), 6.00 (2H, s), 6.89 (2H, d), 6.92–6.99 (1H, m), 6.99–7.07 (1H, m), 7.27 (2H, d), 7.32–7.38 (1H, m), 7.41 (1H, d), 7.76 (3/5H, t), 7.84 (2/5H, t), 8.14 (3/5H, d), 8.15 (2/5H, d), 8.51 (3/5H, d), 8.63 (2/5H, d), 11.24 (1H, s).

SIMS: m/z 513 ($M^+$+1).

(b) 1-(4-Methoxybenzyl)-7-(N-methyl-N-(2-pyridylmethyl )carbamoylmethyloxy)-4(5H), 10-dioxo-1H-1,2,3-triazolo[4,5-c] [1]benzazepine (149 mg, 0.291 mmol) prepared in the step (a) was subjected to deprotection using anisole (0.3 ml) and trifluoroacetic acid (3.0 ml) in the same manner as in step (b) of Example 1 to give the title compound: 7-(N-methyl-N-(2-pyridylmethyl)carbamoylmethyloxy)-4(5H),10-dioxo-1H-1,2,3-triazolo[4,5-c][1]benzazepine trifluoroacetate (130 mg, 88%).

$^1$H-NMR (DMSO-$d_6$): δ 2.83 (1H, s), 3.13 (2H, s), 4.71 (2H, s), 5.13 (2H, s), 6.98 (1H, dd), 7.06 (1H, d), 7.39–7.57 (2H, m), 7.90 (1/3, t), 8.04 (2/3H, t), 8.25 (1/3H, d), 8.27 (2/3H, d), 8.62–8.70 (1H, m), 11.27 (1H, s).

SIMS: m/z 393 ($M^+$—$CF_3COOH$+1).

Example 20
7-Amino-4(5H),10-dioxo-1H-1,2,3-triazolo[4,5c][1]benzazepine (a) A 1.0 M solution (9.49 ml) of lithium bistrimethylsilylamide in tetrahydrofuran was added to tetrahydrofuran (20.0 ml) at −78° C. under an argon atmosphere, and the mixture was stirred for 30 min. A solution of ethyl propiolate (0.78 ml, 8.62 mmol) in tetrahydrofuran (2.0 ml) was added thereto, and the mixture was stirred for 30 min. A solution of 4-t-butoxycarbonylamino-2-nitrobenzaldehyde (1.53 g, 5.75 mmol) in tetrahydrofuran (20 ml) was then added thereto, and the temperature was raised to −60° C., followed by stirring for 30 min. This reaction mixture was poured into an ice-cold 10% aqueous ammonium chloride solution, and the mixture was vigorously stirred for 5 min. The reaction mixture was extracted with ethyl acetate, and the organic layer was washed with saturated brine and dried over anhydrous magnesium sulfate. The solvent was removed under reduced pressure to give ethyl 4-(4-t-butoxycarbonylamino-2-nitrophenyl)-4-hydroxy-2-butynoate as an oil (693 mg, 33%).

$^1$H-NMR (CDCl$_3$): δ 1.30 (3H, t), 1.53 (9H, s), 3.55 (1H, d), 4.24 (2H, q), 6.07 (1H, d), 6.92 (1H, s), 7.58 (1H, dd), 7.77 (1H, d), 8.20 (1H, d).

SIMS: m/z 365 ($M^+$+1).

(b) Ethyl 4-(4-t-butoxycarbonylamino-2-nitrophenyl)-4-hydroxy-2-butynoate (693 mg, 1.90 mmol) prepared in the step (a) and 4-methoxybenzylazide (776 mg, 4.76 mmol) were dissolved in toluene (30 ml), and the solution was stirred at 100° C. overnight. The solvent was removed under reduced pressure, and the residue was purified by chromatography on silica gel (n-hexane:ethyl acetate=1:1) to give a 1:1 mixture (1.33 g) of ethyl 4-((4-t-butoxycarbonylamino-2-nitrophenyl)hydroxymethyl)-1-(4-methoxybenzyl)-1,2,3-triazole-5-carboxylate and ethyl 5-((4-t-butoxycarbonylamino-2-nitrophenyl)hydroxymethyl)-1-(4-methoxybenzyl)-1,2,3-triazole-4-carboxylate. This mixture (1.33 g) was dissolved in methylene chloride (30 ml), active manganese dioxide (3.5 g) was added to the solution, and the mixture was stirred for 30 min. Manganese dioxide was filtered off through Celite, the filtrate was concentrated under reduced pressure, and the residue was purified by chromatography on silica gel (n-hexane:ethyl acetate=2:1) to give a 1:1 mixture (872 mg, 87%) of ethyl 4-(4-t-butoxycarbonylamino-2-nitrobenzoyl)-1-(4-methoxybenzyl)-1,2,3-triazole-5-carboxylate and ethyl 5-(4-t-butoxycarbonylamino-2-nitrobenzoyl)-1-(4-methoxybenzyl)-1,2,3-triazole-4-carboxylate.

$^1$H-NMR (CDCl$_3$): δ 1.15 (3/2H, t), 1.34 (3/2H, t), 1.51 (9H, s), 3.75 (3/2H, s), 3.78 (3/2H, s), 4.12 (1H, q), 4.39 (1H, q), 5.71 (2H, d), 6.83 (2H, m), 7.18–7.72 (5H, m), 8.10 (1/2H, d), 8.19 (1/2H, d).

FDMS: m/z 525 ($M^+$).

(c) To a solution of the 1:1 mixture (872 mg) of ethyl 4-(4-t-butoxycarbonylamino-2-nitrobenzoyl)-1-(4-methoxybenzyl)-1,2,3-triazole-5-carboxylate and ethyl 5-(4-t-butoxycarbonylamino-2-nitrobenzoyl)-1-(4-methoxybenzyl)-1,2,3-triazole-4-carboxylate, prepared in the step (b), in ethyl acetate (20 ml) was added 10% palladium on carbon (30 mg). The mixture was stirred under a hydrogen atmosphere overnight and filtered. The filtrate was concentrated under reduced pressure, and the resulting oil was purified by column chromatography on silica gel (toluene:ethyl acetate=2:1) to give ethyl 4-(2-amino-4-t-butoxycarbonylaminobenzoyl)-1-(4-methoxybenzyl)-1,2,3-triazole-5-carboxylate (c-1: less polar component (LP)) (217 mg) and a mixture (219 mg) of the compound c-1 and ethyl 5-(2-amino-4-t-butoxycarbonylaminobenzoyl)-1-(4-methoxybenzyl)-1,2,3-triazole-4-carboxylate (c-2: more polar component (MP)) (219 mg). c-1 (LP):

$^1$H-NMR (CDCl$_3$): δ 1.08 (3H, t), 1.51 (9H, s), 2.35 (2H, br), 3.79 (3H, s), 4.18 (2H, q), 5.84 (2H, s), 6.18 (1H, dd), 6.51 (1H, br), 6.58 (1H, s), 6.86 (1H, d), 7.15–7.38 (4H, m).

SIMS: m/z 496 (M$^+$+1).

(d) A methanol solution (104 μl) of 28% sodium methoxide was added to a methanol (2 ml) solution of the compound c-1 (217 mg) prepared in the step (c). The mixture was stirred at room temperature for 3 hr. The resultant crystal as a precipitate was collected by filtration to give $^7$-t-butoxycarbonylamino-3-(4-methoxybenzyl)-4(5H),10-dioxo-3H-1,2,3-triazolo[4,5c][1]benzazepine (141.8 mg, 55%).

$^1$H-NMR (DMSO-d$_6$): δ 1.48 (9H, s), 3.70 (3H, s), 6.13 (2H, s), 6.89 (2H, d), 7.17 (1H, d), 7.23 (2H, d), 7.36 (2H, s), 8.02 (1H, d), 9.61 (1H, s).

(e) $^7$-t-Butoxycarbonylamino-3-(4-methoxybenzyl)-4(5H),10-dioxo-3H-1,2,3-triazolo[4,5-c] [1]benzazepine (100 mg, 0.22 mmol) prepared in the step (d) was subjected to deprotection using anisole (0.5 ml) and trifluoroacetic acid (5.0 ml) in the same manner as in the step (b) of Example 1, followed by treatment with a 1 N aqueous sodium hydroxide solution to form a sodium salt. This salt was purified on Diaion HP-20 (water:acetone=4:1) to give a sodium salt of the title compound: 7-amino-4(5H),10-dioxo-1H-1,2,3-triazolo[4,5-c][1]benzazepine (20 mg, 40%) as light yellow powder.

$^1$H-NMR (DMSO-d$_6$): δ 3.42 (2H, br), 5.95 (1H, s), 6.41 (1H, m), 8.00 (1H, d), 10.17 (1H, s).

Example 21

7-Acetylamino-4(5H),10-dioxo-1H-1,2,3-triazolo[4,5-c][1]benzazepine (a) To a solution of diisopropylamine (1.1 ml, 7.70 mmol) in tetrahydrofuran (12 ml) was added, at −78° C. under an argon atmosphere, 1.5 N butyllithium (4.8 ml, 7.22 mmol). The mixture was stirred for 30 min. Ethyl propiolate (0.9 ml, 8.66 mmol) and a solution of 4-acetylamino-2-nitrobenzaldehyde (1.0 g, 4.81 mmol) in tetrahydrofuran (6 ml) were added in that order, and the mixture was further stirred at −78° C. for one hr. A solution of acetic acid (0.9 ml, 14.91 mmol) in tetrahydrofuran (3 ml) was then added thereto, followed by extraction with ethyl acetate. The organic layer was washed with dilute hydrochloric acid, water, a saturated aqueous sodium bicarbonate solution, and saturated brine in that order. It was then dried over anhydrous magnesium sulfate. The solvent was removed under reduced pressure to give ethyl 4-hydroxy-4-(4-acetylamino-2-nitrophenyl)-2-butynoate (1.613 g) as an oil. Ethyl 4-hydroxy-4-(4-acetylamino-2-nitrophenyl)-2-butynoate thus prepared was dissolved in toluene (14 ml), 4-methoxybenzylazide (2.35 g, 14.4 mmol) was added to the solution, and the mixture was stirred at 10° C. for 18 hr. The reaction mixture was cooled to room temperature, and the resultant crystal as a precipitate was collected by suction filtration to give a 3:1 mixture (1.09 g, 48%) of ethyl 4-hydroxy-(4-acetylamino-2-nitrophenyl)methyl-1-(4-methoxybenzyl)-1,2,3-triazole-5-carboxylate (a-1) and ethyl 5-hydroxy-(4-acetylamino-2-nitrophenyl)methyl-1-(4-methoxybenzyl)-1,2,3-triazole-4-carboxylate (a-2).

3:1 mixture of a-1 and a-2:

$^1$H-NMR (DMSO-d$_6$): δ 1.25 (3/4H, t), 1.29 (9/4H, t), 2.07 (3/4H, s), 2.09 (9/4H, s), 3.68 (3/4H, s), 3.72 (9/4H, s), 4.27 (1/2H, q), 4.37 (3/2H, q), 5.42 (1/4H, d), 5.54 (1/4H, d), 5.75 (3/4H, d), 5.80 (3/4H, d), 6.25 (3/4H, d), 6.66 (3/4H, d), 6.72 (1/2H, d), 6.90 (2H, d), 6.96 (1/4H, d), 7.09 (1/4H, d), 7.10 (1/4H, d), 7.15 (2H, d), 7.52 (1/4H, d), 7.84 (3/4H, dd), 8.00 (3/4H, d), 8.17 (1/4H, d), 8.35 (3/4H, d), 10.34 (1/4H, s), 10.40 (3/4H, s).

SIMS: m/z 470 (M$^+$+1).

(b) Active manganese dioxide (2.12 g) was added to a solution of 3:1 mixture (708 mg, 1.51 mmol) of ethyl 4-hydroxy-(4-acetylamino-2-nitrophenyl)methyl-1-(4-methoxybenzyl)-1,2,3-triazole-5-carboxylate (a-1) and ethyl 5-hydroxy-(4-acetylamino-2-nitrophenyl)methyl-1-(4-methoxybenzyl)-1,2,3-triazole-4-carboxylate (a-2), prepared in the step (a), in methylene chloride (15 ml), and the mixture was stirred at room temperature overnight. The reaction mixture was filtered through Celite, the Celite was washed with ethyl acetate, and the combined solvent was removed under reduced pressure to give a 3:1 mixture (655.1 mg, 93%) of ethyl 1-(4-methoxybenzyl)-4-(4-acetylamino-2-nitrobenzoyl)-1,2,3-triazole-5-carboxylate (b-1) and ethyl 1-(4-methoxybenzyl)-5-(4-acetylamino-2-nitrobenzoyl)-1,2,3-triazole-4-carboxylate (b-2) as an yellow oil.

3:1 mixture of b-1 and b-2:

$^1$H-NMR (DMSO-d$_6$): δ 0.92 (3/4H, t), 1.21 (9/4H, t), 2.12 (3/4H, s), 2.13 (9/4H, s), 3.68 (3/4H, s), 3.73 (9/4H, s), 3.98 (1/2H, q), 4.31 (3/2H, q), 5.66 (1/2H, s), 5.72 (3/2H, s), 6.84 (1/2H, d), 6.93 (3/2H, d), 7.22 (2H, d), 7.46 (1/4H, d), 7.69 (1/4H, dd), 7.72 (3/4H, d), 7.92 (3/4H, dd), 8.28 (1/4H, s), 8.49 (3/4H, s), 10.70 (3/4H, s), 10.76 (1/4H, s).

EIMS: m/z 467 (M$^+$).

(c) The 3:1 mixture (650 mg, 1.39 mmol) of ethyl 1-(4-methoxybenzyl)-4-(4-acetylamino-2-nitrobenzoyl)-1,2,3-triazole-5-carboxylate (b-1) and ethyl 1-(4-methoxybenzyl)-5-(4-acetylamino-2-nitrobenzoyl)-1,2,3-triazole-4-carboxylate (b-2) prepared in the above step (b) was dissolved in ethyl acetate (29 ml), 10% palladium on carbon (65 mg) was added to the solution, and the mixture was stirred under a hydrogen atmosphere at room temperature for four days. The reaction mixture was filtered through Celite, the filtrate was concentrated under reduced pressure, and the resultant precipitate was collected by filtration to give a 3:1 mixture (565.5 mg, 93%) of ethyl 4-(2-amino-4-acetylaminobenzoyl)-1-(4-methoxybenzyl)-1,2,3-triazole-5-carboxylate (c-1) and ethyl 5-(2-amino-4-acetylaminobenzoyl)-1-(4-methoxybenzyl)-1,2,3-triazole-5-carboxylate (c-2).

3:1 mixture of c-1 and c-2:

$^1$H-NMR (DMSO-d$_6$): δ 0.99 (3H, t), 2.05 (3H, s), 3.66 (3/4H, s), 3.73 (9/4H, s), 4.02 (1/2H, q), 4.14 (3/2H, q), 5.43 (1/2H, s), 5.82 (3/2H, s), 6.36 (1/4H, d), 6.49 (3/4H, d), 6.66 (1/4H, d), 6.78 (1/2H, d), 6.94 (3/2H, d), 7.08 (1/2H, d), 7.16 (3/4H, d), 7.27 (3/2H, d), 7.38 (1/4H, s), 7.41 (3/4H, s), 7.55 (3/2H, brs), 7.64 (1/2H, brs), 10.06 (3/4H, s), 10.07 (1/4H, s).

EIMS: m/z 437 (M$^+$).

(d) To a solution of the 3:1 mixture (550 mg, 1.26 mmol) of ethyl 4-(2-amino-4-acetylaminobenzoyl)-1-(4- methoxybenzyl)-1,2,3-triazole-5-carboxylate (c-1) and ethyl 5-(2-amino-4-acetylaminobenzoyl)-1-(4-methoxybenzyl)-1,2,3-triazole-5-carboxylate (c-2), prepared in the step (c), in methanol (4 ml) was added, under an argon atmosphere with ice cooling, 5.1 M sodium methoxide (0.27 ml, 1.39 mmol). The mixture was stirred with ice cooling for 20 min and then at room temperature overnight. Water was added to the reaction mixture, and the resultant precipitate was collected by filtration, washed with diethyl ether and water, and then dried to give a 3:1 mixture (339.8 mg, 69%) of 7-acetylamino-3-(4-methoxybenzyl)-4(5H),10-dioxo-3H-1,2,3-triazolo[4,5-c][1]benzazepine (d-1) and 7-acetylamino-1-(4-methoxybenzyl)-4(5H),10-dioxo-1H-1,2,3-triazolo[4,5-c][1]benzazepine (d-2) as a yellow crystalline powder.

3:1 mixture of d-1 and d-2:
$^1$H-NMR (DMSO-d$_6$): δ 2.10 (3H, s), 3.71 (3H, s), 5.99 (1/2H, s), 6.07 (3/2H, s), 6.90 (2H, d), 7.27 (1/2H, d), 7.30 (3/2H, d), 7.44 (3/4H, dd), 7.47 (1/4H, dd), 7.79 (1/4H, d), 7.83 (3/4H, d), 8.13 (1/4H, d), 8.17 (3/4H, d), 10.40 (3/4H, s), 10.45 (1/4H, s), 11.49 (1H, brs).
EIMS: m/z 391 (M$^+$).

(e) Anisole (0.4 ml) and trifluoroacetic acid (4.0 ml) were added to the 3:1 mixture of 7-acetylamino-3-(4-methoxybenzyl)-4(5H),10-dioxo-3H-1,2,3-triazolo[4,5-c][1]benzazepine (d-1) and 7-acetylamino-1-(4-methoxybenzyl)-4(5H),10-dioxo-1H-1,2,3-triazolo[4,5-c][1]benzazepine (d-2) (150 mg, 0.38 mmol) prepared in the step (d), and the mixture was stirred at 60° C. for 20 min. The solvent was removed under reduced pressure, and the resultant precipitate was collected by filtration, washed with diethyl ether, and dried to give the title compound: 7-acetylamino-4(5H),10-dioxo-1H-1,2,3-triazolo[4,5-c][1]benzazepine as brown crystalline powder (100 mg, 94%).
$^1$H-NMR (DMSO-d$_6$): δ 2.11 (3H, s), 7.49 (1H, dd), 7.84 (1H, d), 8.24 (1H, d), 10.44 (1H, s), 11.44 (1H, brs).
FDMS: m/z 272 (M$^+$+1).

Example 22
4(5H),10-Dioxo-7-(4-phenylbutoxybenzoylamino)-1H-1,2,3-triazolo[4,5-c][1]benzazepine (a) To a solution of diisopropylamine (0.6 ml, 4.26 mmol) in tetrahydrofuran (12 ml) was added, at −78° C. under an argon atmosphere, 1.5 N butyllithium (2.66 ml, 3.99 mmol). The mixture was stirred for 30 min. Ethyl propiolate (0.49 ml, 4.79 mmol) and a solution of 2-nitro-4-phenylbutoxybenzoylaminobenzaldehyde (1.1 g, 2.66 mmol) in tetrahydrofuran (3 ml) were added in that order, and the mixture was stirred at −78° C. for additional one hr. A solution of acetic acid (0.47 ml, 8.25 mmol) in tetrahydrofuran (3 ml) was then added thereto, followed by extraction with ethyl acetate. The organic layer was washed with dilute hydrochloric acid, water, a saturated aqueous sodium bicarbonate solution, and saturated brine in that order. It was then dried over anhydrous magnesium sulfate. The solvent was removed under reduced pressure to give ethyl 4-hydroxy-4-(2-nitro-4-phenylbutoxybenzoylaminophenyl)-2-butynoate as an oil (1.443 g). Ethyl 4-hydroxy-4-(2-nitro-4-phenylbutoxybenzoylaminophenyl)-2-butynoate thus prepared was dissolved in toluene (10 ml), 4-methoxybenzylazide (1.3 g, 7.98 mmol) was added to the solution, and the mixture was stirred at 100° C. for 5 hr. The reaction mixture was cooled to room temperature, and the resultant crystal was collected by filtration to give ethyl 4-hydroxy-1-(4-methoxybenzyl)-(2-nitro-4-phenylbutoxybenzoylaminophenyl)methyl-1,2,3-triazole-5-carboxylate (a-1) (550.4 mg, 26%). Further, the filtrate was concentrated, and the resultant powder was washed with hexane:ethyl acetate (1:1) and dried to give ethyl 5-hydroxy-1-(4-methoxybenzyl)-(2-nitro-4-phenylbutoxybenzoylaminophenyl)methyl-1,2,3-triazole-4-carboxylate (a-2) (466.3 mg, 30%).

a-1:
$^1$H-NMR (DMSO-d$_6$): δ 1.31 (3H, t), 1.70–1.82 (4H, m), 2.66 (2H, t), 3.72 (3H, s), 4.09 (2H, t), 4.37 (2H, q), 5.76 (1H, d), 5.81 (1H, d), 6.28 (1H, d), 6.70 (1H, d), 6.91 (2H, d), 7.08 (2H, d), 7.12–7.33 (7H, m), 7.98 (2H, d), 8.04 (1H, d), 8.15 (1H, dd), 8.54 (1H, d), 10.50 (1H, s).
SIMS: m/z 680 (M$^+$+1).

a-2:
$^1$H-NMR (DMSO-d$_6$): δ 1.26 (3H, t), 1.70–1.82 (4H, m), 2.66 (2H, t), 3.63 (3H, s), 4.09 (2H, t), 4.28 (2H, q), 5.44 (1H, d), 5.56 (1H, d), 6.73 (2H, d), 6.91 (2H, d), 6.98 (1H, d), 7.07 (2H, d), 7.12–7.34 (7H, m), 7.84 (1H, dd), 7.96 (2H, d), 8.37 (1H, d), 10.43 (1H, s).
SIMS: m/z 680 (M$^+$+1).

(b) Active manganese dioxide (1.65 g) was added to a solution of ethyl 4-hydroxy-1-(4-methoxybenzyl)-(2-nitro-4-phenylbutoxybenzoylaminophenyl)methyl-1,2,3-triazole-5-carboxylate (a-1) (548.9 mg, 0.81 mmol), prepared in the step (a), in chloroform (8 ml), and the mixture was stirred at room temperature overnight. The reaction mixture was filtered through Celite and the Celite was washed with ethyl acetate, and the combined solvent was removed under reduced pressure to give ethyl 1-(4-methoxybenzyl)-4-(2-nitro-4-phenylbutoxybenzoylaminobenzoyl)-1,2,3-triazole-5-carboxylate (b-1) as an orange oil (534.5 mg, 98%).

b-1:
$^1$H-NMR (DMSO-d$_6$): δ 1.17 (3H, t), 1.70–1.81 (4H, m), 2.66 (2H, t), 3.74 (3H, s), 4.10 (2H, t), 4.31 (2H, q), 5.73 (2H, s), 6.94 (2H, d), 7.10 (2H, d), 7.12–7.40 (7H, m), 7.77 (1H, d), 8.01 (2H, d), 8.24 (1H, dd), 8.69 (1H, d), 10.75 (1H, s).
SIMS: m/z 678 (M$^+$+1).

(b) Similarly, active manganese dioxide (1.37 g) was added to a solution of ethyl 5-hydroxy-1-(4-methoxybenzyl)-5-(2-nitro-4-phenylbutoxybenzoylaminobenzoyl)-1,2,3-triazole-4-carboxylate (a-2) (458.3 mg, 0.67 mmol), prepared in the step (a), in chloroform (7 ml), and the mixture was stirred at room temperature overnight to give ethyl 1-(4-methoxybenzyl)-5-(2-nitro-4-phenylbutoxybenzoylaminobenzoyl)-1,2,3-triazole-5-carboxylate (b-2) as a yellow oil (428.4 mg, 99%). b-2:
$^1$H-NMR (DMSO-d$_6$): δ 0.95 (3H, t), 1.70–1.82 (4H, m), 2.66 (2H, t), 3.68 (3H, s), 4.00 (2H, q), 4.10 (2H, t), 5.68 (2H, s), 6.86 (2H, d), 7.09 (2H, d), 7.15–7.32 (7H, m), 7.53 (1H, d), 7.99 (2H, d), 8.03 (1H, dd), 8.49 (1H, d), 10.79 (1H, s).
SIMS: m/z 678 (M$^+$+1).

(c) Ethyl 1-(4-methoxybenzyl)-4-(2-nitro-4-phenylbutoxybenzoylaminobenzoyl)-1,2,3-triazole-5-carboxylate (b-1) (529.5mg, 0.78 mmol) prepared in the step (b) was dissolved in ethanol (8 ml) and ethyl acetate (2 ml), 10% palladium on carbon (53 mg) was added to the solution, and the mixture was stirred at room temperature under a hydrogen atmosphere for two days. The reaction mixture was filtered through Celite, and the filtrate was concentrated under reduced pressure. The resultant precipitate was collected by filtration to give ethyl 4-(2-amino-4-phenylbutoxybenzoylaminobenzoyl)-1-(4-methoxybenzyl)-1,2,3-triazole-5-carboxylate (c-1) as a yellow oil (484.4 mg, 96%).

c-1:
$^1$H-NMR (DMSO-d$_6$): δ 1.02 (3H, t), 1.70–1.80 (4H, m), 2.65 (2H, t), 3.74 (3H, s), 4.03 (2H, q), 4.09 (2H, t), 5.83

(2H, s), 6.78 (1H, dd), 6.95 (2H, d), 7.04 (2H, d), 7.13–7.37 (8H, m), 7.57 (1H, d), 7.93 (2H, d), 10.16 (1H, s).

SIMS: m/z 648 (M$^+$+1).

Ethanol (6 ml) and ethyl acetate (3 ml) were added to ethyl 1-(4-methoxybenzyl)-5-(2-nitro-4-phenylbutoxybenzoylaminobenzoyl)-1,2,3-triazole-4-carboxylate (b-2) (422 mg, 0.62 mmol) prepared in the step (b), 10% palladium on carbon (42 mg) was added to the solution, and the mixture was stirred at room temperature under a hydrogen atmosphere for three days to give ethyl 5-(2-amino-4-phenylbutoxybenzoylaminobenzoyl)-1-(4-methoxybenzyl)-1,2,3-triazole-5-carboxylate (c-2) (344 mg, 85%).

c-2:

$^1$H-NMR (DMSO-d$_6$): δ 1.00 (3H, t), 1.70–1.80 (4H, m), 2.65 (2H, t), 3.67 (3H, s), 4.03 (2H, q), 4.10 (2H, t), 5.45 (2H, S), 6.64 (1H, dd), 6.71 (1H, d), 6, 80 (2H, d), 7.04 (2H, d), 7.11 (2H, d), 7.15–7.33 (5H, m), 7.60 (1H, d), 7.66 (2H, brs), 7.92 (2H, d), 10.17 (1H, s).

SIMS: m/z 648 (M$^+$+1).

(d) To a solution of ethyl 4-(2-amino-4-phenylbutoxybenzoylaminobenzoyl)-1-(4-methoxybenzyl)-1,2,3-triazole-5-carboxylate (c-1) (475.6 mg, 0.74 mmol), prepared in the step (c), in methanol (5 ml) was added, under an argon atmosphere with ice cooling, 5.1 M sodium methoxide (0.16 ml, 0.81 mmol). The mixture was stirred with ice cooling for 20 min and then at room temperature overnight. Water was added to the reaction mixture, and the resultant precipitate was collected by filtration, washed with diethyl ether and water, and then dried to give 3-(4-methoxybenzyl)-4(5H),10-dioxo-7-phenylbutoxybenzoylamino-3H-1,2,3-triazolo[4,5-c][1]benzazepine (d-1) as yellow crystalline powder (361 mg, 82%).

d-1:

$^1$H-NMR (DMSO-d$_6$): δ 1.68–1.82 (4H, m), 2.66 (2H, t), 3.72 (3H, s), 4.09 (2H, t), 6.09 (2H, s), 6.90 (2H, d), 7.06 (2H, d), 7.13–7.42 (7H, m), 7.55 (1H, dd), 7.97 (2H, d), 8.03 (1H, d), 8.18 (1H, d), 10.45 (1H, brs), 11.60 (1H, brs).

SIMS: m/z 602 (M$^+$+1).

(e) Anisole (0.6 ml) and trifluoroacetic acid (6.0 ml) were added to 3-(4-methoxybenzyl)-4(5H),10-dioxo-7-phenylbutoxybenzoylamino-3H-1,2,3-triazolo[4,5-c][1]benzazepine (d-1) (356 mg, 0.59 mmol) prepared in the step (d), and the mixture was stirred at 60° C. for 10 min. The solvent was removed under reduced pressure, and the resultant precipitate was collected by filtration, washed with diethyl ether, and then dried to give the title compound: 4(5H),10-dioxo-7-phenylbutoxybenzoylamino-1H-1,2,3-triazolo[4,5-c][1]benzazepine (225 mg, 79%) as yellow crystalline powder.

$^1$H-NMR (DMSO-d$_6$): δ 1.70–1.82 (4H, m), 2.66 (2H, t), 4.09 (2H, t), 7.07 (2H, d), 7.13–7.33 (5H, m), 7.61 (1H, dd), 7.98 (2H, d), 8.15 (1H, d), 8.29 (1H, d), 10.55 (1H, s), 11.44 (1H, brs).

FDMS: m/z 482 (M$^+$+1).

Example 23

8-Isopropoxy-7-methoxy-4(5H),10-dioxo-1H-1,2,3-triazolo[4,5-c][1]benzazepine (a) To a solution of diisopropylamine (5.0 ml, 36.0 mmol) in tetrahydrofuran (75 ml) was added, at −78° C. under an argon atmosphere, 1.5 N butyllithium (22.6 ml, 33.8 mmol). The mixture was stirred for one hr. Ethyl propiolate (2.9 ml, 28.2 mmol) and a solution of 5-isopropoxy-4-methoxy-2-nitrobenzaldehyde (4.5 g, 18.8 mmol) in tetrahydrofuran (50 ml) were added in that order, and the mixture was stirred at −78° C. for additional 1.5 hr. A solution of acetic acid (5.9 ml, 102 mmol) in tetrahydrofuran (20 ml) was added to the reaction mixture. After water was added, the reaction mixture was extracted with ethyl acetate. The organic layer was washed with dilute hydrochloric acid, water, a saturated aqueous sodium bicarbonate solution, and saturated brine in that order. It was then dried over anhydrous magnesium sulfate. The solvent was removed under reduced pressure to give ethyl 4-(5-isopropoxy-4-methoxy-2-nitrophenyl)-4-hydroxy-2-butynoate as an oil (7.27 g). Ethyl 4-(5-isopropoxy-4-methoxy-2-nitrophenyl)-4-hydroxy-2-butynoate was dissolved in toluene (60 ml), 4-methoxybenzylazide (9.2 g, 56.4 mmol) was added to the solution, and the mixture was stirred at 100° C. overnight. The reaction mixture was cooled to room temperature, and the solvent was removed under reduced pressure. The residue was purified by column chromatography on silica gel (hexane:ethyl acetate=1:2) to give a 1:1 mixture (7.01 g, 75%) of ethyl 4-(1-hydroxy-(5-isopropoxy-4-methoxy-2-nitrophenyl)methyl)-1-1(4-methoxybenzyl)-1,2,3-triazole-5-carboxylate (a-1: low polar product (LP)) and ethyl 5-(1-hydroxy-(5-isopropoxy-4-methoxy-2-nitrophenyl)methyl)-1-(4-methoxybenzyl)-1,2,3-triazole-4-carboxylate (a-2: high polar product (MP)).

1:1 mixture of a-1 (LP) and a-2 (MP):

$^1$H-NMR (CDCl$_3$): δ 1.34–1.55 (9H, m), 3.59 (1H, d), 3.77 (3H, s), 3.92 (3H, s), 4.41 (2H, q), 4.69–4.76 (1H, m), 5.81 (1H, s), 5.83 (1H, s), 6.82 (2H, d), 6.93 (1H, d), 7.20 (2H, d), 7.43 (1H, s), 7.67 (1H, s).

SIMS: m/z 501 (M$^+$+1).

(b) Active manganese dioxide (24 g) was added to a solution of the 1:1 mixture (7.01 g, 14.02 mmol) of the compound (a-1) and the compound (a-2), prepared in the step (a), in methylene chloride (160 ml), and the mixture was stirred at room temperature overnight. The reaction mixture was filtered through Celite and the Celite was washed with methylene chloride, and the solvent was removed under reduced pressure to give a 1:1 mixture (6.98 g, 100%) of ethyl 4-(5-isopropoxy-4-methoxy-2-nitrobenzoyl)-1-(4-methoxybenzyl)-1,2,3-triazole-5-carboxylate (b-1: LP)) and ethyl 5-(5-isopropoxy-4-methoxy-2-nitrobenzoyl)-1-(4-methoxybenzyl)-1,2,3-triazole-4-carboxylate (b-2: MP) as a foam.

1:1 mixture of b-1 (LP) and b-2 (MP):

$^1$H-NMR (CDCl$_3$): δ 1.17 (3/2H, t), 1.37–1.43 (9/2H, m), 3.78 (3H, s), 3.97 (3/2H, s), 3.99 (3/2H, s), 4.08 (1H, q), 4.42 (1H, q), 4.55–4.60 (1/2H, m), 4.67–4.72 (1/2H, m), 5.70 (1H, s), 5.78 (1H, s), 6.79 (1/2H, s), 6.84–6.88 (2H, m), 6.97 (1/2H, s), 7.24 (1H, d), 7.42 (1H, d), 7.52 (1/2H, s), 7.67 (1/2H, s).

EIMS: m/z 498 (M$^+$).

(c) The 1:1 mixture (6.73 g, 13.52 mmol) of ethyl 4-(5-isopropoxy-4-methoxy-2-nitrobenzoyl)-1-(4-methoxybenzyl)-1,2,3-triazole-5-carboxylate (b-1: LP) and ethyl 5-(5-isopropoxy-4-methoxy-2-nitrobenzoyl)-1-(4-methoxybenzyl)-1,2,3-triazole-4-carboxylate (b-2: MP) prepared in the step (b) was dissolved in ethyl acetate (150 ml). 10% palladium on carbon (600 mg) was added to the solution, and the mixture was stirred at room temperature under a hydrogen atmosphere for 16 hr. The reaction mixture was filtered through Celite, and the filtrate was concentrated under reduced pressure to give a 1:1 mixture of ethyl 4-(2-amino-5-isopropoxy-4-methoxybenzoyl)-1-(4-methoxybenzyl)-1,2,3-triazole-5-carboxylate (c-1: LP) and ethyl 5-(2-amino-5-isopropoxy-4-methoxybenzoyl)-1-(4-methoxybenzyl)-1,2,3-triazole-4 -carboxylate (c-2: MP) as yellow oil (6.20 g, 98%). 1:1 mixture of c-1 (LP) and c-2 (MP):

$^1$H-NMR (CDCl$_3$):δ 1.17–1.20 (9H, m), 3.69 (3/2H, s), 3.79 (3/2H, s), 3.84 (3/2H, s), 3.85 (3/2H, s), 4.04–4.25 (3H, m), 5.25–5.65 (1H, brs), 5.85 (1H, s), 6.07 (1/2H, s), 6.12 (1/2, s), 6.15 (1/2H, s), 6.34–6.55 (2H, brs), 6.68 (1H, d), 6.86 (1H, d), 6.90 (1/2H, s), 7.11 (1H, d), 7.33 (1H, d).

EIMS: m/z 468 (M$^+$).

(d) The 1:1 mixture of ethyl 4-(2-amino-5-isopropoxy-4-methoxybenzoyl)-1-(4-methoxybenzyl)-1,2,3-triazole-5-carboxylate (c-1: LP) and ethyl 5-(2-amino-5-isopropoxy-4-methoxybenzoyl)-1-(4-methoxybenzyl)-1,2,3-triazole-4-carboxylate (c-2: MP) (6.20 g, 13.25 mmol) prepared in the step (c) was dissolved in methanol (50 ml), a solution of 28% sodium methoxide in methanol (2.9 ml, 14.57 mmol) was added to the solution, and the mixture was stirred at room temperature for 3 hr. Water was added to the reaction mixture, and the resultant precipitate was collected by filtration, washed with diethyl ether, and dried to give a 1:1 mixture of 8-isopropoxy-7-methoxy-3-(4-methoxybenzyl)-4(5H),10-dioxo-3H-1,2,3-triazolo[4,5-c][1]benzazepine (d-1: LP) and 8-isopropoxy-7-methoxy-1-(4-methoxybenzyl)-4(5H),10-dioxo-1H-1,2,3-triazolo[4,5-c][1]benzazepine (d-2: MP) as yellow crystalline powder (4.39 g, 79%).

1:1 mixture of d-1 (LP) and d-2 (MP):
$^1$H-NMR (DMSO-d$_6$):δ 1.27 (6H, d), 3.70 (3H, s), 3.82 (3H, s), 4.55–4.60 (1H, m), 6.02 (1H, s), 6.09 (1H, s), 6.88 (2H, d), 7.07 (1H, s), 7.26 (2H, d), 7.65 (1H, s), 11.10–11.63 (1H, brs).

FDMS: m/z 423 (M$^+$+1).

(e) Anisole (15 ml) and trifluoroacetic acid (60 ml) were added to the 1:1 mixture of 8-isopropoxy-7-methoxy-3-(4-methoxybenzyl)-4(5H),10-dioxo-3H-1,2,3-triazolo[4,5-c][1]benzazepine (d-1: LP) and 8-isopropoxy-7-methoxy-1-(4-methoxybenzyl)-4(5H),10-dioxo-1H-1,2,3-triazolo[4,5-c][1]benzazepine (d-2: MP) (1.55 g, 3.68 mmol) prepared in the step (d), and the mixture was stirred at 70° C. for one hr. Trifluoroacetic acid was removed under reduced pressure, isopropyl ether was added to the residue, and the resultant powder was collected by filtration and dried to give 8-isopropoxy-7-methoxy-4(5H),10-dioxo-1H-1,2,3-triazolo[4,5-c][1]benzazepine as yellow crystalline powder (540 mg, 48%).

$^1$H-NMR (DMSO-d$_6$):δ 1.28 (6H, d), 3.84 (3H, s), 4.56–4.63 (1H, m), 7.20 (1H, s), 7.70 (1H, s), 11.19 (1H, s).

SIMS: m/z 303 (M$^+$+1).

Example 24
7-Isopropoxy-8-methoxy-4(5H),10-dioxo-1H-1,2,3-triazolo[4,5-c][1]benzazepine (a) To a solution of diisopropylamine (0.59 ml, 4.21 -mmol) in tetrahydrofuran (5 ml) was added, at −78° C. under an argon atmosphere, a 1.5 N butyllithium hexane solution (2.7 ml, 4.05 mmol). The mixture was stirred for one hr. A solution of ethyl propiolate (0.33 ml, 3.26 mmol) in tetrahydrofuran (2 ml) and a solution of 4-isopropoxy-5-methoxy-2-nitrobenzaldehyde (562 mg, 2.35 mmol) in tetrahydrofuran (5 ml) were added in that order, and the mixture was stirred at −78° C. for additional 1.5 hr. A solution of acetic acid (0.4 ml, 6.99 mmol) in tetrahydrofuran (1 ml) was then added to the reaction mixture, water was then added thereto, and the solvent was removed under reduced pressure. The residue was extracted with ethyl acetate. The organic layer was washed with dilute hydrochloric acid, water, a saturated aqueous sodium bicarbonate solution, and saturated brine in that order.

It was then dried over anhydrous magnesium sulfate. The solvent was removed under reduced pressure to give ethyl 4-hydroxy-4-(4-isopropoxy-5-methoxy-2-nitrophenyl)-2-butynoate (906 mg) as a brown oil. Ethyl 4-hydroxy-4-(4-isopropoxy-5-methoxy-2-nitrophenyl)-2-butynoate thus prepared was dissolved in toluene (5 ml), 4-methoxybenzylazide (767 mg, 4.70 mmol) was added thereto, and the mixture was stirred at 100° C. overnight. The reaction mixture was cooled to room temperature, and the solvent was removed under reduced pressure. The residue was purified by column chromatography on silica gel (hexane:ethyl acetate=1:1) to give a 1:1 mixture of ethyl 4-(hydroxy-(4-isopropoxy-5-methoxy-2-nitrophenyl)methyl)-1-(4-methoxybenzyl)-1,2,3-triazole-5-carboxylate (a-1: low polar product (LP)) and ethyl 5-(hydroxy-(4-isopropoxy-5-methoxy-2-nitrophenyl)methyl)-1-(4-methoxybenzyl)-1,2,3-triazole-4-carboxylate (a-2: high polar product (MP)) (346 mg, 29%).

1:1 mixture of a-1 (LP) and a-2 (MP):
$^1$H-NMR (CDCl$_3$): δ 1.32–1.50 (9H, m), 3.52 (3/2H, s), 3.72 (3/2H, s), 3.78 (3/2H, s), 3.95 (3/2H, s), 4.35–4.45 (2H, m), 4.50–4.70 (1H, m), 5.15 (1/2H, d), 5.47 (1/2H, d), 5.67 (1/2H, d), 5.79 (1/2H, d), 5.84 (1/2H, d), 6.27 (1/2H, s), 6.66 (1H, d), 6.83 (1H, d), 6.93 (1/2H, d), 7.01 (1H, d), 7.06 (1/2H, d), 7.21 (1H, d), 7.47 (1/2H, s), 7.49 (1/2H, s), 7.70 (1/2H, s).

FDMS: m/z 500(M$^+$).

(b) The 1:1 mixture of ethyl 4-(hydroxy-(4-isopropoxy-5-methoxy-2-nitrophenyl)methyl)-1-(4-methoxybenzyl)-1,2,3-triazole-5-carboxylate (a-1: LP) and ethyl 5-(hydroxy-(4-isopropoxy-5-methoxy-2-nitrophenyl)methyl)-1-(4-methoxybenzyl)-1,2,3-triazole-4-carboxylate (a-2: MP) (319 mg, 0.637 mmol) prepared in the step (a) was dissolved in methylene chloride (6 ml), manganese dioxide (638 mg) was added thereto, and the mixture was stirred at room temperature overnight. Further, manganese dioxide (1.27 g) was added in two divided portions, and the mixture was allowed to react for 6 hr. The reaction mixture was filtered through Celite and the Celite was the Celite was washed with ethyl acetate, and the solvent was removed under reduced pressure to give an about 1:1 mixture of ethyl 4-(4-isopropoxy-5-methoxy-2-nitrobenzoyl)-1-(4-methoxybenzyl)-1,2,3-triazole-5-carboxylate (b-1: LP) and ethyl 5-(5-isopropoxy-4-methoxy-2-nitrobenzoyl)-1-(4-methoxybenzyl)-1,2,3-triazole-4-carboxylate (b-2: MP) (289 mg, 91%).

1:1 mixture of b-1 (LP) and b-2 (MP):
$^1$H-NMR (CDCl$_3$): δ 1.17 (3/2H, t), 1.37 (3/2H, t), 1.44 (3H, d), 1.46 (3H, d), 3.79 (3H, s), 3.88 (3/2H, s), 3.95 (3/2H, s), 4.08 (1H, q), 4.42 (1H, q), 4.65–4.75 (1H, m), 5.72 (1H, s), 5, 78 (1H, s), 6.80 (1/2H, s), 6.85 (1H, d), 6.88 (1H, d), 6.98 (1/2H, s), 7.24 (1H, d), 7.42 (1H, d), 7.50 (1/2H, s), 7.67 (1/2H, s).

FDMS: m/z 498 (M$^+$).

(c) The 1:1 mixture of ethyl 4-(4-isopropoxy-5-methoxy-2-nitrobenzoyl)-i-(4-methoxybenzyl)-1,2,3-triazole-5-carboxylate (b-1: LP) and ethyl 5-(4-isopropoxy-5-methoxy-2-nitrobenzoyl)-1-(4-methoxybenzyl)-1,2,3-triazole-4-carboxylate (b-2: MP) (284 mg, 0.570 mmol) prepared in the step (b) was dissolved in ethyl acetate (6 ml), 10% palladium on carbon (28 mg) was added to the solution, and the mixture was stirred at room temperature under a hydrogen atmosphere for 14 hr. The reaction mixture was filtered through Celite. The solvent was removed under reduced pressure, methanol (6 ml) and 10% palladium on carbon (28 mg) were added to the residue, and the mixture was stirred at room temperature under a hydrogen atmosphere for 26 hr. The reaction mixture was filtered through Celite, and the filtrate was concentrated under reduced pressure to give a 1:3 mixture of ethyl 4-(2-amino-4-isopropoxy-5-methoxybenzoyl)-1-(4-methoxybenzyl)-1,2,3-triazole-5-carboxylate (c-1: LP) and ethyl 5-(2-amino-4- isopropoxy-5-methoxybenzoyl)-1-(4-methoxybenzyl)-1,2,3-triazole-4-carboxylate (c-2: MP) (253 mg, 95%).

1:3 mixture of c-1 (LP) and c-2 (MP):
$^1$H-NMR (CDCl$_3$): δ 1.05–1.18 (3H, m), 1.30–1.50 (6H, m), 3.36 (9/4H, s), 3.61 (3/4H, s), 3.69 (9/4H, s), 3.79 (3/4H, s), 4.10–4.65 (3H, m), 5.20–5.45 (3/4H, brs), 5.45–5.70 (3/4H, brs), 5.84 (1/2H, s), 5.98 (3/2H, s), 6.06 (3/2H, s), 6.13 (1/4H, s), 6.67 (3/2H, d), 6.86 (1/2H, d), 6.92 (1/4H, s), 7.11 (3/2H, d), 7.33 (1/2H, d).

EIMS: m/z 468 (M$^+$).

(d) Under an argon atmosphere, the 1:3 mixture of ethyl 4-(2-amino-4-isopropoxy-5-methoxybenzoyl)-1-(4-methoxybenzyl)-1,2,3-triazole-5-carboxylate (c-1: LP) and ethyl 5-(2-amino-4-isopropoxy-5-methoxybenzoyl)-1-(4-methoxybenzyl)-1,2,3-triazole-4-carboxylate (c-2: MP) (244 mg, 0.521 mmol) prepared in the step (c) was dissolved in methanol (5 ml), a solution of 28% sodium methoxide in methanol (0.11 ml, 0.561 mmol) was added to the solution, and the mixture was stirred at room temperature overnight. Water was added to the reaction mixture, and the resultant crystal as a precipitate was collected by filtration and dried to give an about 1:2 mixture of 7-isopropoxy-8-methoxy-3-(4-methoxybenzyl)-4(5H),10-dioxo-1H-1,2,3-triazolo[4,5-c][1]benzazepine (d-1: LP) and 7-isopropoxy-8-methoxy-1-(4-methoxybenzyl)-4(5H),10-dioxo-3H-1,2,3-triazolo[4,5-c][1]benzazepine (d-2: MP) (89 mg, 40%).

1:2 mixture of d-1 (LP) and d-2 (MP):
$^1$H-NMR (DMSO-d$_6$): δ 1.35 (6H, d), 3.71 (2H, s), 3.72 (1H, s), 3.82 (2H, s), 3.83 (1H, s), 4.54–4.67 (1H, m), 6.04 (4/3H, s), 6.09 (2/3H, s), 6.90 (2H, d), 7.18 (1/3H, s), 7.19 (2/3H, s), 7.28 (4/3H, d), 7.30 (2/3H, d), 7.60 (1/3H, s), 7.68 (2/3H, s), 11.16 (2/3H, s), 11.33 (1/3H, s).

EIMS: m/z 422 (M$^+$).

(e) Anisole (0.2 ml) and trifluoroacetic acid (2.0 ml) were added to about 1:2 mixture of 7-isopropoxy-8-methoxy-3-(4-methoxybenzyl)-4(5H),10-dioxo-3H-1,2,3-triazolo[4,5-c][1]benzazepine (d-1: LP) and 7-isopropoxy-8-methoxy-1-(4-methoxybenzyl)-4(5H),10-dioxo-1H-1,2,3-triazolo[4,5-c][1]benzazepine (d-2: MP) (86 mg, 0.204 mmol) prepared in the step (d), and the mixture was stirred at 60° C. for 2 hr. The solvent was removed under reduced pressure, and the resultant precipitate was collected by filtration and dried to give the title compound: 7-isopropoxy-8-methoxy-4(5H),10-dioxo-1H-1,2,3-triazolo[4,5-c][1]benzazepine (e') (51 mg, 83%). The compound (e') was dissolved in a 1 N aqueous sodium hydroxide solution and purified on Diaion HP-20 to give a sodium salt of the title compound: 7-isopropoxy-8-methoxy-4(5H),10-dioxo-1H-1,2,3-triazolo[4,5-c][1]benzazepine (e) (52 mg, 95%).

(e'):
$^1$H-NMR (DMSO-d$_6$): δ 1.36 (6H, d), 3.84 (3H, s), 4.56–4.67 (1H, m), 7.23 (1H, s), 7.70 (1H, s), 11.19 (1H, s).
FDMS: m/z 302 (M$^+$).

(e):
$^1$H-NMR (DMSO-d$_6$): δ 1.33 (6H, d), 3.80 (3H, s), 4.52–4.65 (1H, m), 7.14 (1H, s), 7.73 (1H, s), 10.35 (1H, s).
FDMS: m/z 325 (M$^+$+1).

Example 25

7,8-diisopropoxy-4(5H),10-dioxo-1H-1,2,3-triazolo[4,5-c][1]benzazepine (a) To a solution of diisopropylamine (5.0 ml, 36.0 mmol) in tetrahydrofuran (75 ml) was added, at −78° C. under an argon atmosphere, a 1.5 N butyllithium (22.6 ml, 33.8 mmol). The mixture was stirred for one hr. Ethyl propiolate (2.9 ml, 28.2 mmol) and a solution of 4,5-diisopropoxy-2-nitrobenzaldehyde (5.0 g, 18.7 mmol) in tetrahydrofuran (50 ml) were added in that order, and the mixture was stirred at −78° C. for additional 1.5 hr. A solution of acetic acid (5.9 ml, 102 mmol) in tetrahydrofuran (20 ml) was then added to the reaction mixture, water was then added thereto, followed by extraction with ethyl acetate. The organic layer was washed with dilute hydrochloric acid, water, a saturated aqueous sodium bicarbonate solution, and saturated brine in that order. It was then dried over anhydrous magnesium sulfate. The solvent was removed under reduced pressure. The resultant mixture was purified by column chromatography on silica gel (hexane:ethyl acetate=1:1) to give ethyl 4-(4,5-diisopropoxy-2-nitrophenyl)-4-hydroxy-2-butynoate (7.80 g). Ethyl 4-(4,5-diisopropoxy-2-nitrophenyl)-4-hydroxy-2-butynoate thus obtained was dissolved in toluene (60 ml), 4-methoxybenzylazide (10.5 g, 64.4 mmol) was added thereof, and the mixture was stirred at 100° C. for 9 hr. The reaction mixture was cooled to room temperature, and the solvent was removed under reduced pressure. The residue was purified by column chromatography on silica gel (hexane:ethyl acetate=1:2) to give a 1:1 mixture of ethyl 4-(1-hydroxy-(4,5-diisopropoxy-2-nitrophenyl)methyl)-1-(4-methoxybenzyl)-1,2,3-triazole-5-carboxylate (a-1: low polar product (LP)) and ethyl 5-(1-hydroxy-(4,5-diisopropoxy-2-nitrophenyl)methyl)-1-(4-methoxybenzyl)-1,2,3-triazole-4-carboxylate (a-2: high polar product (MP)) (5.34 g, 54%).

1:1 mixture of a-1 (LP) and a-2 (MP):
$^1$H-NMR (CDCl$_3$): δ 1.13–1.15 (15H, m), 3.55 (1H, d), 3.78 (3H, s), 4.40 (2H, q), 4.52–4.56 (1H, m), 4.63–4.67 (1H, m), 5.81 (2H, d), 6.83 (2H, d), 6.91 (1H, s), 7.23 (2H, d), 7.39 (1H, s), 7.70 (1H, s).

EIMS: m/z 528 (M$^+$).

(b) A 1:1 mixture of the compound (a-1) and the compound (a-2) (5.34 g, 11.87 mmol) prepared in the step (a) was dissolved in methylene chloride (110 ml), active manganese dioxide (17 g) was added thereto, and the mixture was stirred at room temperature overnight. The reaction mixture was filtered through Celite and the Celite was washed with methylene chloride, and the solvent was removed under reduced pressure to give a 1:1 mixture of ethyl 4-(4,5-diisopropoxy-2-nitrobenzoyl)-1-(4-methoxybenzyl)-1,2,3-triazole-5-carboxylate (b-1: LP) and ethyl 5-(4,5-diisopropoxy-2-nitrobenzoyl)-1-(4-methoxybenzyl)-1,2,3-triazole-4-carboxylate (b-2: MP) as a foam (4.68 g, 88%).

1:1 mixture of b-1 (LP) and b-2 (MP):
$^1$H-NMR (CDCl$_3$): δ 1.16 (3/2H, t), 1.35–1.45 (27/2H, m), 3.79 (3H, s), 4.08 (1H, q), 4.42 (1H, q), 4.50–4.68 (2H, m), 5.71 (1H, s), 5.78 (1H, s), 6.80 (1/2H, s), 6.85–6.89 (2H, m), 6.99 (1/2H, s), 7.24 (1H, d), 7.40 (1H, d), 7.53 (1/2H, s), 7.69 (1/2H, s).

FDMS: m/z 526 (M$^+$).

(c) The 1:1 mixture of ethyl 4-(4,5-diisopropoxy-2-nitrobenzoyl)-1-(4-methoxybenzyl)-1,2,3-triazole-5-carboxylate (b-1: LP) and ethyl 5-(4,5-diisopropoxy-2-nitrobenzoyl)-1-(4-methoxybenzyl)-1,2,3-triazole-4-carboxylate (b-2: MP) (4.50 g, 8.56 mmol) prepared in the step (b) was dissolved in ethyl acetate (100 ml), 10% palladium on carbon (450 mg) was added thereto, and the mixture was stirred at room temperature under a hydrogen atmosphere for 16 hr. The reaction mixture was filtered through Celite, and the filtrate was concentrated under reduced pressure to give a 1:1 mixture of ethyl 4-(2-amino-4,5-diisopropoxybenzoyl)-1-(4-methoxybenzyl)-1,2,3-triazole-5-carboxylate (c-1: LP) and ethyl 5-(2-amino-4,5-diisopropoxy)-1-(4-methoxybenzyl)-1,2,3-triazole-4-carboxylate (c-2: MP) as a yellowish brown oil (4.40 g, 103%).

1:1 mixture of c-1 (LP) and c-2 (MP):
$^1$H-NMR (CDCl$_3$):δ 1.07–1.23 (9H, m), 1.37 (6H, d), 3.69 (3/2H, s), 3.79 (3/2H, s), 4.04–4.64 (411, m), 5.30–5.61 (1H, brs), 5.50 (1/2H, s), 5.85 (1/2, s), 6.04 (1/2H, s),6.10 (1/2H, s), 6.25 (1/2H, s), 6.30–6.50 (2H, brs), 6.68 (1H, d), 6.87 (1H, d), 6.91 (1/2H, s), 7.11 (1H, d), 7.33 (1H, d).
EIMS: m/z 496 (M$^+$).

(d) The 1:1 mixture of ethyl 4-(2-amino-4,5-diisopropoxybenzoyl)-1-(4-methoxybenzyl)-1,2,3-triazole-5-carboxylate (c-1: LP) and ethyl 5-(2-amino-4,5-diisopropoxy)-1-(4-methoxybenzyl)-1,2,3-triazole-4-carboxylate (c-2: MP) (4.30 g, 8.67 mmol) prepared in the step (c) was dissolved in methanol (50 ml), a solution of 28% sodium methoxide in methanol (2.2 ml, 11.32 mmol) was added to the solution, and the mixture was stirred at room temperature for 4 hr. Water was added to the reaction mixture, and the resultant precipitate was collected by filiation and washed with diethyl ether to give a 1:1 mixture of 7,8-diisopropoxy-3-(4-methoxybenzyl)-4(5H),10-dioxo-3H-1,2,3-triazolo[4,5-c][1]benzazepine (d-1: LP) and 7,8-diisopropoxy-1-(4-methoxybenzyl)-4(5H),10-dioxo-1H-1,2,3-triazolo[4,5-c][1]benzazepine (d-2: MP) (2.47 g, 70%) as yellow crystalline powder.

1:1 mixture of d-1 (LP) and d-2 (MP):
$^1$H-NMR (DMSO-d$_6$):δ 1.26–1.35 (12H, m), 3.70 (3H, s), 4.50–4.59 (2H, m), 6.03 (1H, s), 6.09 (1H, s), 6.89 (2H, d), 7.10 (1H, s), 7.28 (2H, d), 7.68 (1H, s), 11.16–11.40(1H, brs).
FDMS: m/z 450(M$^+$).

(e) Anisole (15 ml) and trifluoroacetic acid (60 ml) were added to the 1:1 mixture of 7,8-diisopropoxy-3-(4-methoxybenzyl)-4(5H),10-dioxo-3H-1,2,3-triazolo[4,5-c][1]benzazepine (d-1: LP) and 7,8-diisopropoxy-1-(4-methoxybenzyl)-4(5H),10-dioxo-1H-1,2,3-triazolo[4,5-c][1]benzazepine (d-2: MP) (1.46 g, 2.94 mmol) prepared in the step (d), and the mixture was stirred at 70° C. for 1.5 hr. Trifluoroacetic acid was removed from the reaction mixture by distillation, isopropyl ether was added thereto, and the resultant powder as a precipitate was collected by filtration and dried to give 7,8-diisopropoxy-4(5H),10-dioxo-1H-1,2,3-triazolo[4,5-c][1]benzazepine as yellow crystalline powder (886 mg, 91%).
$^1$H-NMR (DMSO-d$_6$):δ 1.28 (6H, d), 1.34 (6H, d), 4.47–4.53 (1H, m), 4.46–4.62 (1H, m), 7.21 (1H, s), 7.72 (1H, s), 11.14 (1H, s).
SIMS: m/z 331 (M$^+$+1).

Example 26
7,8-Methylenedioxy-4(5H),10-dioxo-1H-1,2,3-triazolo[4,5-c][1]benzazepine (a) To a solution of diisopropylamine (6.8 ml, 49.0 mol) in tetrahydrofuran (80 ml) was added, at −78° C. under an argon atmosphere, a 1.5 N butyllithium (30.7 ml, 46.0 mmol). The mixture was stirred for one hr. Ethyl propiolate (3.9 ml, 38.4 mmol) and a solution of 4,5-methylenedioxy-2-nitrobenzaldehyde (5.0 g, 25.6 mmol) in tetrahydrofuran (50 ml) were added in that order to the reaction mixture, and the mixture was stirred at −78° C. for additional 1.5 hr. A solution of acetic acid (8.0 ml, 139 mmol) in tetrahydrofuran (20 ml) was then added thereto, water was then added thereto, followed by extraction with ethyl acetate. The organic layer was washed with dilute hydrochloric acid, water, a saturated aqueous sodium bicarbonate solution, and saturated brine in that order. It was then dried over anhydrous magnesium sulfate. The solvent was removed under reduced pressure to give ethyl 4-hydroxy-4-(4,5-methylenedioxy-2-nitrophenyl)-2-butynoate as an oil (8.93 g). Ethyl 4-hydroxy-4-(4,5-methylenedioxy-2-nitrophenyl)-2-butynoate thus prepared was dissolved in toluene (75 ml), 4-methoxybenzylazide (14.9 g, 91.1 mmol) was added to the solution, and the mixture was stirred at 100° C. overnight. The reaction mixture was cooled to room temperature, and the solvent was removed under reduced pressure. The residue was purified by column chromatography on silica gel (hexane:ethyl acetate=1:2) to give a 1:1 mixture of ethyl 4-(1-hydroxy-(4,5-methylenedioxy-2-nitrophenyl)methyl)-1-(4-methoxybenzyl)-1,2,3-triazole-5-carboxylate (a-1: low polar product (LP)) and ethyl 5-(1-hydroxy-(4,5-methylenedioxy-2-nitrophenyl)methyl)-1-(4-methoxybenzyl)-1,2,3-triazole-4-carboxylate (a-2: high polar product (MP)) (6.42 g, 55%).

1:1 mixture of a-1 (LP) and a-2 (MP):
$^1$H-NMR (CDCl$_3$): δ 1.36 (3/2H, t), 1.39 (3/2H, t), 3.71 (3/2H, s), 3.77 (3/2H, s), 4.38–4.44 (2H, m), 5.29 (1/2H, d), 5.49 (1/2H, d), 5.70 (1/2H, d), 5.79 (1/2H, d), 5.86 (1H, s), 6.00 (1H, d), 6.13 (1H, d), 6.65 (1H, d), 6.81–6.85 (2H, m), 6.95 (1/2H, d), 7.02 (1H, d), 7.20 (1H, d), 7.35 (1/2H, s), 7.44 (1/2H, s), 7.58 (1/2H, s).
FDMS: m/z 456 (M$^+$).

(b) A 1:1 mixture of the compound (a-1) and the compound (a-2) (6.40 g, 13.76 mmol) prepared in the step (a) was dissolved in methylene chloride (130 ml), active manganese dioxide (25 g) was added thereto, and the mixture was stirred at room temperature overnight. The reaction mixture was filtered through Celite and the Celite was washed with methylene chloride, and the solvent was removed under reduced pressure to give a 1:1 mixture of ethyl 4-(4,5-methylenedioxy-2-nitrobenzoyl)-1-(4-methoxybenzyl)-1,2,3-triazole-5-carboxylate (b-1: LP) and ethyl 5-(4,5-methylenedioxy-2-nitrobenzoyl)-1-(4-methoxybenzyl)-1,2,3-triazole-4-carboxylate (b-2: MP) as a foam (5.91 g, 95%).

1:1 mixture of b-1 (LP) and b-2 (MP):
$^1$H-NMR (CDCl$_3$): δ 1.25 (3/2H, t), 1.38 (3/2H, t), 3.80 (3H, s), 4.15 (1H, q), 4.43 (1H, q), 5.73 (1H, s), 5.80 (1H, s), 6.22 (2H, d), 6.78 (1/2H, s), 6.89 (1H, d), 6.91 (1H, d), 6.96 (1/2H, s), 7.25 (1H, d), 7.42 (1H, d), 7.46 (1/2H, s), 7.63 (1/2H, s).
EIMS: m/z 454 (M$^+$).

(c) The 1:1 mixture of ethyl 4-(4,5-methylenedioxy-2-nitrobenzoyl)-1-(4-methoxybenzyl)-1,2,3-triazole-5-carboxylate (b-1: LP) and ethyl 5-(4,5-methylenedioxy-2-nitrobenzoyl)-1-(4-methoxybenzyl)-1,2,3-triazole-4-carboxylate (b-2: MP) (5.90 g, 12.74 mmol) prepared in the step (b) was dissolved in ethyl acetate (130 ml), 10% palladium on carbon (590 mg) was added thereto, and the mixture was stirred at room temperature under a hydrogen atmosphere for 16 hr. The reaction mixture was filtered through Celite, and the filtrate was concentrated under reduced pressure to give a 1:1 mixture of ethyl 4-(2-amino-4,5-methylenedioxybenzoyl)-1-(4-methoxybenzyl)-1,2,3-triazole-5-carboxylate (c-1: LP) and ethyl 5-(2-amino-4,5-methylenedioxybenzoyl)-1-(4-methoxybenzyl)-1,2,3-triazole-4-carboxylate (c-2: MP) as a yellow oil (5.28 g, 96%).

1:1 mixture of c-1 (LP) and c-2 (MP):
$^1$H-NMR (CDCl$_3$): δ 1.12–1.29 (3H, m), 3.71 (3/2H, s), 3.81 (3/2H, s), 4.23 (2H, q), 5.25–5.80 (2H, brs), 5.83–5.90 (7/2H, m), 6.18 (1/2H, s), 6.65–6.69 (2H, m), 6.79 (1H, s), 6.88 (1H, d), 7.04 (1/2H, d), 7.08 (1/2H, d), 7.35 (1H, d).
EIMS: m/z 424 (M$^+$).

(d) The 1:1 mixture of ethyl 4-(2-amino-4,5-methylenedioxybenzoyl)-1-(4-methoxybenzyl)-1,2,3-triazole-5-carboxylate (c-1: LP) and ethyl 5-(2-amino-4,5-methylenedioxybenzoyl)-1-(4-methoxybenzyl)-1,2,3- triazole-4-carboxylate (c-2: MP) (5.16 g, 11.93 mmol) prepared in the step (c) was dissolved in methanol (60 ml), a solution of 28% sodium methoxide in methanol (2.6 ml, 13.12 mmol) was added to the solution, and the mixture was stirred at room temperature for 4 hr. Water was added to the reaction mixture, and the resultant precipitate was collected by filtration, washed with diethyl ether, and dried to give a 1:1 mixture of 7,8-methylenedioxy-3-(4-methoxybenzyl)-4 (5H),10-dioxo-3H-1,2,3-triazolo[4,5-c][1]benzazepine (d-1: LP) and 7,8-methylenedioxy-1-(4-methoxybenzyl)-4(5H), 10-dioxo-1H-1,2,3-triazolo[4,5-c][1]benzazepine (d-2: MP) as yellow crystalline powder (2.77 g, 60%).

1:1 mixture of d-1 (LP) and d-2 (MP):
$^1$H-NMR (DMSO-d$_6$):δ 3.70–3.73 (3H, m), 5.95–6.40 (1H, m), 6.06 (1H, s), 6.17 (2H, s), 6.89 (2H, d), 7.06 (1H, s), 7.28 (2H, d), 7.59 (1H, s), 11.30–11.53 (1H, brs).
FDMS: m/z 378 (M$^+$).

(e) Anisole (5 ml) and trifluoroacetic acid (20 ml) were added to the 1:1 mixture of 7,8-methylenedioxy-3-(4-methoxybenzyl)-4(5H),10-dioxo-3H-1,2,3-triazolo[5,4-c] [1]benzazepine (d-1: LP) and 7,8-methylenedioxy-1-(4-methoxybenzyl)-4(5H),10-dioxo-1H-1,2,3-triazolo[4,5-c] [1]benzazepine (d-2: MP) (0.50 g, 1.29 mmol) prepared in the step (d), and the mixture was stirred at 70° C. for one hr. Trifluoroacetic acid was removed from the reaction mixture under reduced pressure, isopropyl ether was added to the residue, and the resultant powder as a precipitate was collected by filtration and dried to give 7,8-methylenedioxy-4(5H),10-dioxo-1H-1,2,3-triazolo[4,5-c][1]benzazepine as yellow crystalline powder (317 mg, 95%).
$^1$H-NMR (DMSO-d$_6$):δ 6.16 (2H, s), 7.06 (1H, s), 7.60 (1H, s), 11.28 (1H, s).
FDMS: m/z 258 (M$^+$).

Example 27
8-(4-Methoxyphenacyloxy)-7-methyl-4(5H),10-dioxo-1H-1,2,3-triazolo[4,5-c][1]benzazepine (a) To a solution of diisopropylamine (6.1 ml, 43.5 mmol) in tetrahydrofuran (60 ml) was added, at −78° C. under an argon atmosphere, a 1.5 N butyllithium hexane solution (27.4 ml, 41.1 mmol). The mixture was stirred for 30 min. A solution of ethyl propiolate (3.4 ml, 33.5 mmol) in tetrahydrofuran (10 ml) and a solution of 5-methoxymethoxy-4-methyl-2-nitrobenzaldehyde (5.45 g, 24.2 mmol) in tetrahydrofuran (50 ml) were added to the reaction mixture in that order, and the mixture was stirred at −78° C. for additional 1.5 hr. A solution of acetic acid (4.2 ml, 73.3 mmol) in tetrahydrofuran (10 ml) was then added to the reaction mixture, water was then added thereto, and the organic solvent was removed under reduced pressure. The residue was extracted with ethyl acetate. The organic layer was washed with dilute hydrochloric acid, a saturated aqueous sodium bicarbonate solution, and saturated brine in that order. It was then dried over anhydrous magnesium sulfate. The solvent was removed under reduced pressure to give ethyl 4-hydroxy-4-(5-methoxymethoxy-4-methyl-2-nitrophenyl)-2-butynoate as a brown oil. Ethyl 4-hydroxy-4-(5-methoxymethoxy-4-methyl-2-nitrophenyl)-2-butynoate was dissolved in toluene (30 ml), 4-methoxybenzylazide (11.8 g, 72.3 mmol) was added to the solution, and the mixture was stirred at 100° C. overnight. The reaction mixture was cooled to room temperature, and the solvent was removed under reduced pressure. The residue was purified by column chromatography on silica gel (hexane:ethyl acetate=3:2) to give a 1:1 mixture of ethyl 4-(hydroxy-(5-methoxymethoxy-4-methyl-2-nitrophenyl) methyl)-1-(4-methoxybenzyl)-1,2,3-triazole-5-carboxylate (a-1: low polar product (LP)) and ethyl 5-(hydroxy-(5-methoxymethoxy-4-methyl-2-nitrophenyl)methyl)-1-(4-methoxybenzyl)-1,2,3-triazole-4-carboxylate (a-2: high polar product (MP)) as a brown crystal (7.57 g, 64%).

1:1 mixture of a-1 (LP) and a-2 (MP):
$^1$H-NMR (CDCl$_3$): δ 1.36 (3/2H, t), 1.40 (3/2H, t), 2.20 (3/2H, s), 2.30 (3/2H, s), 3.35 (3/2H, s), 3.48 (3/2H, s), 3.70 (1/2H, d), 3.71 (3/2H, s), 3.78 (3/2H, s), 4.37–4.46 (2H, m), 4.88 (1/2H, d), 4.93 (1/2H, d), 5.26 (1/2H, d), 5.33 (1/2H, d), 5.35 (1/2H, d), 5.47 (1/2H, d), 5.67 (1/2H, d), 5.77 (1/2H, d), 5.83 (1/2H, d), 6.52 (1/2H, s), 6.64 (1H, d), 6.83 (1H, d), 6.92 (1/2H, d), 7.03 (1/2H, d), 7.00 (1H, d), 7.20 (1H, d), 7.61 (1/2H, s), 7.78 (1/2H, s), 8.01 (1/2H, s).
EIMS: m/z 486 (M$^+$).

(b) The 1:1 mixture of ethyl 4-(hydroxy-(5-methoxymethoxy-4-methyl-2-nitrophenyl)methyl)-1-(4-methoxybenzyl)-1,2,3-triazole-5-carboxylate (a-1: LP) and ethyl 5-(hydroxy-(5-methoxymethoxy-4-methyl-2-nitrophenyl)methyl)-1-(4-methoxybenzyl)-1,2,3-triazole-4-carboxylate (a-2: MP) (7.57 g, 15.6 mmol) prepared in the step (a) was dissolved in methylene chloride (150 ml), active manganese dioxide (22.7 g) was added to the solution, and the mixture was stirred at room temperature overnight. The reaction mixture was filtered through Celite and the Celite was washed with ethyl acetate, and the solvent was removed under reduced pressure to give a 1:1 mixture of ethyl 1-(4-methoxybenzyl)-4-(5 -methoxymethoxy-4-methyl-2-nitrobenzoyl)-1,2,3-triazole-5-carboxylate (b-1: LP) and ethyl 1-(4-methoxybenzyl)-5-(5-methoxymethoxy-4-methyl-2-nitrobenzoyl)-1,2,3-triazole-4-carboxylate (b-2: MP) as an orange oil (7.30 g, 97%).

1:1 mixture of b-1 (LP) and b-2 (MP):
$^1$H-NMR (CDCl$_3$): δ 1.15 (3/2H, t), 1.37 (3/2H, t), 2.34 (3/2H, s), 2.35 (3/2H, s), 3.46 (3/2H, s), 3.47 (3/2H, s), 3.78 (3/2H, s), 3.79 (3/2H, s), 4.05 (1H, q), 4.42 (1H, q), 5.22 (1H, s), 5, 29 (1H, s), 5.71 (1H, s), 5.82 (1H, s), 6.84–6.92 (2H, m), 7.00 (1/2H, s), 7.18 (1/2H, s), 7.24 (1H, d), 7.41 (1H, d), 7.91 (1/2H, s), 8.04 (1/2H, s).
EIMS: m/z 484 (M$^+$).

(c) The 1:1 mixture of ethyl 1-(4-methoxybenzyl)-4-(5-methoxymethoxy-4-methyl-2-nitrobenzoyl)-1,2,3-triazole-5-carboxylate (b-1: LP) and ethyl 1-(4-methoxybenzyl)-5-(5-methoxymethoxy-4-methyl-2-nitrobenzoyl)-1,2,3-triazole-4-carboxylate (b-2: MP) (6.31 g, 13.0 mmol) prepared in the step (b) was dissolved in ethyl acetate (100 ml), 10% palladium on carbon (631 mg) was added thereto, and the mixture was stirred at room temperature under a hydrogen atmosphere for 20 hr. The reaction mixture was filtered through Celite, and the filtrate was concentrated under reduced pressure to give a 1:1 mixture of ethyl 4-(2-amino-5-methoxymethoxy-4-methylbenzoyl)-1-(4-methoxybenzyl)-1,2,3-triazole-5-carboxylate (c-1: LP) and ethyl 5-(2-amino-5-methoxymethoxy-4-methylbenzoyl)-1-(4-methoxybenzyl)-1,2,3-triazole-4-carboxylate (c-2: MP) (5.87 g, 99%).

1:1 mixture of c-1 (LP) and c-2 (MP):
$^1$H-NMR (CDCl$_3$): δ 1.05 (3/2H, t), 1.12 (3/2H, t), 2.17 (3/2H, s), 2.21 (3/2H, s), 3.29 (3/2H, s), 3.32 (3/2H, s), 3.68 (3/2H, s), 3.79 (3/2H, s), 4.09–4.25 (2H, m), 4.71 (1H, s), 4.92 (1H, s), 5.40–5.60 (1H, brs), 5.85 (1H, s), 6.32 (1/2H, s), 6.47 (1/2H, s), 6.52 (1/2H, s), 6.67 (1H, d), 6.86 (1H, d), 7.05 (1/2H, s), 7.07 (1H, d), 7.32 (1H, d).
EIMS: m/z 454 (M$^+$).

(d) Under an argon atmosphere, the 1:1 mixture of ethyl 4-(2-amino-5-methoxymethoxy-4-methylbenzoyl)-1-(4-methoxybenzyl)-1,2,3-triazole-5-carboxylate (c-1: LP) and ethyl 5-(2-amino-5-methoxymethoxy-4-methylbenzoyl)-1-(4-methoxybenzyl)-1,2,3-triazole-4-carboxylate (c-2: MP)

(5.72 g, 12.6 mmol) was dissolved in dimethylsulfoxide (100 ml), a solution of 28% sodium methoxide in methanol (2.7 ml, 13.8 mmol) was added to the solution, and the mixture was stirred at room temperature for one hr. Water was added to the reaction mixture to precipitate a crystal, followed by addition of hydrochloric acid to bring the pH value to the acidic side. The crystal was collected by filtration and then dried to give a 1:1 mixture of 3-(4-methoxybenzyl)-8-methoxymethoxy-7-methyl-4(5H),10-dioxo-3H-1,2,3-triazolo[4,5-c][1]benzazepine (d-1: LP) and 1-(4-methoxybenzyl)-8-methoxymethoxy-7-methyl-4(5H),10-dioxo-1H-1,2,3-triazolo[4,5-c][1]benzazepine (d-2: MP) (4.11 g, 80%).

1:1 mixture of d-1 (LP) and d-2 (MP):

$^1$H-NMR (DMSO-d$_6$): δ 2.24 (3/2H, s), 2.25 (3/2H, s), 3.40 (3H, s), 3.71 (3H, s), 5.28 (2H, s), 6.00 (1H, s), 6.10 (1H, s), 6.86–6.97 (2H, m), 7.25–7.34 (5/2H, m), 7.37 (1/2H, s), 7.77 (1/2H, s), 7.80 (1/2H, s), 11.30 (1H, s).

EIMS: m/z 408 (M$^+$).

(e) Trifluoroacetic acid (2.8 ml) was added to a solution of the 1:1 mixture of 3-(4-methoxybenzyl)-8-methoxymethoxy-7-methyl-4(5H),10-dioxo-3H-1,2,3-triazolo[4,5-c][1]benzazepine (d-1: LP) and 1-(4-methoxybenzyl)-8-methoxymethoxy-7-methyl-4(5H),10-dioxo-1H-1,2,3-triazolo[4,5-c][1]benzazepine (d-2: MP) (1.50 g, 3.67 mmol), in methylene chloride (30 ml), and the mixture was stirred at room temperature for 4 hr. Diethyl ether was added to the reaction mixture, and the resultant crystal as a precipitate was collected by filtration and then dried to give a mixture (e) of 8-hydroxy-1-(4-methoxybenzyl)-7-methyl-4(5H), 10-dioxo-1H-1,2,3-triazolo[4,5-c][1]benzazepine and position isomers of triazole portion of the 4-methoxybenzyl (three kinds in total) as light yellow powder (1.34 g, 96%).

(f) 8-Hydroxy-1-(4-methoxybenzyl)-7-methyl-4(5H),10-dioxo-1H-1,2,3-triazolo[4,5-c][1]benzazepine (e) (154 mg, 0.405 mmol) was dissolved in N,N-dimethylformamide (4 ml). Potassium carbonate (112 mg, 0.810 mmol) and 4-methoxyphenacyl bromide (186 mg, 0.812 mmol) were added to the solution, and the mixture was stirred at room temperature overnight. Excess water was added to the reaction mixture, and the resultant precipitate was collected by filtration and dried to give 1-(4-methoxybenzyl)-8-(4-methoxyphenacyloxy)-7-methyl-4(5H),10-dioxo-1H-1,2,3-triazolo[4,5-c][1]benzazepine (f) (208 mg, 100%).

SIMS: m/z 513(M$^+$+1).

(g) Anisole (0.4 ml) and trifluoroacetic acid (4.0 ml) were added to 1-(4-methoxybenzyl)-8-(4-methoxyphenacyloxy)-7-methyl-4(5H),10-dioxo-1H-1,2,3-triazolo[4,5-c][1]benzazepine (f) (205 mg, 0.400 mmol), and the mixture was stirred at 60° C. for 2 hr. The solvent was removed under reduced pressure, and the resultant precipitate was collected by filtration and then dried to give the title compound: 8-(4-methoxyphenacyloxy)-7-methyl-4(5H),10-dioxo-1H-1,2,3-triazolo[4,5-c][1]benzazepine (g) (164 mg, 100%).

$^1$H-NMR (DMSO-d$_6$): δ 2.31 (3H, s), 3.87 (3H, s), 5.65 (2H, s), 7.11 (2H, d), 7.41 (1H, s), 7.58 (1H, s), 8.04 (2H, d), 11.33 (1H, s).

SIMS: m/z 393 (M$^+$+1).

(h) 8-(4-Methoxyphenacyloxy)-7-methyl-4(5H),10-dioxo-1H-1,2,3-triazolo[4,5-c][1]benzazepine (g) (50 mg, 0.127 mmol) was dissolved in dimethylsulfoxide (0.7 ml), a solution of 28% sodium methoxide in methanol (0.03 ml, 0.153 mmol) was added to the solution, and the mixture was stirred at room temperature for 20 min. Diethyl ether and methylene chloride were added to the reaction mixture, and the resultant crystal as a precipitate was collected by filtration and then dried. This crystal was purified on Diaion HP-20 to give a sodium salt (h) of the title compound: 8-(4-methoxyphenacyloxy)-7-methyl-4(5H),10-dioxo-1H-1,2,3-triazolo[4,5-c][1]benzazepine (g) (9 mg, 17%).

$^1$H-NMR (DMSO-d$_6$): δ 2.27 (3H, s), 3.87 (3H, s), 5.59 (2H, s), 7.11 (2H, d), 7.32 (1H, s), 7.59 (1H, s), 8.04 (2H, d), 10.45 (1H, s).

SIMS: m/z 393 (M$^+$—Na+H+1).

Example 28

8-Hydroxy-7-methyl-4(5H),10-dioxo-1H-1,2,3-triazolo[4,5-c][1]benzazepine

Anisole (0.4 ml) and trifluoroacetic acid (4.0 ml) were added to the 1:1 mixture of 3-(4-methoxybenzyl)-8-methoxymethoxy-7-methyl-4(5H),10-dioxo-3H-1,2,3-triazolo[4,5-c][1]benzazepine (d-1: LP) and 1-(4-methoxybenzyl)-8-methoxymethoxy-7-methyl-4(5H),10-dioxo-1H-1,2,3-triazolo[4,5-c][1]benzazepine (d-2: MP) (150 mg, 0.367 mmol) prepared in Example 27, and the mixture was stirred at 60° C. for one hr. The solvent was removed under reduced pressure, and the resultant precipitate was collected by filtration, washed with diethyl ether, and then dried to give the title compound: 8-hydroxy-7-methyl-4(5H),10-dioxo-1H-1,2,3-triazolo[4,5-c][1]benzazepine (89 mg, 99%).

$^1$H-NMR (DMSO-d$_6$): δ 2.19 (3H, s), 3.40 (1H, brs), 7.33 (1H, s), 7.70 (1H, s), 9.91 (1H, s), 11.22 (1H, brs).

FDMS: m/z 244 (M$^+$).

Example 29

6,8-Dimethyl-4(5H),10-dioxo-1H-1,2,3-triazolo[4,5-c][1]benzazepine (a) To a solution of diisopropylamine (2.3 ml, 16.4 mmol) in tetrahydrofuran (30 ml) was added, at −78° C. under an argon atmosphere, a 1.5 N butyllithium hexane solution (10.4 ml, 15.6 mmol). The mixture was stirred for 30 min. A solution of ethyl propiolate (1.3 ml, 12.8 mmol) in tetrahydrofuran (10 ml) and a solution of 2-(N-benzyloxycarbonyl)amino-3,5-dimethylbenzaldehyde (2.60 g, 9.18 mmol) in tetrahydrofuran (10 ml) were added in that order, and the mixture was stirred at −78° C. for additional 2 hr. A solution of acetic acid (1.6 ml, 28.0 mmol) in tetrahydrofuran (5 ml) was then added to the reaction mixture, water was added thereto, and the solvent was removed under reduced pressure. The residue was extracted with ethyl acetate. The organic layer was washed with dilute hydrochloric acid, water, a saturated aqueous sodium bicarbonate solution, and saturated brine in that order. It was then dried over anhydrous magnesium sulfate, and the solvent was removed under reduced pressure to give ethyl 4-(2-(N-benzyloxycarbonyl)amino-3,5-dimethylphenyl)-4-hydroxy-2-butynoate as an oil (4.39 g). Ethyl 4-(2-(N-benzyloxycarbonyl)amino-3,5-dimethylphenyl)-4-hydroxy-2-butynoate thus prepared was dissolved in toluene (10 ml), 4-methoxybenzylazide (4.5 g, 27.6 mmol) was added to the solution, and the mixture was stirred at 10° C. for 11 hr. The reaction mixture was cooled to room temperature, and the solvent was removed under reduced pressure. The residue was purified by column chromatography on silica gel (hexane:ethyl acetate=2:1) to give a 3:5 mixture of ethyl 4-(2-(N-benzyloxycarbonyl)amino-3,5-dimethylphenyl) hydroxymethyl-1-(4-methoxybenzyl)-1,2,3-triazole-5-carboxylate (a-1: low polar product (LP)) and ethyl 5-(2-(N-benzyloxycarbonyl)amino-3,5-dimethylphenyl) hydroxymethyl-1-(4-methoxybenzyl)-1,2,3-triazole-4-carboxylate (a-2: high polar product (MP)) (2.89 g, 58%).

3:5 mixture of a-1 (LP) and a-2 (MP):

$^1$H-NMR (CDCl$_3$): δ 1.15–1.45 (3H, m), 1.97 (9/8H, s), 2.18–2.35 (39/8H, m), 3.60–3.83 (3H, m), 3.82–3.93 (3/8H, m), 4.18–4.30 (3/4H, m), 4.35–4.45 (5/4H, m), 5.10–5.53 (4H, m), 5.75–6.00 (2H, m), 6.14 (5/8H, d), 6.32 (3/8H, d), 6.55–7.50 (11H, m).

SIMS: m/z 545 (M$^+$+1).

(b) The 3:5 mixture of ethyl 4-(2-(N-benzyloxycarbonyl) amino-3,5-dimethylphenyl)hydroxymethyl-1-(4-methoxybenzyl)-1,2,3-triazole-5-carboxylate (a-1: LP) and ethyl 5-(2-(N-benzyloxycarbonyl)amino-3,5-dimethylphenyl)hydroxymethyl-1-(4-methoxybenzyl)-1,2,3-triazole-4-carboxylate (a-2: MP) (2.82 g, 5.18 mmol) prepared in the step (a) was dissolved in methylene chloride (50 ml), active manganese dioxide (5.64 g) was added to the solution, and the mixture was stirred at room temperature for one hr. Further, active manganese dioxide (5.64 g) was added thereto, and the mixture was stirred at room temperature for four hr. The reaction mixture was filtered through Celite and the Celite was washed with ethyl acetate, and the solvent was removed under reduced pressure. The residue was purified by column chromatography on silica gel (hexane:ethyl acetate=2:1) to give an about 1:1 mixture of ethyl 4-(2-(N-benzyloxycarbonyl)amino-3,5-dimethylbenzoyl)-1-(4-methoxybenzyl)-1,2,3-triazole-5-carboxylate (b-1: LP) and ethyl 5-(2-(N-benzyloxycarbonyl)amino-3,5-dimethylbenzoyl)-1-(4-methoxybenzyl)-1,2,3-triazole-4-carboxylate (b-2: MP) as an orange oil (1.89 g, 67%).

1:1 mixture of b-1 (LP) and b-2 (MP):
$^1$H-NMR (CDCl$_3$): δ 0.98 (3/2H, t), 1.01 (3/2H, t), 2.08 (3/2H, s), 2.27 (3/2H, s), 2.28 (3/2H, s), 2.29 (3/2H, s), 3.67 (3/2H, s), 3.78 (3/2H, s), 4.05–4.16 (2H, m), 5.09 (1H, s), 5.15 (1H, s), 5.50 (1H, s), 5.79 (1H, s), 6.39 (1/2H, d), 6.65 (1H, d), 6.86 (1H, d), 7.04 (1H, d), 7.20 (1/2H, d), 7.23–7.45 (14H, m), 7.90 (1/2H, s), 8.35 (1/2H, s).

EIMS: m/z 543 (M$^+$).

(c) The 1:1 mixture of ethyl 4-(2-(N-benzyloxycarbonyl) amino-3,5-dimethylbenzoyl)-1-(4 -methoxybenzyl)-1,2,3-triazole-5-carboxylate (b-1: LP) and ethyl 5-(2-(N-benzyloxycarbonyl)amino-3,5-dimethylbenzoyl)-1-(4-methoxybenzyl)-1,2,3-triazole-4-carboxylate (b-2: MP) (1.88 g, 3.46 mmol) prepared in the step (b) was dissolved in ethyl acetate (30 ml), 10% palladium on carbon (188 mg) was added to the solution, and the mixture was stirred at room temperature under a hydrogen atmosphere for 4.5 hr. The reaction mixture was filtered through Celite, and the filtrate was concentrated under reduced pressure to give an about 1:1 mixture of ethyl 4-(2-amino-3,5-dimethylbenzoyl)-1-(4-methoxybenzyl)-1,2,3-triazole-5-carboxylate (c-1: LP) and ethyl 5-(2-amino-3,5-dimethylbenzoyl)-1-(4-methoxybenzyl)-1,2,3-triazole-4-carboxylate (c-2: MP) (1.43 g, 100%).

1:1 mixture of c-1 (LP) and c-2 (MP):
$^1$H-NMR (CDCl$_3$): δ 1.06 (3/2H, t), 1.12 (3/2H, t), 1.93 (3/2H, s), 2.12 (3/2H, s), 2.17 (3/2H, s), 2.18 (3/2H, s), 3.69 (3/2H, s), 3.80 (3/2H, s), 4.17 (1H, q), 4.22 (1H, q), 5.43 (1H, brs), 5.86 (1H, s), 6.26 (1/2H, s), 6.35 (1/2H, s), 6.39 (1/2H, s), 6.65 (1H, d), 6.87 (1H, d), 7.00 (1/2H, s), 7.04–7.10 (1/2H, m), 7.06 (1H, d), 7.36 (1H, d).

EIMS: m/z 408 (M$^+$).

(d) Under an argon atmosphere, a solution of 28% sodium methoxide in methanol (0.74 ml, 3.77 mmol) was added to a solution of the 1:1 mixture of ethyl 4-(2-amino-3,5-dimethylbenzoyl)-1-(4-methoxybenzyl)-1,2,3-triazole-5-carboxylate (c-1: LP) and ethyl 5-(2-amino-3,5-dimethylbenzoyl)-1-(4-methoxybenzyl)-1,2,3-triazole-4-carboxylate (c-2: MP) (1.41 g, 3.45 mmol) in methanol (10 ml), and the mixture was stirred at room temperature for 5 hr. Water was added to the reaction mixture, and the resultant crystal as a precipitate was collected by filtration and dried to give a 1:1 mixture of 3-(4-methoxybenzyl)-6,8-dimethyl-4(5H),10-dioxo-3H-1,2,3-triazolo[4,5-c][1]benzazepine (d-1: LP) and 1-(4 -methoxybenzyl)-6,8-dimethyl-4(5H),10-dioxo-1H-1,2,3-triazolo[4,5-c][1]benzazepine (d-2: MP) (917 mg, 73%).

1:1 mixture of d-1 (LP) and d-2 (MP):
$^1$H-NMR (DMSO-d$_6$): δ 2.31 (3H, s), 2.44 (3/2H, s), 2.47 (3/2H, s), 3.71 (3/2H, s), 3.72 (3/2H, s), 5.88 (1H, s), 6.01 (1H, s), 6.90 (2H, d), 7.28 (1H, d), 7.34 (1H, d), 7.40 (1/2H, s), 7.45 (1/2H, s), 7.65 (1/2H, s), 7.70 (1/2H, s), 9.85 (1H, s).

SIMS: m/z 363 (M$^+$+1).

(e) Anisole (0.5 ml) and trifluoroacetic acid (5.0 ml) were added to the 1:1 mixture of 3-(4-methoxybenzyl)-6,8-dimethyl-4(5H),10-dioxo-3H-1,2,3-triazolo[4,5-c][1]benzazepine (d-1: LP) and 1-(4-methoxybenzyl)-6,8-dimethyl-4(5H),10-dioxo-1H-1,2,3-triazolo[4,5-c][1]benzazepine (d-2: MP) (300 mg, 0.828 mmol), and the mixture was stirred at 60° C. for 2 hr. The solvent was removed under reduced pressure, and the resultant crystal as a precipitate was collected by filtration, washed with diethyl ether and methylene chloride, and then dried to give the title compound: 6,8-dimethyl-4(5H),10-dioxo-1H-1,2,3-triazolo [4,5-c][1]benzazepine (e') (137 mg, 68%). A 1 N aqueous sodium hydroxide solution was added to 6,8-dimethyl-4 (5H),10-dioxo-1H-1,2,3-triazolo[4,5-c][1]benzazepine (e') (127 mg, 0.524 mmol), and the solution was purified on Diaion HP-20 to give a sodium salt of the title compound: 6,8-dimethyl-4(5H),10-dioxo-1H-1,2,3-triazolo[4,5-c][1]benzazepine (e) as light yellow powder (119 mg, 86%).

e':
$^1$H-NMR (DMSO-d$_6$): δ 2.32 (3H, s), 2.49 (3H, s), 7.46 (1H, s), 7.81 (1H, s), 9.53 (1H, s).

EIMS: m/z 242 (M$^+$).

e:
$^1$H-NMR (DMSO-d$_6$): δ 2.30 (3H, s), 2.46 (3H, s), 7.32 (1H, s), 7.78 (1H, s), 8.66 (1H, s).

FDMS: m/z 265 (M$^+$+1).

Example 30

6,7,8-Trimethoxy-4(5H),10-dioxo-1H-1,2,3-triazolo[4,5-c] [1]benzazepine (a) A 1.0 M solution of diisobutylaluminum hydride in tetrahydrofuran (19.7 ml, 19.7 mmol) was added to a solution of methyl 3,4,5-trimethoxy-2-nitrobenzoate (5.0 g, 18.5 mmol) in toluene (100 ml) at −50° C. under an argon atmosphere, and the mixture was stirred for 30 min. Methanol (10 ml) was added thereto, and the temperature of the mixture was raised to room temperature. Water was added to the mixture, followed by extraction twice with ethyl acetate. The organic layer was dried over anhydrous magnesium sulfate, and the solvent was removed under reduced pressure. The residue was purified by column chromatography on silica gel (hexane:ethyl acetate=2:1) to give 3,4,5-trimethoxy-2-nitrobenzyl alcohol (1.01 g, 23%) as light yellow powder.

$^1$H-NMR (CDCl$_3$): δ 3.82 (3H, s), 3.87 (3H, s), 3.92 (3H, s), 4.55 (2H, d), 6.77 (1H, s).

(b) Active manganese dioxide (8.0 g) was added to a solution of 3,4,5-trimethoxy-2-nitrobenzyl alcohol (1.01 g, 4.15 mmol), prepared in the step (a), in methylene chloride (15 ml), and the mixture was stirred at room temperature overnight. Further, active manganese dioxide (8.0 g) was added thereto, and the mixture was stirred at room temperature for 8 hr. The reaction mixture was filtered through Celite, and the solvent was removed under reduced pressure to give 3,4,5-trimethoxy-2-nitrobenzaldehyde (300 mg, 30%) as colorless powder.

¹H-NMR (CDCl₃): δ 3.98 (3H, s), 4.00 (6H, s), 4.00 (3H, s), 9.88 (1H, s).

EIMS: m/z 241 (M⁺).

(c) A 1.0 M solution (1.9 ml) of lithium bistrimethylsilylamide in tetrahydrofuran was added to tetrahydrofuran (4.0 ml) at −78° C. under an argon atmosphere, and the mixture was stirred for 30 min. A solution of ethyl propiolate (176 µl, 1.74 mmol) in tetrahydrofuran (1.0 ml) was added thereto, and the mixture was stirred for 30 min. A solution of 3,4,5-trimethoxy-2-nitrobenzaldehyde (280 mg, 1.16 mmol), prepared in the step (b), in tetrahydrofuran (2.5 ml) was added thereto, and the temperature was raised to −58° C., followed by stirring for 30 min. The reaction mixture was poured into an ice-cold 10% aqueous ammonium chloride solution, and the mixture was vigorously stirred for 5 min. The reaction mixture was extracted with ethyl acetate, and the organic layer was washed with saturated brine and dried over anhydrous magnesium sulfate. The solvent was removed under reduced pressure to give ethyl 4-hydroxy-4-(3,4,5-trimethoxy-2-nitrophenyl)-2-butynoate as an oil (268 mg, 68%).

¹H-NMR (CDCl₃): δ 1.32 (3H, t), 3.91 (3H, s), 3.96 (3H, s), 3.99 (3H, s), 4.25 (2H, q), 5.71 (1H, s), 7.04 (1H, s).

EIMS: m/z 339 (M⁺).

(d) A reaction was performed in the same manner as in the step (b) of Example 20, except that ethyl 4-hydroxy-4-(3,4,5-trimethoxy-2-nitrophenyl)-2-butynoate (268 mg, 0.78 mmol) prepared in the step (c) and 4-methoxybenzylazide (322 mg, 1.97 mmol) were used. Thus, a 1:1 mixture of ethyl 4-(hydroxy-(3,4,5-trimethoxy-2-nitrophenyl)methyl)-1-(4-methoxybenzyl)-1,2,3-triazole-5-carboxylate and ethyl 5-(hydroxy-(3,4,5-trimethoxy-2-nitrophenyl)methyl)-1-(4-methoxybenzyl)-1,2,3-triazole-4-carboxylate (350 mg, 89%) was prepared.

¹H-NMR (CDCl₃): δ 1.32 (3/2H, t), 1.41 (3/2H, t), 3.43 (3H, s), 3.69 (3/2H, s), 3.77 (3/2H, s), 3.83 (3/2H, s), 3.88 (3/2H, s), 3.96 (3/2H, s), 3.97 (3/2H, s), 4.41 (2H, m), 5.41 (1/2H, d), 5.48 (1/2H, d), 5.64 (1/2H, d), 5.67 (1/2H, d), 5.82 (1H, d), 6.37 (1/2H, d), 6.45 (1/2H, d), 6.65 (1H, d), 6.84 (1H, d), 6.97 (1/2H, s), 7.11 (1H, d), 7.24 (1H, d), 7.26 (1/2H, s).

EIMS: m/z 502 (M⁺).

(e) A reaction was performed in the same manner as in the step (b) of Example 20, except that the 1:1 mixture of ethyl 4-(hydroxy-(3,4,5-trimethoxy-2-nitrophenyl)methyl)-1-(4-methoxybenzyl)-1,2,3-triazole-5-carboxylate and ethyl 5-(hydroxy-(3,4,5-trimethoxy-2-nitrophenyl)methyl)-1-(4-methoxybenzyl)-1,2,3-triazole-4-carboxylate (320 mg, 0.64 mmol) prepared in the step (d) and active manganese dioxide (1.0 g) were used. Thus, a 1:1 mixture of ethyl 1-(4-methoxybenzyl)-4-(3,4,5-trimethoxy-2-nitrobenzoyl)-1,2,3-triazole-5-carboxylate and ethyl 1-(4-methoxybenzyl)-5-(3,4,5-trimethoxy-2-nitrobenzoyl)-1,2,3-triazole-4-carboxylate (300 mg, 94%).

¹H-NMR (CDCl₃): δ 1.32 (3/2H, t), 1.29 (3/2H, t), 3.60 (3/2H, s), 3.70 (3/2H, s), 3.79 (3/2H, s), 3.92 (3/2H, s), 3.96 (3/2H, s), 3.97 (3/2H, s), 3.98 (3/2H, s), 4.00 (3/2H, s), 4.19 (1H, q), 4.35 (1H, q), 5.59 (1H, s), 5.75 (1H, s), 6.14 (1/2H, s), 6.72 (1H, d), 6.87 (1H, d), 7.18 (1/2H, d), 7.25 (1/2H, s), 7.28 (1/2H, d).

EIMS: m/z 500 (M⁺).

(f) The 1:1 mixture of ethyl 1-(4-methoxybenzyl)-4-(3,4,5-trimethoxy-2-nitrobenzoyl)-1,2,3-triazole-5-carboxylate and ethyl 1-(4-methoxybenzyl)-5-(3,4,5-trimethoxy-2-nitrobenzoyl)-1,2,3-triazole-4-carboxylate (300 mg, 0.60 mmol) prepared in the step (e) was catalytically hydrogenated in the presence of 10% palladium on carbon (30 mg) in the same manner as in the step (c) of Example 20 to give a 1:1 mixture of ethyl 4-(2-amino-3,4,5-trimethoxybenzoyl)-1-(4-methoxybenzyl)-1,2,3-triazole-5-carboxylate and ethyl 5-(2-amino-3,4,5-trimethoxybenzoyl)-1-(4-methoxybenzyl)-1,2,3-triazole-4-carboxylate (285 mg). A reaction was allowed to proceed in the same manner as in the step (d) of Example 20, except that a solution of this mixture (285 mg) in methanol (5 ml) and a solution of 28% sodium methoxide in methanol (130 µl, 0.66 mmol) were used. Thus, a 1:1 mixture of 6,7,8-trimethoxy-1-(4-methoxybenzyl)-4(5H),10-dioxo-1H-1,2,3-triazolo[4,5-c][1]benzazepine and 6,7,8-trimethoxy-3-(4-methoxybenzyl)-4(5H),10-dioxo-3H-1,2,3-triazolo[4,5-c][1]benzazepine (141.8 mg, 55%) was prepared.

¹H-NMR (DMSO-d₆): δ 3.73 (3H, s), 3.91 (3/2H, s), 3.92 (3/2H, s), 3.94 (3/2H, s), 3.96 (3/2H, s), 3.97 (3/2H, s), 3.98 (3/2H, s), 6.07 (2H, d), 6.87 (2H, d), 7.33 (1H, d), 7.34 (1H, d), 9.43 (1/2H, s), 9.60 (1/2H, s)

EIMS: m/z 424 (M⁺).

(g) The mixture of 6,7,8-trimethoxy-1-(4-methoxybenzyl)-4(5H),10-dioxo-1H-1,2,3-triazolo[4,5-c][1]benzazepine and 6,7,8-trimethoxy-3-(4-methoxybenzyl)-4(5H),10-dioxo-3H-1,2,3-triazolo[4,5-c][1]benzazepine (120 mg, 0.28 mmol) prepared just above was deprotected using anisole (0.5 ml) and trifluoroacetic acid (5.0 ml) in the same manner as in the step (b) of Example 1, followed by treatment with a 1 N aqueous sodium hydroxide solution to form a sodium salt. The sodium salt was purified on Diaion HP-20 (water:acetone=4:1) to give the title compound: 6,7,8-trimethoxy-4(5H), 10-dioxo-1H-1,2,3-triazolo[4,5-c][1]benzazepine (96 mg, 88%) as light yellow powder.

¹H-NMR (D₂O): (3.52 (3H, s), 3.78 (6H, s), 6.86 (1H, s).

EIMS: m/z 304 (M⁺).

Example 31

4(5H),10-Dioxo-7-(2-(3-pyridyl)ethenyl)-1H-1,2,3-triazolo[4,5-c][1]benzazepine trifluoroacetate (E:Z=1:2)

(a) Triphenyl-3-pyridylmethylphosphonium chloride hydrochloride (209 mg, 0.49 mmol) was suspended in toluene (5 ml) and N,N-dimethylformamide (2 ml) under an argon atmosphere, and potassium tert-butoxide (110 mg, 0.98 mmol) was added to the suspension. Subsequently, 7-formyl-1-(4-methoxybenzyl)-4(5H),10-dioxo-1H-1,2,3-triazolo[4,5-c][1]benzazepine (150 mg, 0.41 mmol) was added thereto, and the mixture was heated at 70° C. for 6 hr. Water was added to the reaction mixture, and the resultant brown crystalline powder was collected by filtration, washed with diethyl ether, and then dried to give 1-(4-methoxybenzyl)-4(5H),10-dioxo-7-(2-(3-pyridyl)ethenyl)-1H-1,2,3-triazolo[4,5-c][1]benzazepine (E:Z=1:2) (137 mg, 76%).

¹H-NMR (DMSO-d₆): δ 3.71 (3H, s), 5.98 (4/3H, s), 6.01 (2/3H, s), 6.81 (2/3H, d), 6.85 (2/3H, d), 6.90 (4/3H, d), 6.91 (2H, d), 7.07 (2/3H, d), 7.28 (4/3H, d), 7.22–7.35 (1H, m), 7.40 (1/3H, d), 7.44 (4/3H, s), 7.46 (1/3H, d), 7.58 (2/3H, d), 7.636 (1/3H, dd), 7.66 (1/3H, s), 8.07 (2/3H, d), 8.15 (1/3H, d), 8.20 (1/3H, d), 8.41 (2/3H, s), 8.44 (2/3H, s), 8.53 (1/3H, d), 8.84 (1/3H, s), 11.32 (1/3H, s), 11.40 (1/3H, s).

SIMS: m/z 438 (M⁺+1).

(b) To a mixed solvent composed of anisole (0.3 ml) and trifluoroacetic acid (3 ml) was dissolved 1-(4-methoxybenzyl)-4(5H),10-dioxo-7-(2-(3-pyridyl)ethenyl)-1H-1,2,3-triazolo[4,5-c][1]benzazepine (E:Z=1:2) (133.2 mg, 0.30 mmol) prepared in the step (a). The solution was heated at 60° C. for 30 min. The solvent was removed under reduced pressure, and the resultant crystal as a precipitate was collected by filtration, washed with diethyl ether, and then dried to give the title compound: 4(5H),10-dioxo-7-(2-

(3-pyridyl)ethenyl)-1H-1,2,3-triazolo[4,5-c][1]benzazepine trifluoroacetate (E:Z=1:2) as yellow crystalline powder (122.4 mg, 93%).

$^1$H-NMR (DMSO-$d_6$): δ 6.88 (2/3H, d), 6.92 (2/3H, d), 7.09 (2/3H, d), 7.45–7.75 (4/3H, m), 7.49 (1/3H, d), 7.50–7.60 (2/3H, m), 7.69 (1/3H, d), 7.60–7.75 (4/311, m), 7.85 (2/3H, d), 8.21 (2/3H, d), 8.33 (1/3H, d), 8.41 (1/3H, d), 8.53–8.62 (4/3H, d), 8.62–8.69 (1/3H, m), 8.97 (1/3H, d), 11.35 (2/3H, s), 11.49 (1/3H, s).

SIMS: m/z 318 (M$^+$+1).

Example 32

(E)-7-(2-(6-Methyl-2-pyridyl)-(E)-ethenyl)-4(5H),10-dioxo-1H-1,2,3-triazolo[4,5-c][1]benzazepine trifluoroacetate (a) Under an argon atmosphere, 6-methyl-2-pyridylmethyltriphenylphosphonium chloride hydrochloride (210 mg, 0.49 mmol) was suspended in a mixed solvent composed of toluene (5 ml) and N,N-dimethylformamide (2 ml), and potassium tert-butoxide (110 mg, 0.98 mmol) was added to the suspension. Subsequently, 7-formyl-1-(4-methoxybenzyl)-4(5H),10-dioxo-1H-1,2,3-triazolo[4,5-c][1]benzazepine (150 mg, 0.41 mmol) was added thereto, and the mixture was heated at 80° C. overnight. Water was added to the reaction mixture, and the resultant brown crystalline powder was collected by filtration, washed with diethyl ether, and then dried to give 1-(4-methoxybenzyl)-7-(2-(6-methyl-2-pyridyl)-(E)-ethenyl)-4(5H),10-dioxo-1H-1,2,3-triazolo[4,5-c][1]benzazepine (41.0 mg, 22%).

$^1$H-NMR (DMSO-$d_6$): δ 2.52 (3H, s), 3.71 (3H, s), 6.00 (2H, s), 6.91 (2H, d), 7.19 (1H, d), 7.29 (2H, d), 7.41 (1H, d), 7.43 (1H, d), 7.60 (1H, d), 7.63–7.75 (3H, m), 8.18 (1H, d), 11.35 (1H, s).

LCMS: m/z 452 (M$^+$+1).

(b) To a mixed solvent composed of anisole (0.1 ml) and trifluoroacetic acid (1 ml) was dissolved 1-(4-methoxybenzyl)-7-(2-(6-methyl-2-pyridyl)-(E)-ethenyl)-4(5H),10-dioxo-1H-1,2,3-triazolo[4,5-c][1]benzazepine (35.7 mg, 0.08 mmol) prepared in the step (a). The solution was heated at 60° C. for 45 min. The solvent was removed under reduced pressure, and the resultant crystal as a precipitate was collected by filtration, washed with diethyl ether, and then dried to give the title compound: 7-(2-(6-methyl-2-pyridyl)-(E)-ethenyl)-4(5H),10-dioxo-1H-1,2,3-triazolo[4,5-c][1]benzazepine trifluoroacetate as orange crystalline powder (34.6 mg, 98%).

$^1$H-NMR (DMSO-$d_6$): δ 2.60 (3H, s), 7.39 (1H, d), 7.47 (1H, d), 7.65–7.80 (4H, m), 7.96 (1H, t), 8.34 (1H, d), 11.48 (1H, s).

LCMS: m/z 332 (M$^+$+1).

Example 33

4(5H),10-Dioxo-7-(2-(2-quinolyl)-(E)-ethenyl)-1H-1,2,3-triazolo[4,5-c][1]benzazepine trifluoroacetate (a) Triphenyl-2-quinolylmethylphosphonium chloride hydrochloride (181 mg, 0.38 mmol) was suspended in a mixed solvent composed of toluene (5 ml) and N,N-dimethylformamide (2 ml) under an argon atmosphere, and potassium tert-butoxide (86 mg, 0.77 mmol) was added to the suspension. Subsequently, 7-formyl-1-(4-methoxybenzyl)-4(5H),10-dioxo-1H-1,2,3-triazolo[4,5-c][1]benzazepine (115 mg, 0.32 mmol) was added thereto, and the mixture was heated at 80° C. for 6.5 hr. Water was added to the reaction mixture, and the resultant brown crystalline powder was collected by filtration, washed with diethyl ether, and then dried to give 1-(4-methoxybenzyl)-4(5H),10-dioxo-7-(2-(2-quinolyl)-(E)-ethenyl)-1H-1,2,3-triazolo[4,5-c][1]benzazepine (83.2 mg, 54%). $^1$H-NMR (DMSO-$d_6$): 4 3.72 (3H, s), 6.01 (2H, s), 6.91 (2H, d), 7.31 (2H, d), 7.55–7.70 (2H, m), 7.70–7.90 (4H, m), 7.90–8.00 (3H, m), 8.04 (1H, d), 8.22 (1H, d), 8.40 (1H, d), 11.41 (1H, s).

SIMS: m/z 488 (M$^+$+1).

(b) To a mixed solvent composed of anisole (0.2 ml) and trifluoroacetic acid (2 ml) was dissolved 1-(4-methoxybenzyl)-4(5H),10-dioxo-7-(2-(2-quinolyl)-(E)-ethenyl)-1H-1,2,3-triazolo[4,5-c][1]benzazepine (78.2 mg, 0.16 mmol) prepared in the step (a). The mixture was heated at 60° C. for 15 min. The solvent was removed under reduced pressure, and the resultant crystal as a precipitate was collected by filtration, washed with diethyl ether, and dried to give the title compound: 4(5H),10-dioxo-7-(2-(2-quinolyl)-(E)-ethenyl)-1H-1,2,3-triazolo[4,5-c][1]benzazepine trifluoroacetate as yellow crystalline powder (76.3 mg, 99%).

$^1$H-NMR (DMSO-$d_6$): δ 7.64 (1H, d), 7.67 (1H, s), 7.75 (1H, d), 7.80–7.95 (4H, m), 8.04 (1H, d), 8.06 (1H, d), 8.36 (1H, d), 8.53 (1H, d), 11.50 (1H, s).

SIMS: m/z 368 (M$^+$+1).

Example 34

7-Trifluoromethyl-4(5H),10-dioxo-1H-1,2,3-triazolo[4,5-c][1]benzazepine (a) To a solution of 4-trifluoromethyl-2-nitrobenzoic acid (5.23 g, 22.2 mmol) in methanol (200 ml) was added 10% palladium on carbon (500 mg). The mixture was stirred under a hydrogen atmosphere for 35 min. The reaction mixture was filtered through Celite, and the solvent was removed under reduced pressure to give 2-amino-4-trifluoromethylbenzoic acid (4.57 g, 100%).

$^1$H-NMR (CDCl$_3$): δ 5.90–7.60 (2H, brs), 6.88 (1H, d), 6.93 (1H, s), 8.03 (1H, d).

(b) To a solution of 2-amino-4-trifluoromethylbenzoic acid (4.56 g, 22.2 mmol), prepared in the step (a), in tetrahydrofuran (100 ml) were added 10 M borane-dimethyl sulfide complex (4.4 ml, 44.0 mmol) and trimethyl borate (10 ml). The mixture was stirred under ice cooling for 10 min, at room temperature for 15 min, and at 45° C. for 17 hr. Subsequently, 2 ml of 10 M borane-dimethyl sulfide complex was added thereto, and a reaction was allowed to proceed at 45° C. for 15 hr. Thereafter, methanol was added to the reaction mixture under ice cooling to terminate the reaction. The reaction mixture was concentrated under reduced pressure, and the resultant powder was collected by filtration, washed with hexane, and then dried to give 2-amino-4-trifluoromethyl-1-hydroxymethylbenzene (4.08 g, 96%) as yellowish green powder.

$^1$H-NMR (CDCl$_3$): δ 1.65 (1H, brs), 4.35 (2H, brs), 4.71 (2H, s), 6.95 (1H, dd), 6.91 (1H, s), 7.16 (1H, d). (c) Sodium carbonate (2.5 g, 23.6 mmol) and benzyl chloroformate (3.3 ml, 23.1 mmol) were added to a solution of 2-amino-4-trifluoromethyl-1-hydroxymethylbenzene (4.08 g, 21.3 mmol), prepared in the step (b), in a water-tetrahydrofuran 1:1 solution (40 ml), and the mixture was stirred at room temperature for 21 hr. Diethyl ether and water were added to the reaction mixture, followed by extraction with diethyl ether. The organic layer was washed with saturated brine and dried over anhydrous magnesium sulfate, and the solvent was removed under reduced pressure to give 2-benzyloxycarbonylamino-4-trifluoromethyl-1-hydroxymethylbenzene (6.85 g, 99%) as a white solid.

$^1$H-NMR (CDCl$_3$): δ 2.14 (1H, t), 4.74 (2H, d), 5.21 (2H, s), 7.23–7.32 (2H, m), 7.32–7.50 (5H, m), 8.19 (1H, s), 8.34 (1H,s).

(d) Molecular Sieves 4A (20 g) and pyridinium chlorochromate (6.8 g, 31.5 mmol) were added to a solution of 2-benzyloxycarbonylamino-4-trifluoromethyl-1- hydroxymethylbenzene (6.83 g, 21.0 mmol), prepared in step (c), in methylene chloride (200 ml), and the mixture was stirred under ice cooling for 45 min. Diethyl ether was added to the reaction mixture, and the mixture was filtered through Florisil and silica gel. The solvent was then removed under reduced pressure to give 2-benzyloxycarbonylamino-4-trifluoromethylbenzaldehyde (5.43 g, 80%).

$^1$H-NMR (CDCl$_3$): δ 5.25 (2H, s), 7.32–7.50 (6H, m), 7.79 (1H, d), 8.84 (1H, s), 9.98 (1H, s), 10.70 (1H, s).

EIMS: m/z 323 (M$^+$).

(e) To a solution of diisopropylamine (3.8 ml, 27.1 mmol) in tetrahydrofuran (45 ml) was added, at −78° C. under an argon atmosphere, a 1.68 N butyllithium hexane solution (15.5 ml, 26.0 mmol). The mixture was stirred for 30 min. A solution of ethyl propiolate (2.7 ml, 26.6 mmol) in tetrahydrofuran (9 ml) and a solution of 2-benzyloxycarbonylamino-4-trifluoromethylbenzaldehyde (3.23 g, 9.99 mmol, prepared in the step (d), in tetrahydrofuran (20 ml) were added in that order, and the mixture was stirred at −78° C. for 10 min. A solution of acetic acid (3.5 ml, 61.1 mmol) in tetrahydrofuran (10 ml) was then added to the reaction mixture, and water was added thereto, followed by extraction with ethyl acetate. The organic layer was washed with dilute hydrochloric acid, water, a saturated aqueous sodium bicarbonate solution, and saturated brine in that order. It was then dried over anhydrous magnesium sulfate, and the solvent was removed under reduced pressure to give ethyl 4-(2-benzyloxycarbonyl) amino-4-trifluoromethylphenyl) -4-hydroxy-2-butynoate (5.43 g). Ethyl 4-(2-benzyloxycarbonyl )amino-4-trifluoromethylphenyl )-4-hydroxy-2-butynoate thus prepared was dissolved in toluene (20 ml), 4-methoxybenzylazide (4.89 g, 30.0 mmol) was added to the solution, and the mixture was stirred at 100° C. for 8 hr. The reaction mixture was cooled to room temperature and purified by column chromatography on silica gel (hexane:ethyl acetate=1:2) to give an about 2:3 mixture of ethyl 4-(1-(2-benzyloxycarbonylamino-4-trifluoromethylphenyl)-1-hydroxymethyl)-1-(4-methoxybenzyl)-1,2,3-triazole-5-carboxylate (e-1: low polar product (LP)) and ethyl 5-(1-(2-benzyloxycarbonylamino-4-trifluoromethylphenyl)-1-hydroxymethyl)-1-(4-methoxybenzyl )-1,2,3-triazole-4-carboxylate (e-2: high polar product (MP)) (4.14 g, 71%).

2:3 mixture of e-1 (LP) and e-2 (MP):

$^1$H-NMR (CDCl$_3$): δ 1.21 (9/5H, m), 1.42 (6/5H, t), 3.62 (6/5H, s), 3.75–3.82 (2/5H, m), 3.78 (9/5H, s), 4.25–4.35 (6/5H, m), 4.35–4.45 (4/5H, m), 5.20–5.35 (2/5H, m), 5.22 (6/5H, s), 5.64 (2/5H, d), 5.83 (6/5H, s), 5.95–6.05 (4/5H, m), 6.31 (3/5H, d), 6.41 (2/5H, d), 6.49 (4/5H, d), 6.80–6.95 (2H, m), 7.00 (3/5H, d), 7.15–7.30 (16/5H, m), 7.30–7.55 (5H, m), 8.25 (2/5H, s), 8.30 (2/5H, s), 8.36 (3/5H, s), 8.56 (3/5H, s).

SIMS: m/z 585 (M$^+$+1).

(f) The 2:3 mixture of the compound e-1 and the compound e-2 (5.32 g, 9.10 mmol) in the step (e) was dissolved in methylene chloride (90 ml), active manganese dioxide (16.0 g) was added to the solution, and the mixture was stirred at room temperature for 2 hr. The reaction mixture was filtered through Celite and the Celite was washed with ethyl acetate, and the combined solvent was removed under reduced pressure to give a 1:2 mixture of ethyl 4-(2-benzyloxycarbonylamino-4-trifluoromethylbenzoyl)-1-(4-methoxybenzyl)-1,2,3-triazole-5-carboxylate (f-1: (LP)) and ethyl 5-(2-benzyloxycarbonylamino-4-trifluoromethylbenzoyl)-1-(4-methoxybenzyl)-1,2,3-triazole-5-carboxylate (f-2: (MP)) as a yellow solid (5.14 g, 97%).

1:2 mixture of f-1 (LP) and f-2 (MP):

$^1$H-NMR (CDCl$_3$): δ 1.05–1.15 (3H, m), 3.57 (1H, s), 3.80 (2H, s), 4.15–4.25 (2H, m), 5.25 (4/3H, s), 5.29 (2/3H, s), 5.52 (2/3H, brs), 5.83 (4/3H, s), 6.49 (2/3H, d), 6.80–7.00 (3H, m), 7.23–7.51 (23/3H, m), 7.92 (2/3H, d), 8.79 (1/3H, s), 8.88 (2/3H, s).

SIMS: m/z 583 (M$^+$+1).

(g) The 1:2 mixture of ethyl 4-(2-benzyloxycarbonylamino-4-trifluoromethylbenzoyl)-1-(4-methoxybenzyl)-1,2,3-triazole-5-carboxylate (f-1: (LP)) and ethyl 5-(2-benzyloxycarbonylamino-4-trifluoromethylbenzoyl)-1-(4-methoxybenzyl)-1,2,3-triazole-5-carboxylate (f-2: (MP)) (5.14 g, 8.82 mmol) prepared in the step (f) was dissolved in ethyl acetate (100 ml), 10% palladium on carbon (514 mg) was added to the solution, and the mixture was stirred at room temperature under a hydrogen atmosphere for 3 hr. The reaction mixture was filtered through Celite, and the filtrate was concentrated under reduced pressure to give a 1:2 mixture of ethyl 4-(2-amino-4-trifluoromethylbenzoyl)-1-(4-methoxybenzyl)-1,2,3-triazole-5-carboxylate (g-1: LP) and ethyl 5-(2-amino-4-trifluoromethylbenzoyl)-1-(4-methoxybenzyl)-1,2,3-triazole-4-carboxylate (g-2: MP) as a yellow solid (4.08 g, 100%).

1:2 mixture of g-1 (LP) and g-2 (MP)

$^1$H-NMR (CDCl$_3$): δ 1.10 (2H, t), 1.13 (1H, t), 2.50 (2H, brs), 3.63 (1H, s), 3.80 (2H, s), 4.18–4.25 (2H, m), 5.50 (2/3H, brs), 5.86 (4/3H, s), 6.50 (1/3H, dd), 6.60 (2/3H, d), 6.71 (1/3H, d), 6.79 (2/3H, dd), 6.88 (4/3H, d), 6.89 (1/3H, s), 6.96 (2/3H, s), 7.02 (2/3H, d), 7.36 (4/3H, d), 7.63 (2/3H, d).

EIMS: m/z 448 (M$^+$).

(h) Anisole (1.5 ml) and trifluoroacetic acid (30.0 ml) were added to the 1:2 mixture of ethyl 4-(2-amino-4-trifluoromethylbenzoyl)-1-(4-methoxybenzyl)-1,2,3-triazole-5-carboxylate (g-1: LP) and ethyl 5-(2-amino-4-trifluoromethylbenzoyl)-1-(4-methoxybenzyl)-1,2,3-triazole-4-carboxylate (g-2: MP) (3.48 g, 7.76 mmol) prepared in the above step (g), and the mixture was stirred at 60° C. for 16 hr. The solvent was removed under reduced pressure, and the resultant precipitate was collected by filtration, washed with diisopropyl ether, and then dried -to give the title compound: 7-trifluoromethyl-4(5H), 10-dioxo-1H-1,2,3-triazolo[4,5-c][1]benzazepine (h) as light yellow powder (1.82 g, 83%). A 1 N aqueous sodium hydroxide solution (10.5 ml) and water (150 ml) were added to 7-trifluoromethyl-4(5H),10-dioxo-1H-1,2,3-triazolo[4,5-c][1]benzazepine (h) (1.00 g, 3.54 mmol), and the mixture was purified on Diaion HP-20 (water:acetone=4:1) to give a sodium salt of the title compound: 7-trifluoromethyl-4(5H), 10-dioxo-1H-1,2,3-triazolo[4,5-c][1]benzazepine (h') (710 mg, 66%).

(h):

$^1$H-NMR (DMSO-d$_6$): δ 7.63 (1H, d), 7.97 (1H, s), 8.47 (1H, d), 11.58 (1H, s).

SIMS: m/z 283 (M$^+$+1).

(h'):

$^1$H-NMR (DMSO-d$_6$): δ 7.49 (1H, d), 7.91 (1H, s), 8.43 (1H, d), 10.85 (1H, s).

The compounds of the above examples have respective structures summarized in the following table.

TABLE 1
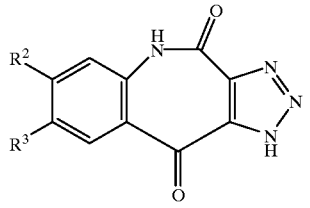
| Ex. No. | R² | R³ |
|---|---|---|
| 1 | CH=CHCONH—[2-(CO₂H)phenyl] (E) | H |
| 2 | CH₂CH₂CONHCH₂—(2-pyridyl) | H |
| 3 | CH₂CH₂CON(CH₃)CH₂—(2-pyridyl) | H |
| 4 | CH₂CH₂CON(CH₂CH₃)CH₂—(2-pyridyl) | H |
| 5 | CH₂CH₂CON(CH₂—(2-pyridyl))₂ | H |
| 6 | CH₂CH₂CO—(1,2,3,4-tetrahydroisoquinolin-2-yl) | H |
| 7 | CH₂CH₂CO—(2-CO₂CH₃-4,5,6,7-tetrahydrothieno[3,2-c]pyridin-5-yl) | H |
| 8 | CH₂CH₂CO—(4-methylpiperazin-1-yl) | H |
| 9 | CH₂CH₂CONH—(4-pyridyl) | H |
| 10 | CH=CH—(4-pyridyl) (E) | H |
| 11 | CH=CH—(2-pyridyl) (E) | H |

TABLE 1-continued

| 12 | OCH₂CH₂CH₂—N(morpholine) | H |
| 13 | OCH₂CH₂CH₂—N(piperazine)N—CH₂—phenyl | H |
| 14 | OCH₂CH₂CH₂—N(piperidine)—CH₂ (4-methyl) | H |
| 15 | OCH₂CON(CH₂CH₃)CH₂—(2-pyridyl) | H |
| 16 | OCH₂CONHCH₂—(2-pyridyl) | H |
| 17 | OCO—phenyl—CH₃ | H |
| 18 | OCH₂CON(CH₂—(2-pyridyl))₂ | H |
| 19 | OCH₂CON(CH₃)CH₂—(2-pyridyl) | H |
| 20 | NH₂ | H |
| 21 | NHCOCH₃ | H |
| 22 | NHCO—phenyl—OCH₂CH₂CH₂CH₂—phenyl | H |

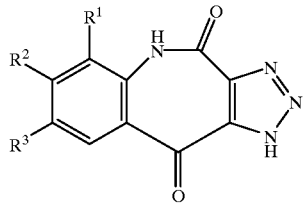

| Ex. No. | R¹ | R² | R³ |
|---|---|---|---|
| 23 | H | OCH₃ | OCH(CH₃)₂ |
| 24 | H | OCH(CH₃)₂ | OCH₃ |
| 25 | H | OCH(CH₃)₂ | OCH(CH₃)₂ |
| 26 | H |  | —O—CH₂—O— |
| 27 | H | CH₃ | OCH₂CO—phenyl—OCH₃ |
| 28 | H | CH₃ | OH |

TABLE 1-continued

| | | | |
|---|---|---|---|
| 29 | CH$_3$ | H | CH$_3$ |
| 30 | OCH$_3$ | OCH$_3$ | OCH$_3$ |
| 31 | H | CH=CH— (E<<Z) | H |
| 32 | H | CH=CH—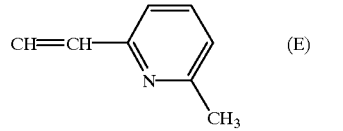 (E) | H |
| 33 | H | CH=CH—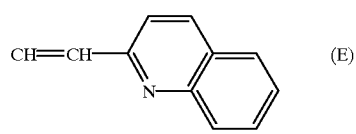 (E) | H |
| 34 | H | CF$_3$ | H |

Pharmacological test

Histamine release reaction inhibition test (1) Preparation of antiserum

Rat anti-dinitrophenylated ascaris protein (hereinafter referred to as "DNP-As") serum was prepared according to the method established by Tada et al. (Tada, T. and Okumura, K., J. Immun. 106(4), 1971). Specifically, 1010 organisms of Bordetella pertussis and 1 mg of DNP-As were intramuscularly administered to the foot pad of the limbs of Brown norway male rats weighing 200 g, and, five days after the administration, 0.5 mg of DNP-As was intramuscularly administered to the back. Three days after that, blood was collected to prepare an antiserum. The titer of the antiserum was determined by using a 48-hr passive cutaneous anaphylaxis reaction using a rat and found to be 1:1000 to 1:2000.

(2) Induction of histamine release reaction and release reaction inhibitory activity The above serum was diluted four times with physiological brine, and 1 ml of the diluted serum was intraperitoneally administered to a Wistar male rat. Two days after the administration, the abdominal cavity was washed with phosphate buffer, and intraperitoneal cells were collected. The cells were adjusted to $10^5$ cells/ml and stimulated with 1 pg/ml DNP-As, and the amount of the histamine released on the supernatant was measured by the method established by Shore et al (Shore, P. A., Burkhalter, A. H. and Chon Jr. V. H. J. Pharm. Exp. Ther., 127 , 182–186 (1959)).

The amount of the released histamine treated with $10^{-5}$ to $10^{-10}$ M test compound was compared with that of non-treated group. The dose of the test compound required for inhibiting the histamine release reaction by 50% (IC$_{50}$) was calculated based on the percentage inhibition. The results are summarized in the following table. IC$_{50}$ of sodium cromoglicate was used as a control.

As is apparent from the following results, the compounds of the present invention had excellent histamine release reaction inhibitory activity.

TABLE 2

| Test compound (Example number) | IC$_{50}$ (nM) |
|---|---|
| 1 | 6.0 |
| 2 | 4.4 |
| 3 | 4.6 |
| 4 | 13.0 |
| 5 | 2.9 |
| 6 | 4.5 |
| 7 | 12.0 |
| 8 | 9.5 |
| 9 | 3.9 |
| 10 | 2.4 |
| 11 | 1.8 |
| 12 | 3.6 |
| 13 | 11.0 |
| 14 | 11.0 |
| 15 | 9.9 |
| 16 | 2.8 |
| 17 | 4.1 |
| 18 | 6.2 |
| 21 | 4.6 |
| 22 | 8.1 |
| 23 | 2.4 |
| 25 | 4.9 |
| 26 | 69.0 |
| 27 | 10.0 |
| 28 | 12.0 |
| 29 | 31.0 |
| 30 | 8.7 |
| 31 | 2.0 |
| 32 | 1.2 |
| 33 | 0.4 |
| 34 | 5.3 |
| Sodium cromoglicate | 1800.0 |

Immediate and late phase allergic response inhibition test

Wister male rats weighing of 200 g were provided. 1010 organisms of Bordetella pertussis and 1 mg of dinitrophenylated ovalbumin (hereinafter abbreviated to "DNP-OA") were intramuscularly administered into the foot pad of the limbs of the rats except for the right hind leg. Further, ten days after the administration, 5 pg/site DNP-OA was subcutaneously administered to the right hind leg to induce allergic foot-pad edema reaction. The inhibitory activity of the test compounds was determined in such a manner that the volume of edema 30 min after the induction of the allergic reaction was regarded as an immediate phase allergic response and the volume of edema 8 hr after the induction of the allergic reaction was regarded as a late phase allergic response. Each test compound was dissolved or suspended in a 0.25% Tween 80 solution, and the solution or suspension was orally administered at a dose of 20 mg/kg 10 min before the induction of the allergic reaction.

Only the 0.25% Tween 80 solution was administered to the control group of rats not treated with any test compound, and 100 mg/kg sodium cromoglicate was subcutaneously or orally administered to the positive control group of rats.

The percentage inhibition of the allergic foot-pad edema reaction was determined by the following equation. The inhibition (%) of the immediate phase and the late phase by the compounds of the present invention is summarized in the following table.

Percentage inhibition of allergic foot-pad edema reaction=(A−B)/A×100 wherein A: average edema volume for the non-treated control group of rats; and

B: average edema volume for the group of rats with the test compound administered.

TABLE 2

|  | Inhibition (%) | |
| --- | --- | --- |
| Test compound (Example number) | Immediate phase response | Late phase response |
| 2 | 57 | 43 |
| 3 | 44 | 14 |
| 4 | 48 | 21 |
| 5 | 40 | 43 |
| 6 | 19 | 29 |
| 7 | 20 | −3 |
| 8 | 42 | 20 |
| 9 | 30 | 33 |
| 10 | 44 | 59 |
| 12 | 46 | 42 |
| 13 | 28 | 28 |
| 14 | 32 | 15 |
| 15 | 34 | 25 |
| 16 | 48 | 35 |
| 17 | 44 | 24 |
| 18 | 40 | 5 |
| 21 | 43 | 26 |
| 22 | 40 | 41 |
| 23 | 71 | 56 |
| 25 | 59 | 38 |
| 26 | 43 | 29 |
| 28 | 51 | 48 |
| 30 | 58 | 51 |
| 32 | 55 | 43 |
| 34 | 66 | 59 |
| Sodium cromoglicate*1) | 75 | 53 |
| Sodium cromoglicate*2) | 16 | 20 |

*1): subcutaneous administration
*2): oral administration

What is claimed is:

1. A tricyclic benzazepine compound represented by the following formula (I) and a pharmaceutically acceptable salt thereof:

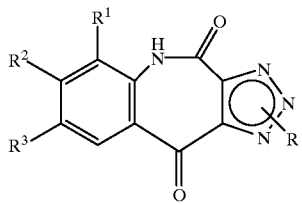

wherein

R represents any one of the following (a) to (c):
(a) a hydrogen atom;
(b) a benzyl group
which may be substituted by a halogen atom, a hydroxyl group, a nitro group, $C_{1-4}$ alkyl, or $C_{1-4}$ alkoxy; and
(c) a protective group for a triazole group, and
$R^1$, $R^2$, and $R^3$, which may be the same or different, represent any one of the following (a) to (g):
(a) a hydrogen atom;
(b) $C_{1-4}$ alkyl
which may be substituted by a halogen atom, a hydroxyl group, or $C_{1-4}$ alkoxy;
(c) an optionally protected hydroxyl group;
(d) $C_{2-12}$ alkenyl
which may be substituted by
(1) group —$CONR^4R^5$
wherein $R^4$ and $R^5$, which may be the same or different, represent
(i) a hydrogen atom,
(ii) phenyl
which may be substituted by a halogen atom, a hydroxyl group, $C_{1-4}$ alkyl optionally substituted by a saturated five- to seven-membered heterocyclic ring containing one or two nitrogen atoms optionally substituted by $C_{1-4}$ alkyl, $C_{1-4}$ alkoxy, or carboxyl, or
which may be substituted by a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring, or
(iii) a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring, or
(2) a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring;
(e) $C_{1-12}$ alkoxy
which may be substituted by
(1) amino
which may be substituted by $C_{1-4}$ alkyl, acyl, or a saturated or unsaturated five- to seven-membered heterocyclic ring containing one or more atoms selected from oxygen, nitrogen, and sulfur atoms, the heterocyclic ring being optionally substituted by $C_{1-4}$ alkyl or phenyl $C_{1-4}$ alkyl or optionally condensed with other ring to form a bicyclic ring, the nitrogen atom of the amino optionally constituting a part of a ring to form a saturated five- to seven-membered heterocyclic ring, or (2) group —$CONR^6R^7$ wherein $R^6$ and $R^7$, which may be the same or different, represent (i) a hydrogen atom, or (ii) $C_{1-4}$ alkyl which may be substituted by a saturated five- to seven-membered heterocyclic ring containing one or more atoms selected from oxygen, nitrogen, and sulfur atoms;

(f) group —$NR^8R^9$ wherein $R^8$ and $R^9$, which may be the same or different, represent (1) a hydrogen atom, (2) $C_{1-4}$ alkyl, (3) group —$COR^{10}$ wherein $R^{10}$ represents (i) a hydrogen atom, (ii) $C_{1-4}$ alkyl which may be substituted by a halogen atom, a hydroxyl group, $C_{1-4}$ alkoxy, or cycloalkyl, or (iii) phenyl which may be substituted by a halogen atom, a hydroxyl group, $C_{1-4}$ alkyl, or $C_{1-6}$ alkoxy, the alkoxy being optionally substituted by phenyl, (4) group —$CO_2R^{11}$ wherein $R^{11}$ represents (i) $C_{1-4}$ alkyl which may be substituted by a halogen atom, a hydroxyl group, $C_{1-4}$ alkoxy, or cycloalkyl, (ii) phenyl $C_{1-4}$ alkyl which may be substituted by a halogen atom, a hydroxyl group, $C_{1-4}$ alkyl, or $C_{1-4}$ alkoxy, (iii) phenyl which may be substituted by a halogen atom, a hydroxyl group, $C_{1-4}$ alkyl, or $C_{1-4}$ alkoxy, or (5) group —$SO_2R^{12}$ wherein $R^{12}$ represents (i) $C_{1-10}$ alkyl which may be substituted by a halogen atom, a hydroxyl group, an oxo group, $C_{1-4}$ alkoxy, or cycloalkyl, (ii) phenyl which may be substituted by a halogen atom, a hydroxyl group, $C_{1-4}$ alkyl or $C_{1-4}$ alkoxy or may be condensed with other ring to form a bicyclic ring;

(g) group —$(CH_2)_p$—$CONR^{13}R^{14}$ wherein $R^{13}$ and $R^{14}$, which may be the same or different, represent (1) a hydrogen atom, (2) $C_{1-4}$ alkyl which may be substituted by a saturated five- to seven-membered heterocyclic ring containing one or two atoms selected from oxygen, nitrogen, and sulfur atoms, (3) a saturated or unsaturated five- to seven-membered heterocyclic ring formed by combining $R^{13}$ and $R^{14}$ with a nitrogen atom bonded thereto, the heterocyclic ring optionally containing one or more atoms selected from oxygen, nitrogen, and sulfur atoms or being optionally condensed with other ring to form a bicyclic ring, or (4) a saturated or unsaturated five- to seven-membered heterocyclic ring containing one or two atoms selected from oxygen, nitrogen, and sulfur atoms, and p is an integer of 2.

2. The compound according to claim 1, wherein R represents a hydrogen atom and $R^1$, $R^2$, and $R^3$ represent a hydrogen atom or substituted $C_{1-4}$ alkyl.

3. The compound according to claim 1, wherein R represents a hydrogen atom and $R^1$, $R^2$, and $R^3$ represent a hydrogen atom or substituted $C_{1-12}$ alkoxy.

4. The compound according to claim 1, wherein R and $R^1$ represent a hydrogen atom and $R^2$ and $R^3$ represent a hydrogen atom, substituted $C_{1-4}$ alkyl, substituted $C_{2-12}$ alkenyl, or substituted $C_{1-12}$ alkoxy.

5. The compound according to claim 1, wherein R and $R^1$ represent a hydrogen atom and $R^2$ and $R^3$ represent a hydrogen atom or substituted $C_{1-4}$ alkyl.

6. The compound according to claim 1, wherein R and $R^1$ represent a hydrogen atom and $R^2$ and $R^3$ represent a hydrogen atom or substituted $C_{2-12}$ alkenyl.

7. The compound according to claim 1, wherein R and RI represent a hydrogen atom and $R^2$ and $R^3$ represent a hydrogen atom or substituted $C_{1-12}$ alkoxy.

8. The compound according to claim 1, wherein R and $R^1$ represent a hydrogen atom and $R^2$ and $R^3$ represent a hydrogen atom, substituted $C_{1-4}$ alkyl, or substituted $C_1l_{12}$ alkoxy.

9. The compound according to claim 1, wherein R, $R^1$, and $R^3$ represent a hydrogen atom and $R^2$ represents substituted $C_{1-4}$ alkyl.

10. The compound according to claim 1, wherein R, $R^1$ and $R^3$ represent a hydrogen atom and $R^2$ represents substituted $C_{2-12}$ alkenyl.

11. The compound according to claim 1, wherein R, $R^1$, and $R^3$ represent a hydrogen atom and $R^2$ represents substituted $C_{1-12}$ alkoxy.

12. The compound according to claim 1, wherein R, $R^1$, and $R^3$ represent a hydrogen atom and $R^2$ represents substituted or unsubstituted amino.

13. The compound according to claim 1, wherein R and $R^2$ represent a hydrogen atom and $R^1$ and $R^3$ represent substituted $C_{1-4}$ alkyl.

14. A compound selected from:

7-(2-(N-(2-carboxyphenyl)carbamoyl)-(E)-ethenyl)-4(5H), 10-dioxo-1H-1,2,3-triazolo[4,5-c][1]benzazepine;

4(5H ), 10-dioxo-7-(2-(N-(2-pyridyl)methyl)carbamoyl) ethyl-1H-1,2,3-triazolo[4,5-c][1]benzazepine;

4(5H),10-dioxo-7-(2-(N-methyl-N-(2-pyridyl)methyl) carbamoyl)ethyl-1H-1,2,3-triazolo[4,5-c][1]benzazepine;

7-(2-(N-ethyl-N-(2-pyridyl)methyl)carbamoyl)ethyl-4(5H), 10-dioxo-1H-1,2,3-triazolo[4,5-c][1]benzazepine;

7-(2-(N,N-bis(2-pyridylmethyl))carbamoyl)ethyl- 4(5H), 10-dioxo-1H-1,2,3-triazolo[4,5-c][1]benzazepine;

7-(2-(1,2,3,4-tetrahydro-2-isoquinolyl)carbonylethyl)-4 (5H),10-dioxo-1H-1,2,3-triazolo[4,5-c][1]benzazepine;

7-(2-(2-methoxycarbonyl-4,5,6,7-tetrahydrothieno[3,2-c] pyridin-5-yl)carbonylethyl)-4(5H), 10-dioxo-1H-1,2,3-triazolo[4,5-c][1]benzazepine;

7-(2-(4-methylpiperazin-1-yl)carbonylethyl)-4(5H),10-dioxo-1H-1,2,3-triazolo[4,5-c][1]benzazepine;

7-(2-(N-(4-pyridylamino))carbamoyl)ethyl-4(5H),10-dioxo-1H-1,2,3-triazolo[4,5-c][1]benzazepine;

4(5H),10-dioxo-7-(2-(4-pyridyl)-(E)-ethenyl)-1H-1,2,3-triazolo[4,5-c][1]benzazepine;

4(5H),10-dioxo-7-(2-(2-pyridyl)-(E)-ethenyl)-1H-1,2,3-triazolo[4,5-c][1]benzazepine;

7-(3-morpholinopropoxy)-4(5H),10-dioxo-1H-1,2,3-triazolo[4,5-c][1]benzazepine;

7-(3-(4-methyl-1-piperazino)propoxy)-4(5H),10-dioxo-1H-1,2,3-triazolo[4,5-c][1]benzazepine;

7-(3-(4-benzylpiperidyl)propoxy)-4(5H), 10-dioxo-1H-1,2,3-triazolo[4,5-c][1]benzazepine;

7-(N-ethyl-N-(2-pyridylmethyl)carbamoylmethyloxy)-4(5H),10-dioxo-1H-1,2,3-triazolo[4,5-c][1]benzazepine;

4(5H),10-dioxo-7-(N-(2-pyridylmethyl)carbamoylmethyloxy)-1H-1,2,3-triazolo[4,5-c][1]benzazepine;

4(5H),10-dioxo-7-(4-toluoyloxy)-1H-1,2,3-triazolo[4,5-c][1]benzazepine;

4(5H),10-dioxo-7(N,N-bis(2-pyridylmethyl)carbamoylmethyloxy)-1H-1,2,3-triazolo[4,5-c][1]benzazepine;

7-(N-methyl-N-(2-pyridylmethyl)carbamoylmethyloxy)-4(5H),10-dioxo-1H-1,2,3-triazolo[4,5-c][1]benzazepine;

7-amino-4(5H),10-dioxo-1H-1,2,3-triazolo[4,5-c][1]benzazepine;

7-acetylamino-4(5H),10-dioxo-1H-1,2,3-triazolo[4,5-c][1]benzazepine;

4(5H),10-dioxo-7-(4-(4-phenylbutoxy)benzoylamino)-1H-1,2,3-triazolo[4,5-c][1]benzazepine;

8-isopropoxy-7-methoxy-4(5H),10-dioxo-1H-1,2,3-triazolo[4,5-c][1]benzazepine;

7-isopropoxy-8-methoxy-4(5H),10-dioxo-1H-1,2,3-triazolo[4,5-c][1]benzazepine;

7,8-diisopropoxy-4(5H),10-dioxo-1H-1,2,3-triazolo[4,5-c][1]benzazepine;

7,8-methylenedioxy-4(5H),10-dioxo-1H-1,2,3-triazolo[4,5-c][1]benzazepine;

8-(4-methoxyphenacyloxy)-7-methyl-4(5H),10-dioxo-1H-1,2,3-triazolo[4,5-c][1]benzazepine;

8-hydroxy-7-methyl-4(5H),10-dioxo-1H-1,2,3-triazolo[4,5-c][1]benzazepine;

6,8-dimethyl-4(5H),10-dioxo-1H-1,2,3-triazolo[4,5-c][1]benzazepine;

6,7,8-trimethoxy-4(5H),10-dioxo-1H-1,2,3-triazolo[4,5-c][1]benzazepine;

4(5H),10-dioxo-7-(2-(3-pyridyl)ethenyl)-1H-1,2,3-triazolo[4,5-c][1]benzazepine;

7-(2-(6-methyl-2-pyridyl)-(E)-ethenyl)-4(5H),10-dioxo-1H-1,2,3-triazolo[4,5-c][1]benzazepine;

4(5H),10-dioxo-7-(2-(2-quinolyl)-(E)-ethenyl)-1H-1,2,3-triazolo[4,5-c][1]benzazepine; and 7-trifluoromethyl-4(5H),10-dioxo-1H-1,2,3-triazolo[4,5-c][1]benzazepine.

15. A pharmaceutical composition comprising as an active ingredient the compound according to any one of claims 1 to 14 or a pharmacologically acceptable salt thereof.

16. A method for treating allergic diseases, comprising administering an effective amount of the compound according to any one of claims 1 to 14 to a mammal in need of such treatment.

17. The method according to claim 16, wherein the mammal is a human being.

18. A compound represented by the following formula (II) or a salt thereof:

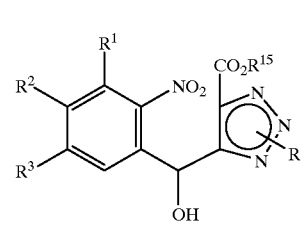

(II)

wherein R, $R^1$, $R^2$, and $R^3$ are as defined in claim 1 in connection with the formula (I) and $R^{15}$ represents a hydrogen atom, optionally substituted $C_{1-6}$ alkyl, or a protective group of carboxyl.

19. A compound represented by the following formula (III) or a salt thereof:

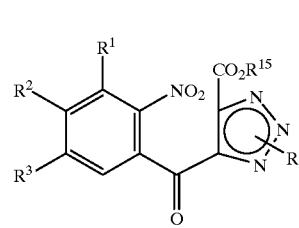

(III)

wherein R, $R^1$, $R^2$, and $R^3$ are as defined in claim 1 in connection with the formula (I) and $R^{15}$ represents a hydrogen atom, optionally substituted $C_{1-6}$ alkyl, or a protective group of carboxyl.

20. A compound represented by the following formula (IV) or a salt thereof:

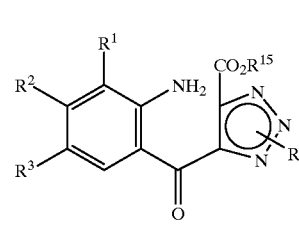

(IV)

wherein R, $R^1$, $R^2$, and $R^3$ are as defined in claim 1 in connection with the formula (I) and $R^{15}$ represents a hydrogen atom, optionally substituted $C_{1-6}$ alkyl, or a protective group of carboxyl.

* * * * *